(12) United States Patent
Probst et al.

(10) Patent No.: US 9,402,887 B2
(45) Date of Patent: Aug. 2, 2016

(54) COMPOSITION FOR TREATING PROSTATE CANCER (PCA)

(71) Applicant: CureVac AG, Tübingen (DE)

(72) Inventors: Jochen Probst, Wolfschlugen (DE); Ingmar Hoerr, Tubingen (DE); Thomas Lander, Konigstein I. Taunus (DE)

(73) Assignee: CureVac AG, Tübingen (DE)

( * ) Notice: Subject to any disclaimer, the term of this patent is extended or adjusted under 35 U.S.C. 154(b) by 284 days.

(21) Appl. No.: 13/759,542

(22) Filed: Feb. 5, 2013

(65) Prior Publication Data

US 2013/0251742 A1 Sep. 26, 2013

Related U.S. Application Data

(63) Continuation of application No. 12/682,187, filed as application No. PCT/EP2008/008504 on Oct. 8, 2008, now abandoned.

(30) Foreign Application Priority Data

Oct. 9, 2007 (WO) ................. PCT/EP2007/008771

(51) Int. Cl.
A61K 39/00 (2006.01)

(52) U.S. Cl.
CPC ............. *A61K 39/00* (2013.01); *A61K 39/0011* (2013.01); *A61K 2039/53* (2013.01)

(58) Field of Classification Search
None
See application file for complete search history.

(56) References Cited

U.S. PATENT DOCUMENTS

| | | |
|---|---|---|
| 2005/0032730 A1 | 2/2005 | Von Der Mulbe et al. |
| 2005/0059624 A1 | 3/2005 | Hoerr et al. |
| 2005/0063975 A1 | 3/2005 | Afar et al. |
| 2005/0250723 A1 | 11/2005 | Hoerr et al. |
| 2006/0188490 A1 | 8/2006 | Hoerr et al. |
| 2006/0263342 A1 | 11/2006 | Eisenbach et al. |
| 2007/0056859 A1 | 3/2007 | Sherman et al. |
| 2007/0065859 A1 | 3/2007 | Wang et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2008/0267873 A1 | 10/2008 | Hoerr et al. |
| 2009/0324584 A1 | 12/2009 | Hoerr et al. |
| 2010/0203076 A1 | 8/2010 | Fotin-Mleczek et al. |
| 2010/0291156 A1 | 11/2010 | Barner et al. |
| 2011/0053829 A1 | 3/2011 | Baumhof et al. |
| 2012/0009221 A1 | 1/2012 | Hoerr et al. |

FOREIGN PATENT DOCUMENTS

| | | |
|---|---|---|
| DE | 102006007433 | 8/2007 |
| EP | 1083232 | 3/2001 |
| EP | 1905844 | 4/2008 |
| JP | 2003/504080 | 2/2003 |
| JP | 2003/517306 | 5/2003 |
| JP | 2006/512047 | 4/2006 |
| WO | WO 00/49158 | 8/2000 |
| WO | WO 01/04143 | 1/2001 |
| WO | WO 01/40276 | 6/2001 |
| WO | WO 02/098443 | 12/2002 |
| WO | WO 03/059381 | 7/2003 |
| WO | WO 03/104272 | 12/2003 |
| WO | WO 2004/004743 | 1/2004 |
| WO | WO 2004/016643 | 2/2004 |
| WO | WO 2004/067570 | 8/2004 |
| WO | WO 2005/016376 | 2/2005 |
| WO | WO 2005/113601 | 12/2005 |
| WO | WO 2006/008154 | 1/2006 |
| WO | WO 2006/024518 | 3/2006 |
| WO | WO 2008/014979 | 7/2008 |
| WO | WO 2008/077592 | 7/2008 |
| WO | WO 2008/083949 | 7/2008 |

OTHER PUBLICATIONS

Cunha et al. Tissue-specificity of prostate specific antigens: Comparative analysis of transcript levels in prostate and non-prostatic tissues. Cancer Letters, vol. 236, pp. 229-238, 2006.*

Lee et al. The nucleotide sequence of a human protamine 1 cDNA. Nucleic Acids Research, vol. 15, No. 18, p. 7639, 1987.*

Carralot et al., "Production and characterization of amplified tumor-derived cRNA libraries to be used as vaccines against metastatic melanomas," *Genetic Vaccines and Therapy*, 3(6):1-10, 2005.

Hara et al., "Reverse transcription-polymerase chain reaction detection of prostate-specific antigen, prostate-specific membrane antigen, and prostate stem cell antigen in one milliliter of peripheral blood: value for the staging of prostate cancer," *Clin Cancer Res*, 8(6):1794-1799, 2002.

Haupt et al., "The potential of DNA vaccination against tumor-associated antigens for antitumor therapy," *Exp Biol Med (Maywood)*, 227(4):227-237, 2002.

Machlenkin et al., "Human CTL epitopes prostatic acid phosphatase-3 and six-transmembrane epithelial antigen of prostate-3 as candidates for prostate cancer immunotherapy," *Cancer Res.*, 65(14):6435-6442, 2005.

(Continued)

*Primary Examiner* — Jennifer Dunston
(74) *Attorney, Agent, or Firm* — Parker Highlander PLLC

(57) ABSTRACT

The present invention relates to an active (immunostimulatory) composition comprising at least one RNA, preferably an mRNA, encoding at least two (preferably different) antigens capable of eliciting an (adaptive) immune response in a mammal wherein the antigens are selected from the group consisting of PSA (Prostate-Specific Antigen), PSMA (Prostate-Specific Membrane Antigen), PSCA (Prostate Stem Cell Antigen), and STEAP (Six Transmembrane Epithelial Antigen of the Prostate). The invention furthermore relates to a vaccine comprising an active (immunostimulatory) composition, and to the use of the active (immunostimulatory) composition (for the preparation of a vaccine) and/or of the vaccine for eliciting an (adaptive) immune response for the treatment of prostate cancer (PCa), preferably of neoadjuvant and/or hormone-refractory prostate cancers, and diseases or disorders related thereto. Finally, the invention relates to kits, particularly to kits of parts, containing the active (immunostimulatory) composition and/or the vaccine.

48 Claims, 23 Drawing Sheets

(56) References Cited

OTHER PUBLICATIONS

Figure 13:
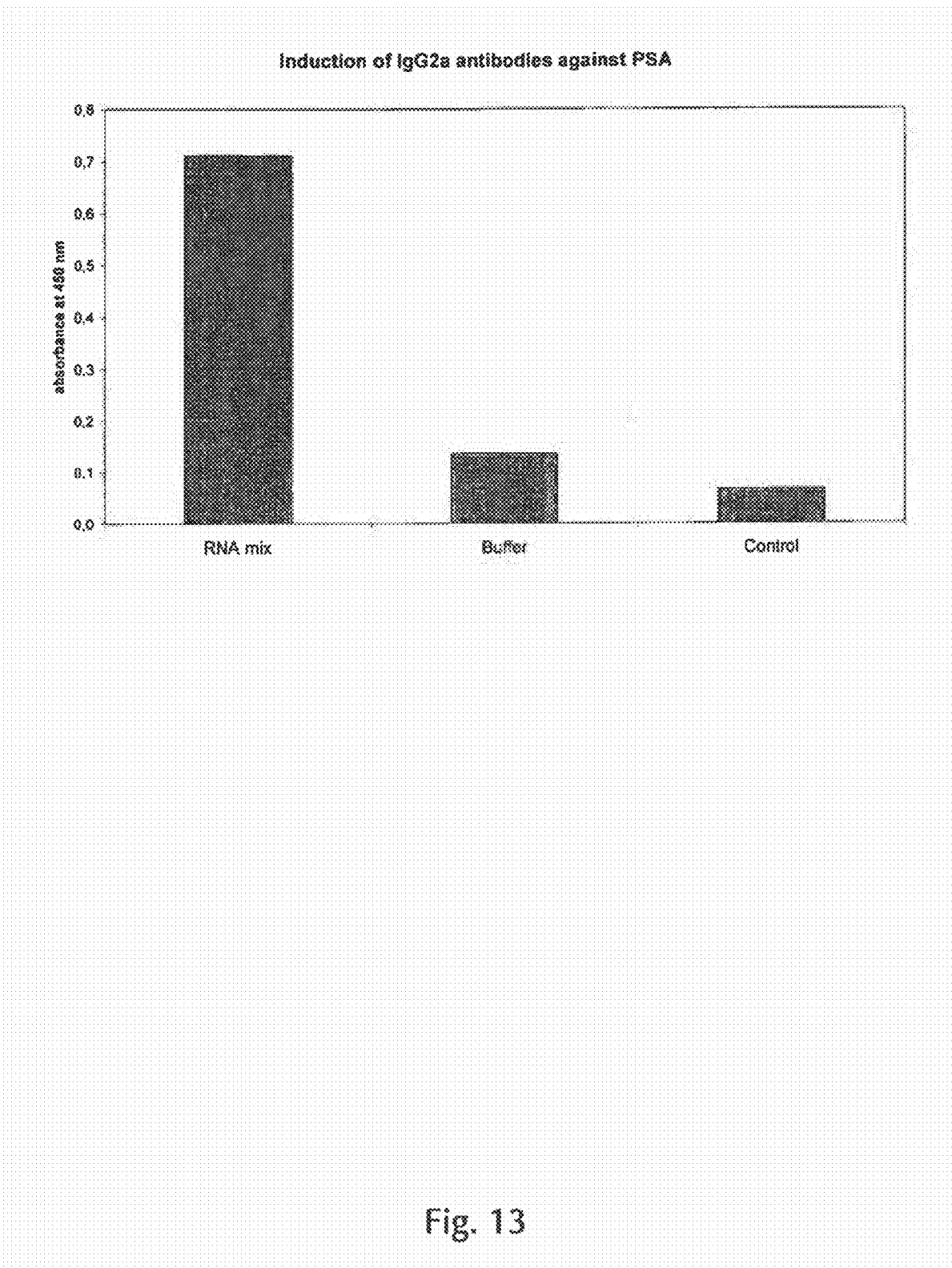

Ahern, "Biochemical, reagents kits offer scientists good return on investment," *The Scientist*, 9(15):20, 1995.
Bettinger et al., "Peptide-mediated RNA delivery: a novel approach for enhanced transfection of primary and post-mitotic cells," *Nucleic Acids Research*, 29(18):3882-3891, 2001.
Fotin-Mleczek et al., "Messenger RNA based vaccines with dual activity induce balanced TLR-7 dependent adaptive immune responses and provide antitumor activity," *Journal of Immunotherapy*, 34(1):1-15, 2011.
Grünebach et al., "New developments in dendritic cell-based vaccinations: RNA translated into clinics," *Cancer Immunol. Immunother.*, 54(6):517-525, 2005.
Heil et al., "Species-specific recognition of single-stranded RNA via toll-like receptor 7 and 8," *Science*, 303:1526-1529, 2004.
Heiser et al., "Autologous dendritic cells transfected with prostate-specific antigen RNA stimulate CTL responses against metastatic prostate tumors," *J. Clin. Invest.*, 109(3):409-417, 2002.
Hubert et al., "STEAP: a prostate-specific cell-surface antigen highly expressed in human prostate tumors," *Proc Natl Acad Sci USA*, 96(25):14523-14528, 1999.
Kyte et al., "Immuno-gene therapy of cancer with tumour-mRNA transfected dendritic cells," *Cancer Immunol Immunother.*, 55(11):1432-1442, 2006.
Lochmann et al., "Drug delivery of oligonucleotides by peptides," *European Journal of Pharmaceutics and Biopharmaceutics*, 58(2):237-251, 2004.
Marrari et al., "Vaccination therapy in prostate cancer," *Cancer Immunol. Immunother.*, 56(4):429-445, 2007.
Mitchell et al., "mRNA turnover," *Current Opinion in Cell Biology*, 13(3):320-325, 2001.
Office Action issued in U.S. Appl. No. 12/682,187, mailed Jul. 13, 2012.
Office Action issued in U.S. Appl. No. 12/682,187, mailed Nov. 5, 2012.
PCT International Preliminary Report on Patentability issued in International Application No. PCT/EP2008/008504, dated Apr. 13, 2010.
PCT International Search Report issued in International Application No. PCT/EP2008/008504, dated Jan. 19, 2009.
Pesole et al., "UTRdb and UtRsite: specialized databases of sequences and functional elements of 5' and 3' untranslated regions of eukaryotic mRNAS," *Nucleic Acids Research*, 30(1):335-340, 2002.
Challita-Eid et al., "Monoclonal antibodies to six-transmembrane epithelial antigen of the prostate-1 inhibit intracellular communication in vitro and growth of human tumor xenografts in vivo," *Cancer Research*, 67(12):5798-5805, 2007.
Ross, "Control of messenger RNA stability in higher eukaryotes," *TIG*, 12(5):171-175, 1996.
Scheel et al., "Therapeutic anti-tumor immunity triggered by injections of immunostimulating single-stranded RNA," *Eur. J. Immmunol.*, 36(10):2807-2816, 2006.
Scheel et al., "Toll-like receptor-dependent activation of several human blood cell types by protamine-condensed mRNA," *Eur. J. Immunol.*, 35(5):1557-1566, 2005.
Shiffman et al., "Protein dissociation from DNA in model systems and chromatin," *Nucleic Acids Res.*, 5(9):3409-3426, 1978.
Sobel et al., "Cell lines used in prostate cancer research: a compendium of old and new lines—Part 2," *J. Urol.*, 173(2):360-372, 2005.
Su et al., "Enhanced induction of telomerase-specific CD4(+) T cells using dendritic cells transfected with RNA encoding a chimeric gene product," *Cancer Res.*, 62(17):5041-5048, 2002.
Tourriere et al., "mRNA degradation machines in eukaryotic cells," *Biochimie*, 84:821-837, 2002.
Wilusz et al., "Bringing the role of mRNA decay in the control of gene expression into focus," *TIG*, 20(10):491-497, 2004.
Yang et al., "Murine six-transmembrane epithelial antigen of the prostate, prostate stem cell antigen, and prostate-specific membrane antigen: prostate-specific cell-surface antigens highly expressed in prostate cancer of transgenic adenocarcinoma mouse prostate mice," *Cancer Res.*, 61(15):5857-5860, 2001.
Zohra et al., "Effective delivery with enhanced translational activity synergetically accelerates mRNA-based transfection," *Biochem Biophys Res Commun.*, 358(1):373-378, 2007.
Rittig et al., "Intradermal vaccinations with RNA coding for TAA generate CD8 and CD4 immune responses and induce clinical benefit in vaccinated patients", *Mol Ther.*, 19(5):990-9, 2011.

\* cited by examiner

RNActive CAP-KLK3(GC)-muag-A70-C30 = PSA

GGGAGAAAGCTTACCATGTGGGTGCCGGTCGTGTTCCTGACCCTCAGCGTGACGTGGATCGGCGCCGCGCCCCTG
ATCCTGTCGCGGATCGTGGGGGGCTGGGAGTGCGAGAAGCACAGCCAGCCCTGGCAGGTGCTGGTGGCCAGCCGC
GGCCGGGCCGTGTGCGGCGGCGTGCTGGTGCACCCCAGTGGGTGCTGACCGCCGCCCACTGCATCCGGAACAAG
AGCGTCATCCTGCTGGGCCGGCACAGCCTGTTCCACCCCGAGGACACCGGCCAGGTGTTCCAGGTGAGCCACAGC
TTCCCCCACCCCCTGTACGACATGAGCCTCCTGAAGAACCGGTTCCTGCGGCCCGGCGACGACAGCAGCCACGAC
CTGATGCTGCTGCGGCTGAGCGAGCCCGCCGAGCTGACCGACGCCGTGAAGGTGATGGACCTGCCGACCCAGGAG
CCCGCCCTGGGCACCACCTGCTACGCCAGCGGCTGGGGAGCATCGAGCCCGAGGAGTTCCTCACCCCCAAGAAG
CTGCAGTGCGTGGACCTGCACGTGATCAGCAACGACGTGTGCGCCCAGGTGCACCCCAGAAGGTGACCAAGTTC
ATGCTGTGCGCCGGCCGGTGGACCGGCGGCAAGAGCACCTGCAGCGGCGACAGCGGCGGCCCCCTGGTCTGCAAC
GGCGTGCTGCAGGGCATCACCAGCTGGGGCAGCGAGCCCTGCGCCCTGCCCGAGCGCCCCAGCCTGTACACCAAG
GTGGTGCACTACCGGAAGTGGATCAAGGACACCATCGTGGCCAACCCGTGACCACTAGTTATAAGACTGACTAGC
CCGATGGGCCTCCCAACGGGCCCTCCTCCCCTCCTTGCACCGAGATTAATAAAAAAAAAAAAAAAAAAAAAAAAA
AAAAAAAAAAAAAAAAAAAAAAAAAAAAAAAAAAAAAAAAATATTCCCCCCCCCCCCCCCCCCCCCCCCCCCCTC
TAGACAATTGGAATT

Fig. 1

```
CDS KLK3(wt) = PSA

ATGTGGGTCCCGGTTGTCTTCCTCACCCTGTCCGTGACGTGGATTGGTGCTGCACCCCTCATCCTGTCTCGGATT
GTGGGAGGCTGGGAGTGCGAGAAGCATTCCCAACCCTGGCAGGTGCTTGTGGCCTCTCGTGGCAGGGCAGTCTGC
GGCGGTGTTCTGGTGCACCCCAGTGGGTCCTCACAGCTGCCCACTGCATCAGGAACAAAAGCGTGATCTTGCTG
GGTCGGCACAGCCTGTTTCATCCTGAAGACACAGGCCAGGTATTTCAGGTCAGCCACAGCTTCCCACACCCGCTC
TACGATATGAGCCTCCTGAAGAATCGATTCCTCAGGCCAGGTGATGACTCCAGCCACGACCTCATGCTGCTCCGC
CTGTCAGAGCCTGCCGAGCTCACGGATGCTGTGAAGGTCATGGACCTGCCCACCCAGGAGCCAGCACTGGGGACC
ACCTGCTACGCCTCAGGCTGGGGCAGCATTGAACCAGAGGAGTTCTTGACCCCAAAGAAACTTCAGTGTGTGGAC
CTCCATGTTATTTCCAATGACGTGTGTGCGCAAGTTCACCCTCAGAAGGTGACCAAGTTCATGCTGTGTGCTGGA
CGCTGGACAGGGGGCAAAAGCACCTGCTCGGGTGATTCTGGGGCCCACTTGTCTGTAATGGTGTGCTTCAAGGT
ATCACGTCATGGGGCAGTGAACCATGTGCCCTGCCCGAAAGGCCTTCCCTGTACACCAAGGTGGTGCATTACCGG
AAGTGGATCAAGGACACCATCGTGGCCAACCCCTGA
```

Fig. 2

CDS KLK3(GC) - PSA

ATG TGG GTG CCC GTC GTG TTC CTG ACC CTC AGC GTG ACC TGG ATC GGC GCC GCC CCG
CTG ATC CTG TCC CGG ATC GTC GGG GGC TGG GAG TGC GAG AAG CAC AGC CAG CCC TGG
CAG GTG CTC GTG GCG TCC CGC GGG CGG GCC GTC TGC GGC GGG GTG CTG GTG CAC CCC
CAG TGG GTC CTG ACG GCC GCC CAC TGC ATC CGC AAC AAG AGC GTG ATC CTC CTG GGC
CGG CAC TCC CTG TTC CAC CCC GAG GAC ACC GGC CAG GTG TTC CAG GTC AGC CAC TCC
TTC CCG CAC CCC CTC TAC GAC ATC AGC CTG CTG AAG AAC CGC TTC CTC CGG CCC GGG
GAC GAC TCC AGC CAC GAC CTG ATG CTG CTC CGC CTG TCC GAG CCC GCC GAG CTG ACC
GAC GCG GTG AAG GTG ATG GAC CTC CCG ACC CAG GAG CCC GCC CTG GGC ACC ACC TGC
TAC GCC AGC GGG TGG GGC TCC ATC GAG CCC GAG GAG TTC CTG ACC CCC AAG AAG CTC
CAG TGC GTC GAC CTG CAC GTG ATC AGC AAC GAC GTG TGC GCC CAG GTC CAC CCG CAG
AAG GTG ACC AAG TTC ATG CTG TGC GCG GGG CGG TGG ACG GGC GGC AAG TCC ACC TGC
AGC GGG GAC TCC GGC GGG CCC CTC GTG TGC AAC GGC GTC CTG CAG GGC ATC ACC AGC
TGG GGG TCC GAG CCC TGC GCC CTG CCC GAG CGC CCG AGC CTC TAC ACC AAG GTG GTG
CAC TAC CGG AAG TGG ATC AAG GAC ACG ATC GTC GCC AAC CCC TGA

Fig. 3

```
RNActiveII FOLR1(GC) - PSMA

GGGAGAAAGCTTACCATGTGGAACCTGCTCCACGAGACCGACAGCGCCGTGGCGACGGCCCGGCGCCCGCGGTGG
CTGTGCGCCGGCGCCCTGGTCCTGGCCGGGGGCTTCTTCCTGCTGGGCTTCCTGTTCGGCTGGTTCATCAAGTCG
AGCAACGAGGCCACCAACATCACCCCCAAGCACAACATGAAGGCCTTCCTCGACGAGCTGAAGGCCGAGAACATC
AAGAAGTTCCTGTACAACTTCACCCAGATCCCCCACCTGGCCGGGACCGAGCAGAACTTCCAGCTGGCCAAGCAG
ATCCAGAGCCAGTGGAAGGAGTTCGGCCTGGACTCGGTGGAGCTGGCGCACTACGACGTGCTGCTCAGCTACCCC
AACAAGACCCACCCCAACTACATCAGCATCATCAACGAGGACGGCAACGAGATCTTCAACACCAGCCTGTTCGAG
CCCCCGCCCCCCGGCTACGAGAACGTGTCGGACATCGTGCCCCCCTTCAGCGCCTTCAGCCCGCAGGGCATGCCC
GAGGGGGACCTGGTGTACGTGAACTACGCCCGGACCGAGGACTTCTTCAAGCTGGAGCGCGACATGAAGATCAAC
TGCAGCGGCAAGATCGTGATCGCCCGGTACGGCAAGGTGTTCCGGGGCAACAAGGTGAAGAACGCCCAGCTGGCC
GGGGCCAAGGGCGTGATCCTGTACTCGGACCCCGCCGACTACTTCGCCCCCGGCGTGAAGAGCTACCCCGACGGC
TGGAACCTGCCCGGCGGGGGCGTCCAGCGCGGCAACATCCTCAACCTGAACGGCGCCGGCGACCCGCTGACCCCC
GGGTACCCCGCGAACGAGTACGCCTACCGGCGGGGCATCGCCGAGGCCGTGGGCCTGCCCAGCATCCCCGTGCAC
CCGATCGGCTACTACGACGCCCAGAAGCTGCTGGAGAAGATGGGCGGGAGCGCCCCGCCCGACTCGAGCTGGCGG
GGCAGCCTGAAGGTGCCCTACAACGTGGGCCCCGGCTTCACCGGGAACTTCTCGACCCAGAAGGTGAAGATGCAC
ATCCACAGCACCAACGAGGTGACCCGCATCTACAACGTGATCGGCACCCTGCGGGGCGCCGTGGAGCCCGACCGG
TACGTGATCCTCGGCGGGCACCGCGACAGCTGGGTGTTCGGCGGCATCGACCCCAGAGCGGCGCCGCCGTGGTC
CACGAGATCGTGCGGTCGTTCGGCACCCTGAAGAAGGAGGGGTGGCGGCCCCGCCGGACGATCCTGTTCGCCAGC
TGGGACGCGGAGGAGTTCGGCCTGCTGGGCAGCACCGAGTGGGCCGAGGAGAACAGCCGGCTGCTGCAGGAGCGG
GGCGTGGCCTACATCAACGCCGACTCGAGCATCGAGGGCAACTACACCCTCCGCGTGGACTGCACCCCGCTGATG
TACAGCCTGGTGCACAACCTGACCAAGGAGCTGAAGAGCCCCGACGAGGGGTTCGAGGGCAAGTCGCTGTACGAG
AGCTGGACCAAGAAGAGCCCCTCGCCCGAGTTCAGCGGCATGCCCCGGATCAGCAAGCTGGGCAGCGGGAACGAC
TTCGAGGTGTTCTTCCAGCGGCTGGGCATCGCCTCGGCCGCGCCCGGTACACCAAGAACTGGGAGACGAACAAG
TTCAGCGGCTACCCCCTCTACCACAGCGTGTACGAGACCTACGAGCTGGTGGAGAAGTTCTACGACCCCATGTTC
AAGTACCACCTGACCGTGGCCCAGGTGCGGGCGGGATGGTGTTCGAGCTGGCCAACAGCATCGTGCTGCCCTTC
GACTGCCGCGACTACGCCGTCGTGCTGCGGAAGTACGCCGACAAGATCTACTCGATCAGCATGAAGCACCCCCAG
GAGATGAAGACCTACAGCGTGAGCTTCGACTCGCTGTTCAGCGCGGTGAAGAACTTCACCGAGATCGCCAGCAAG
TTCTCGGAGCGGCTCCAGGACTTCGACAAGAGCAACCCGATCGTGCTGCGCATGATGAACGACCAGCTGATGTTC
CTGGAGCGGGCCTTCATCGACCCCCTGGGCCTGCCCGACCGGCCCTTCTACCGGCACGTGATCTACGCCCCCAGC
AGCCACAACAAGTACGCCGGCGAGTCGTTCCCGGGGATCTACGACGCCCTGTTCGACATCGAGAGCAAGGTGGAC
CCCAGCAAGGCCTGGGGCGAGGTGAAGCGCCAGATCTACGTGGCCGCCTTCACCGTGCAGGCCGCGGCCGAGACC
CTGAGCGAGGTGGCCTGACCACTAGTTATAAGACTGACTAGCCCGATGGGCCTCCCAACGGGCCCTCCTCCCCTC
CTTGCACCGAGATTAATAAAAAAAAAAAAAAAAAAAAAAAAAAAAAAAAAAAAAAAAAAAAAAAAAAAAAAAAAA
AAAAAATATTCCCCCCCCCCCCCCCCCCCCCCCCCCCCCCCTCTAGACAATTGGAATT
```

Fig. 4

```
CDS FOLH1(wt) = PSMA

ATGTGGAATCTCCTTCACGAAACCGACTCGGCTGTGGCCACCGCGCGCCGCCCGCGCTGGCTGTGCGCTGGGGCG
CTGGTGCTGGCGGGTGGCTTCTTTCTCCTCGGCTTCCTCTTCGGGTGGTTTATAAAATCCTCCAATGAAGCTACT
AACATTACTCCAAAGCATAATATGAAAGCATTTTTGGATGAATTGAAAGCTGAGAACATCAAGAAGTTCTTATAT
AATTTTACACAGATACCACATTTAGCAGGAACAGAACAAAACTTTCAGCTTGCAAAGCAAATTCAATCCCAGTGG
AAAGAATTTGGCCTGGATTCTGTTGAGCTAGCACATTATGATGTCCTGTTGTCCTACCCAAATAAGACTCATCCC
AACTACATCTCAATAATTAATGAAGATGGAAATGAGATTTTCAACACATCATTATTTGAACCACCTCCTCCAGGA
TATGAAAATGTTTCGGATATTGTACCACCTTTCAGTGCTTTCTCTCCTCAAGGAATGCCAGAGGGCGATCTAGTG
TATGTTAACTATGCACGAACTGAAGACTTCTTTAAATTGGAACGGGACATGAAAATCAATTGCTCTGGGAAAATT
GTAATTGCCAGATATGGGAAAGTTTTCAGAGGAAATAAGGTTAAAAATGCCCAGCTGGCAGGGGCAAAGGAGTC
ATTCTCTACTCCGACCCTGCTGACTACTTTGCTCCTGGGGTGAAGTCCTATCCAGATGGTTGGAATCTTCCTGGA
GGTGGTGTCCAGCGTGGAAATATCCTAAATCTGAATGGTGCAGGAGACCCTCTCACACCAGGTTACCCAGCAAAT
GAATATGCTTATAGGCGTGGAATTGCAGAGGCTGTTGGTCTTCCAAGTATTCCTGTTCATCCAATTGGATACTAT
GATGCACAGAAGCTCCTAGAAAAAATGGGTGGCTCAGCACCACCAGATAGCAGCTGGAGAGGAAGTCTCAAAGTG
CCCTACAATGTTGGACCTGGCTTTACTGGAAACTTTTCTACACAAAAAGTCAAGATGCACATCCACTCTACCAAT
GAAGTGACAAGAATTTACAATGTGATAGGTACTCTCAGAGGAGCAGTGGAACCAGACAGATATGTCATTCTGGGA
GGTCACCGGGACTCATGGGTGTTTGGTGGTATTGACCCTCAGAGTGGAGCAGCTGTTGTTCATGAAATTGTGAGG
AGCTTTGGAACACTGAAAAAGGAAGGGTGGAGACCTAGAAGAACAATTTTGTTTGCAAGCTGGGATGCAGAAGAA
TTTGGTCTTCTTGGTTCTACTGAGTGGGCAGAGGAGAATTCAAGACTCCTTCAAGAGCGTGGCGTGGCTTATATT
AATGCTGACTCATCTATAGAAGGAAACTACACTCTGAGAGTTGATTGTACACCGCTGATGTACAGCTTGGTACAC
AACCTAACAAAAGAGCTGAAAAGCCCTGATGAAGGCTTTGAAGGCAAATCTCTTTATGAAAGTTGGACTAAAAAA
AGTCCTTCCCCAGAGTTCAGTGGCATGCCCAGGATAAGCAAATTGGGATCTGGAAATGATTTTGAGGTGTTCTTC
CAACGACTTGGAATTGCTTCAGGCAGAGCACGGTATACTAAAAATTGGGAAACAAACAAATTCAGCGGCTATCCA
CTGTATCACAGTGTCTATGAAACATATGAGTTGGTGGAAAAGTTTTATGATCCAATGTTTAAATATCACCTCACT
GTGGCCCAGGTTCGAGGAGGGATGGTGTTTGAGCTAGCCAATTCCATAGTGCTCCCTTTTGATTGTCGAGATTAT
GCTGTAGTTTTAAGAAAGTATGCTGACAAAATCTACAGTATTTCTATGAAACATCCACAGGAAATGAAGACATAC
AGTGTATCATTTGATTCACTTTTTTCTGCAGTAAAGAATTTTACAGAAATTGCTTCCAAGTTCAGTGAGACTC
CAGGACTTTGACAAAAGCAACCCAATAGTATTAAGAATGATGAATGATCAACTCATGTTTCTGGAAAGAGCATTT
ATTGATCCATTAGGGTTACCAGACAGGCCTTTTTATAGGCATGTCATCTATGCTCCAAGCAGCCACAACAAGTAT
GCAGGGGAGTCATTCCCAGGAATTTATGATGCTCTGTTTGATATTGAAAGCAAAGTGGACCCTTCCAAGGCCTGG
GGAGAAGTGAAGAGACAGATTTATGTTGCAGCCTTCACAGTGCAGGCAGCTGCAGAGACTTTGAGTGAAGTAGCC
TAA
```

Fig. 5

```
CDS FOLR1(GC) = PSMA

ATG TGG AAC CTG CTC CAC GAG ACC GAC AGC GCC GTG GCC ACC GCG CGG CGC CCC CGG
TGG CTG TGC GCC GGC GCC CTG GTC CTC GCC GGG GGC TTC TTC CTG CTG GGG TTC CTC
TTC GGC TGG TTC ATC AAG TCC AGC AAC GAG GCC ACG AAC ATC ACC CCG AAG CAC AAC
ATG AAG GCG TTC CTG GAC GAG CTG AAG GCC GAG AAC ATC AAG AAG TTC CTC TAC AAC
TTC ACC CAG ATC CCC CAC CTG GCC GGG ACC GAG CAG AAC TTC CAG CTG GCC AAG CAG
ATC CAG TCC CAG TGG AAG GAG TTC GGC CTC GAC AGC GTG GAG CTG GCG CAC TAC GAC
GTG CTG CTC TCC TAC CCC AAC AAG ACG CAC CCC AAC TAC ATC AGC ATC ATC AAC GAG
GAC GGC AAC GAG ATC TTC AAC ACC TCC CTG TTC GAG CCG CCC CCC CCC GGG TAC GAG
AAC GTC AGC GAC ATC GTG CCG CCC TTC TCC GCC TTC AGC CCC CAG GGC ATG CCC GAG
GGG GAC CTG GTG TAC GTC AAC TAC GCC ACC GAG GAC TTC TTC AAG CTC GAG CGG
GAC ATG AAG ATC AAC TGC TCC GGC AAG ATC GTG ATC GCC CGC TAC GGG AAG GTG TTC
CGG GGC AAC AAG GTC AAG AAC GCC CAG CTG GCG GGC GCC AAG GGG GTG ATC CTG TAC
AGC GAC CCG GCC GAC TAC TTC GCC CCC GGC GTG AAG TCC TAC CCC GAC GGG TGG AAC
CTC CCC GGC GGC GGG GTC CAG CGC GGC AAC ATC CTG AAC CTG AAC GGG GCC GGC GAC
CCG CTC ACC CCC GGG TAC CCC GCG AAC GAG TAC GCC TAC CGG CGC GGC ATC GCC GAG
GCC GTG GGC CTG CCC AGC ATC CCG GTG CAC CCC ATC GGG TAC TAC GAC GCC CAG AAG
CTG CTC GAG AAG ATG GGC GGG TCC GCG CCC CCC GAC AGC TCC TGG CGG GGC AGC CTG
AAG GTC CCG TAC AAC GTG GGG CCC GGC TTC ACG GGC AAC TTC TCC ACC CAG AAG GTG
AAG ATG CAC ATC CAC AGC ACC AAC GAG GTC ACC CGC ATC TAC AAC GTG ATC GGG ACG
CTG CGG GGC GCC GTG GAG CCC GAC CGC TAC GTC ATC CTC GGG GGC CAC CGG GAC AGC
TGG GTG TTC GGG GGC ATC GAC CCC CAG TCC GGC GCC GCC GTG GTC CAC GAG ATC GTG
CGC AGC TTC GGG ACC CTG AAG AAG GAG GGC TGG CGG CCG CGC CGG ACC ATC CTG TTC
GCC TCC TGG GAC GCG GAG GAG TTC GGG CTC CTG GGC AGC ACC GAG TGG GCC GAG GAG
AAC TCC CGC CTG CTC CAG GAG CGG GGC GTC GCC TAC ATC AAC GCC GAC AGC TCC ATC
GAG GGG AAC TAC ACG CTG CGC GTG GAC TGC ACC CCG CTG ATG TAC AGC CTC GTG CAC
AAC CTG ACC AAG GAG CTG AAG TCC CCC GAC GAG GGC TTC GAG GGG AAG AGC CTC TAC
GAG TCC TGG ACC AAG AAG AGC CCG TCC CCC GAG TTC AGC GGC ATG CCC CGG ATC TCC
AAG CTG GGG AGC GGC AAC GAC TTC GAG GTC TTC TTC CAG CGG CTG GGC ATC GCG TCC
GGG CGC GCC CGG TAC ACG AAG AAC TGG GAG ACC AAC AAG TTC AGC GGC TAC CCC CTC
TAC CAC TCC GTG TAC GAG ACC TAC GAG CTG GTG GAG AAG TTC TAC GAC CCG ATG TTC
AAG TAC CAC CTG ACC GTC GCC CAG GTG CGC GGG GGC ATG GTG TTC GAG CTG GCC AAC
AGC ATC GTC CTC CCC TTC GAC TGC CGG GAC TAC GCC GTG GTG CTG CGC AAG TAC GCG
GAC AAG ATC TAC AGC ATC TCC ATG AAG CAC CCC CAG GAG ATG AAG ACG TAC AGC GTC
TCC TTC GAC AGC CTG TTC TCC GCC GTG AAG AAC TTC ACC GAG ATC GCC AGC AAG TTC
TCC GAG CGG CTC CAG GAC TTC GAC AAG AGC AAC CCC ATC GTG CTG CGC ATG ATG AAC
GAC CAG CTG ATG TTC CTC GAG CGG GCC TTC ATC GAC CCG CTG GGG CTG CCC GAC CGC
CCC TTC TAC CGG CAC GTC ATC TAC GCC CCC TCC AGC CAC AAC AAG TAC GCG GGC GAG
TCC TTC CCG GGG ATC TAC GAC GCC CTC TTC GAC ATC GAG AGC AAG GTG GAC CCC TCC
AAG GCC TGG GGC GAG GTG AAG CGC CAG ATC TAC GTC GCC GCC TTC ACC GTG CAG GCG
GCC GCC GAG ACC CTG AGC GAG GTG GCC TGA
```

Fig. 6

RNActiveII PSCA(GC)

GGGAGAAAGCTTACCATGAAGGCCGTGCTGCTCGCGCTGCTGATGGCCGGCCTGGCCCTGCAGCCGGGGACCGCC
CTGCTGTGCTACAGCTGCAAGGCCCAGGTCTCGAACGAGGACTGCCTGCAGGTGGAGAACTGCACGCAGCTGGGC
GAGCAGTGCTGGACCGCCCGGATCCGCGCCGTGGGCCTGCTCACCGTGATCAGCAAGGGCTGCAGCCTGAACTGC
GTGGACGACAGCCAGGACTACTACGTGGGCAAGAAGAACATCACCTGCTGCGACACCGACCTGTGCAACGCCAGC
GGCGCCCACGCCCTGCAGCCCGCGGCCGCCATCCTGGCCCTGCTGCCCGCCCTGGGCCTGCTGCTCTGGGGCCCC
GGCCAGCTGTGACCACTAGTTATAAGACTGACTAGCCCGATGGGCCTCCCAACGGGCCCTCCTCCCCTCCTTGCA
CCGAGATTAATAAAAAAAAAAAAAAAAAAAAAAAAAAAAAAAAAAAAAAAAAAAAAAAAAAAAAAAAAAAAAAAA
TATTCCCCCCCCCCCCCCCCCCCCCCCCCCCCCCCTCTAGACAATTGGAATT

Fig. 7

CDS PSCA(wt)

ATGAAGGCTGTGCTGCTTGCCCTGTTGATGGCAGGCTTGGCCCTGCAGCCAGGCACTGCCCTGCTGTGCTACTCC
TGCAAAGCCCAGGTGAGCAACGAGGACTGCCTGCAGGTGGAGAACTGCACCCAGCTGGGGGAGCAGTGCTGGACC
GCGCGCATCCGCGCAGTTGGCCTCCTGACCGTCATCAGCAAAGGCTGCAGCTTGAACTGCGTGGATGACTCACAG
GACTACTACGTGGGCAAGAAGAACATCACGTGCTGTGACACCGACTTGTGCAACGCCAGCGGGGCCCATGCCCTG
CAGCCGGCTGCTGCCATCCTTGCGCTGCTCCCTGCACTCGGCCTGCTGCTCTGGGGACCCGGCCAGCTCTAG

Fig. 8

```
CDS PSCA(GC)

ATG AAG GCC GTG CTG CTC GCC CTG CTG ATG GCG GGC CTC GCC CTG CAG CCC GGG ACC
GCC CTG CTC TGC TAC AGC TGC AAG GCC CAG GTC TCC AAC GAG GAC TGC CTG CAG GTG
GAG AAC TGC ACC CAG CTG GGC GAG CAG TGC TGG ACG GCC CGG ATC CGC GCG GTG GGG
CTC CTG ACC GTC ATC AGC AAG GGC TGC TCC CTG AAC TGC GTG GAC GAC AGC CAG GAC
TAC TAC GTG GGG AAG AAG AAC ATC ACC TGC TGC GAC ACC GAC CTC TGC AAC GCC TCC
GGC GCC CAC GCC CTG CAG CCG GCG GCC GCC ATC CTG GCC CTC CTG CCC GCC CTG GGC
CTC CTG CTG TGG GGG CCC GGC CAG CTC TGA
```

Fig. 9

RNActive II STEAP (GC) = STEAP1

GGGagaAAGCTTaccATGgagagccggaaggacatcaccaaccaggaggagctgtggaagatgaagccgcgccgg
aacctcgaggaggacgactacctgcacaaggacacgggcgagacctcgatgctgaagcggcccgtgctcctgcac
ctgcaccagaccgccacgcggacgagttcgactgcccgagcgagctccagcacacgcaggagctgttcccgcag
tggcacctgcccatcaagatcgccgccatcatcgcgagcctcaccttcctgtacaccctgctccgcgaggtcatc
caccgctggccacgtcgcaccagcagtacttctacaagatcccgatcctggtgatcaacaaggtgctcccatg
gtcagcatcaccctgctggccctcgtgtacctgccggggtgatcgcggccatcgtccagctgcacaacggcacc
aagtacaagaagttcccgcactggctcgacaagtggatgctgacgcggaagcagttcggcctgctcagcttcttc
ttcgccgtgctgcacgcgatctactcgctgagctaccccatgcggcgcagctaccggtacaagctcctgaactgg
gcctaccagcaggtgcagcagaacaaggaggacgcctggatcgagcacgacgtctggcggatggagatctacgtg
tcgctggggatcgtgggcctcgcgatcctggccctgctcgccgtcaccagcatcccgagcgtgtcggacagcctg
acctggcgcgagttccactacatccagagcaagctgggccatcgtgtcgctcctgctggggacgatccacgcgctc
atcttcgcctggaacaagtggatcgacatcaagcagttcgtctggtacaccccgccaccttcatgatcgccgtg
ttcctgccgatcgtggtcctgatcttcaagagcatcctcttcctgccgtgcctgcggaagaagatcctcaagatc
cggcacggctgggaggacgtgacgaagatcaacaagaccgagatctgcagccagctgtgaccACTAGTTATAAga
ctgactagcccgAtgggcctcccaacgggccctcctcccctccttgcaccgagAttaaTAAAAAAAAAAAAAAAA
AAAAAAAAAAAAAAAAAAAAAAAAAAAAAAAAAAAAAAAAAAAAAatattCCCCCCCCCCCCCCCCCCCCCCCC
CCCCCCCtctagaCAATTGgaatt

Fig. 10

```
CDS STEAP(wt) = STEAP1

ATGGAAAGCAGAAAAGACATCACAAACCAAGAAGAACTTTGGAAAATGAAGCCTAGGAGAAATTTAGAAGAAGAC
GATTATTTGCATAAGGACACGGGAGAGACCAGCATGCTAAAAAGACCTGTGCTTTTGCATTTGCACCAAACAGCC
CATGCTGATGAATTTGACTGCCCTTCAGAACTTCAGCACACACAGGAACTCTTTCCACAGTGGCACTTGCCAATT
AAAATAGCTGCTATTATAGCATCTCTGACTTTTCTTTACACTCTTCTGAGGGAAGTAATTCACCCTTTAGCAACT
TCCCATCAACAATATTTTTATAAAATTCCAATCCTGGTCATCAACAAAGTCTTGCCAATGGTTTCCATCACTCTC
TTGGCATTGGTTTACCTGCCAGGTGTGATAGCAGCAATTGTCCAACTTCATAATGGAACCAAGTATAAGAAGTTT
CCACATTGGTTGGATAAGTGGATGTTAACAAGAAAGCAGTTTGGGCTTCTCAGTTTCTTTTTTGCTGTACTGCAT
GCAATTTATAGTCTGTCTTACCCAATGAGGCGATCCTACAGATACAAGTTGCTAAACTGGGCATATCAACAGGTC
CAACAAAATAAAGAAGATGCCTGGATTGAGCATGATGTTTGGAGAATGGAGATTTATGTGTCTCTGGGAATTGTG
GGATTGGCAATACTGGCTCTGTTGGCTGTGACATCTATTCCATCTGTGAGTGACTCTTTGACATGGAGAGAATTT
CACTATATTCAGAGCAAGCTAGGAATTGTTTCCCTTCTACTGGGCACAATACACGCATTGATTTTTGCCTGGAAT
AAGTGGATAGATATAAAACAATTTGTATGGTATACACCTCCAACTTTTATGATAGCTGTTTTCCTTCCAATTGTT
GTCCTGATATTTAAAAGCATACTATTCCTGCCATGCTTGAGGAAGAAGATACTGAAGATTAGACATGGTTGGGAA
GACGTCACCAAAATTAACAAAACTGAGATATGTTCCCAGTTGTAG
```

Fig. 11

```
CDS STEAP(GC) = STEAP1

ATG GAG AGC CGG AAG GAC ATC ACC AAC CAG GAG GAG CTG TGG AAG ATG AAG CCC CGC
CGG AAC CTC GAG GAG GAC GAC TAC CTG CAC AAG GAC ACC GGC GAG ACG TCC ATG CTG
AAG CGC CCG GTG CTC CTG CAC CTG CAC CAG ACC GCC CAC GCC GAC GAG TTC GAC TGC
CCC AGC GAG CTC CAG CAC ACC CAG GAG CTG TTC CCC CAG TGG CAC CTG CCC ATC AAG
ATC GCG GCC ATC ATC GCC TCC CTC ACC TTC CTG TAC ACG CTG CTC CGG GAG GTC ATC
CAC CCG CTG GCC ACC AGC CAC CAG CAG TAC TTC TAC AAG ATC CCC ATC CTG GTG ATC
AAC AAG GTG CTC CCC ATG GTC TCC ATC ACC CTG CTG GCC CTC GTG TAC CTG CCC GGG
GTG ATC GCG GCC ATC GTC CAG CTG CAC AAC GGC ACC AAG TAC AAG AAG TTC CCG CAC
TGG CTC GAC AAG TGG ATG CTG ACG CGC AAG CAG TTC GGG CTG CTC AGC TTC TTC TTC
GCC GTG CTG CAC GCC ATC TAC TCC CTG AGC TAC CCC ATG CGG CGC TCC TAC CGG TAC
AAG CTC CTG AAC TGG GCG TAC CAG CAG GTG CAG CAG AAC AAG GAG GAC GCC TGG ATC
GAG CAC GAC GTC TGG CGC ATG GAG ATC TAC GTG AGC CTG GGC ATC GTG GGG CTC GCC
ATC CTG GCC CTG CTC GCC GTC ACC TCC ATC CCC AGC GTG TCC GAC AGC CTG ACC TGG
CGG GAG TTC CAC TAC ATC CAG TCC AAG CTG GGC ATC GTG AGC CTC CTG CTG GGC ACC
ATC CAC GCG CTC ATC TTC GCC TGG AAC AAG TGG ATC GAC ATC AAG CAG TTC GTC TGG
TAC ACG CCC CCG ACC TTC ATG ATC GCC GTG TTC CTG CCC ATC GTG GTC CTG ATC TTC
AAG TCC ATC CTC TTC CTG CCC TGC CTG CGC AAG AAG ATC CTC AAG ATC CGG CAC GGG
TGG GAG GAC GTG ACC AAG ATC AAC AAG ACC GAG ATC TGC AGC CAG CTG TGA
```

Fig. 12

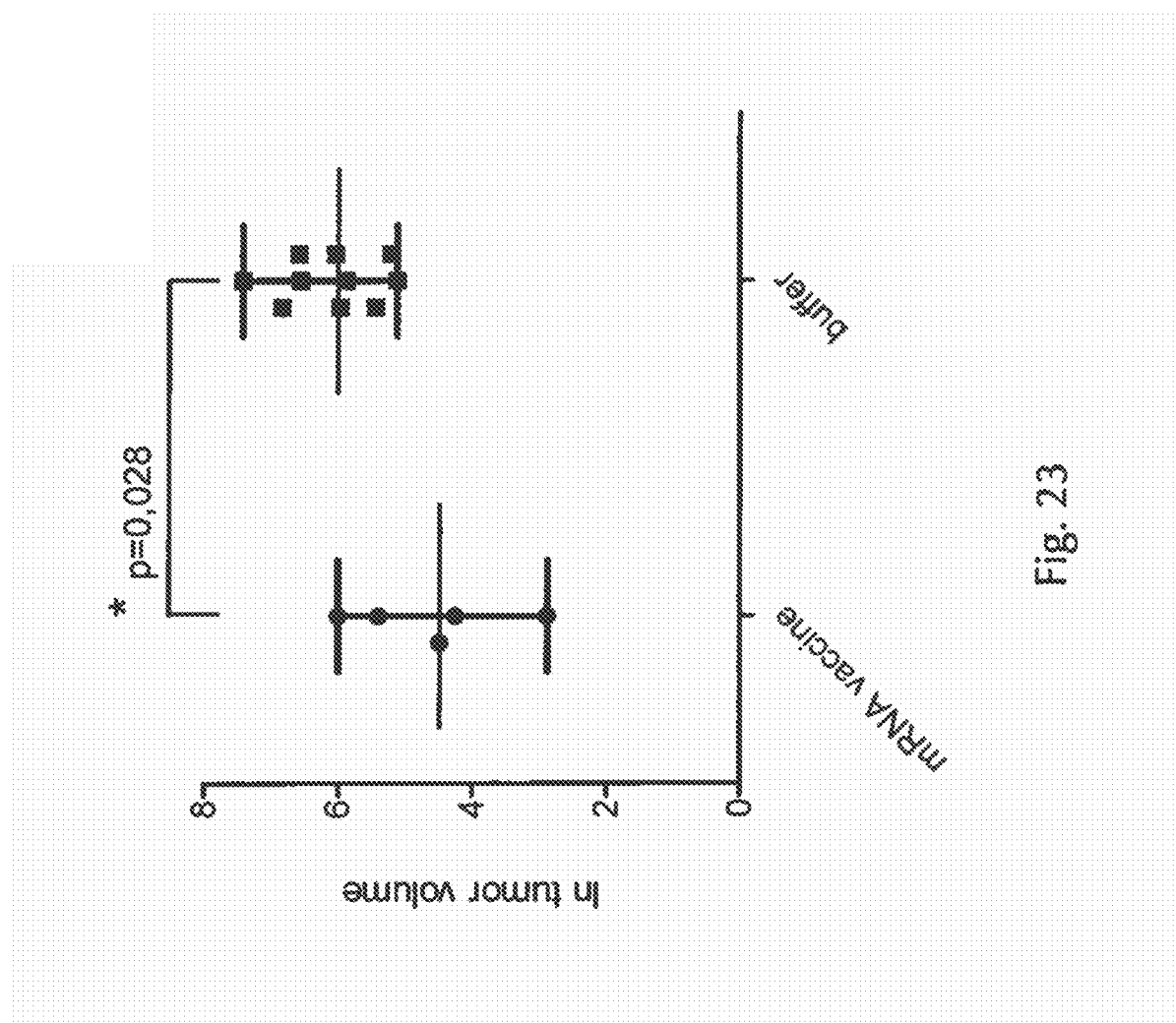

COMPOSITION FOR TREATING PROSTATE CANCER (PCA)

The present invention relates to an active (immunostimulatory) composition comprising at least one RNA, preferably an mRNA, encoding at least two (preferably different) antigens capable of eliciting an (adaptive) immune response in a mammal, wherein the antigens are selected from the group consisting of PSA (Prostate-Specific Antigen), PSMA (Prostate-Specific Membrane Antigen), PSCA (Prostate Stem Cell Antigen), and STEAP (Six Transmembrane Epithelial Antigen of the Prostate). The invention furthermore relates to a vaccine comprising said active (immunostimulatory) composition, and to the use of said active (immunostimulatory) composition (for the preparation of a vaccine) and/or of the vaccine for eliciting an (adaptive) immune response for the treatment of prostate cancer (PCa), preferably of neoadjuvant and/or hormone-refractory prostate cancers, and diseases or disorders related thereto. Finally, the invention relates to kits, particularly to kits of parts, containing the active (immunostimulatory) composition and/or the vaccine.

At present, prostate cancer is the second most commonly diagnosed cancer and the fourth leading cause of cancer-related death in men in the developed countries worldwide. Effective curative treatment modalities are debilitating, and are only currently available for localised disease. In hormone-refractory prostate cancer, no agent has been shown to prolong survival beyond approximately 1 year (see e.g. Pavlenko, M., A. K. Roos, et al. (2004). "A phase I trial of DNA vaccination with a plasmid expressing prostate-specific antigen in patients with hormone-refractory prostate cancer." Br) Cancer 91(4): 688-94.). In some highly developed western countries such as the United States of America, prostate cancer is at present even the most commonly diagnosed malignancy and the third leading cause of cancer related death among men in the United States (see e.g. Jemal, A., R. Siegel, et al. (2006). "Cancer statistics, 2006." CA Cancer J Clin 56(2): 106-30.) and in Europe, respectively (see e.g. Thomas-Kaskel, A. K., C. F. Waller, et al., (2007). "Immunotherapy with dendritic cells for prostate cancer." Int J Cancer 121(3): 467-73). Most of the diagnosed tumors are adeno-carcinomas which initially proliferate in a hormone-dependent manner. Prostate cancer is a disease in which cancer develops in the prostate, a gland in the male reproductive system. It occurs when cells of the prostate mutate and begin to multiply out of control. Typical antigens which have been shown to be overexpressed by prostate cancer cells as compared to normal counterparts are inter alia antigens like PSA, PSMA, PAP, PSCA, HER-2 and Ep-CAM. These prostate cancer cells may spread (metastasize) from the prostate to other parts of the body, especially the bones and lymph nodes. Prostate cancer may cause pain, difficulty in urinating, erectile dysfunction and other symptoms. Typically, prostate cancer develops most frequently in men over fifty, which represent the most common group of patients. However, prostate cancer remains most often undiscovered, even if determination would be possible. Determination of prostate cancer typically occurs by physical examination or by screening blood tests, such as the PSA (prostate specific antigen) test. When suspected to prostate cancer the cancer is typically confirmed by removing a piece of the prostate (biopsy) and examining it under a microscope. Further tests, such as X-rays and bone scans, may be performed to determine whether prostate cancer has spread.

Treatment of prostate cancer still remains an unsolved challenge. Conventional therapy methods may be applied for treatment of prostate cancer such as surgery, radiation therapy, hormonal therapy, occasionally chemotherapy, proton therapy, or some combination of these. However, the age and underlying health of the man as well as the extent of spread, appearance under the microscope, and response of the cancer to initial treatment are important in determining the outcome of the disease. Since prostate cancer is a disease, typically diagnosed with respect to older men, many will die of other causes before a slowly advancing prostate cancer can spread or cause symptoms. This makes treatment selection difficult. The decision whether or not to treat localized prostate cancer (a tumor that is contained within the prostate) with curative intent is a patients trade-off between the expected beneficial and harmful effects in terms of patient survival and quality of life.

However, the above therapy methods, such as surgery, radiation therapy, hormonal therapy, and chemotherapy, etc., all suffer from severe limitations. By way of example, surgical removal of the prostate, or prostatectomy, is a common treatment either for early stage prostate cancer or for cancer which has failed to respond to radiation therapy. It may cause nerve damage that significantly alters the quality of life. The most common serious complications are loss of urinary control and impotence. However, even if the prostate cancer could be removed successfully, spread of prostate cancer throughout the organism remains an unsolved problem.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. However, radiation therapy also bears high risks and often leads to a complete loss of immune defence due to destruction of the patients immune system. Furthermore, radiation therapy is typically applied locally at the site of cancer growth and thus may not avoid the above problem of spread of prostate cancer throughout the organism. If applied systemically, radiation therapy may lead to severe damages to cells and immune system.

Chemotherapy was a long time considered as a less effective sort of treatment for prostate cancers since only very few patients even respond to this sort of therapy. However, some patients (responders), having a metastasizing prostate carcinoma, may benefit from chemotherapy. The response rate is at about 20% and chemotherapy will thus play a role during treatment of the tumor relapse and failing of hormonal therapy. However, chemotherapy will typically be only palliative and does not lead to a total elimination of the prostate cancer in the patient. Typical chemotherapeutic agents include cyclophosphamid, doxorubicin, 5-fluoruracil, adriamycin, suramin and other agents, however, none of these allowed a significant longer survival of the patients. In a recent study, published 2004 in the New England Journal of Medicine, longer survival of median 2.5 months could be demonstrated for patients which received a doses of the agent docetaxel every three weeks.

Hormonal therapy typically uses medications or a combination of hormonal therapy with surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. E.g. palliative androgen deprivation therapy can induce remissions in up to 80% of the patients, but after 15-20 months, tumor cells become hormone-insensitive and androgen-independent prostate cancer develops. In this situation treatment options are rare, as chemotherapy has been of limited efficacy (see above). Hormonal therapy is therefore usually used when cancer has spread from the prostate. It may also be given to certain men undergoing radiation therapy or surgery to help prevent return of their cancer.

So for this the need for alternative treatment strategies for patients with normal and also with relapsed or advanced prostate cancer is high. As one approach, the above discussed standard therapies used for organ-confined prostate cancer, including radical prostatectomy or radiation therapy such as external (beam) irradiation and brachytherapy may under some circumstances incorporate also neoadjuvant or adjuvant hormonal therapy (see e.g. Totterman, T. H., A. Loskog, et al. (2005). "The immunotherapy of prostate and bladder cancer." BJU Int 96(5): 728-35.). While these therapies are relatively effective in the short term, a significant proportion (30-40%) of patients having initially localized disease will ultimately relapse. For metastatic prostate cancer the main therapy is androgen ablation. While this usually provides cytoreduction and palliation, progression to hormone-refractory disease typically occurs within 14-20 months. Many clinical studies have been reported in the field of chemotherapy for advanced androgen-independent prostate cancer. Only recently two trials have revealed that chemotherapy marginally improves the overall survival of patients with hormone-refractory disease.

Summarizing the above, standard techniques such as the above mentioned surgery, radiation therapy, hormonal therapy, occasionally chemotherapy, proton therapy, etc., if applied alone, do not appear to be suitable for an efficient treatment of prostate cancer (PCa). One improved way of treatment may therefore include such treatments or supplementary treatments, which can complement these standard techniques. Thus, it is suggested here to use the adaptive immune system in an approach for the treatment or supplementary treatment of prostate cancer (PCa).

As known in the art, the immune system plays an important role in the treatment and prevention of numerous diseases. According to the present stage of knowledge, various mechanisms are provided by mammalians to protect the organism by identifying and killing, e.g., tumor cells. For the purposes of the present invention, these tumor cells have to be detected and distinguished from the organism's normal (healthy) cells and tissues.

The immune systems of vertebrates such as humans consist of many types of proteins, cells, organs, and tissues, which interact in an elaborate and dynamic network. As part of this complex immune response, the vertebrate system adapts over time to recognize particular pathogens or tumor cells more efficiently. The adaptation process creates immunological memories and allows even more effective protection during future encounters. This process of adaptive or acquired immunity forms the basis for vaccination strategies.

The adaptive immune system is antigen-specific and requires the recognition of specific "self" or "non-self" antigens during a process called antigen presentation. Antigen specificity allows for the generation of responses that are tailored to specific pathogens or pathogen-infected cells or tumor cells. The ability to mount these tailored responses is maintained in the body by so called "memory cells". Should a pathogen infect the body more than once, these specific memory cells are used to quickly eliminate it. The adaptive immune system thus allows for a stronger immune response as well as for an immunological memory, where each pathogen or tumor cell is "remembered" by one or more signature antigens.

The major components of the adaptive immune system in vertebrates predominantly include lymphocytes on the cellular level and antibodies on the molecular level. Lymphocytes as cellular components of the adaptive immune system include B cells and T cells which are derived from hematopoietic stem cells in the bone marrow. B cells are involved in the humoral response, whereas T cells are involved in cell mediated immune response. Both B cells and T cells carry receptor molecules that recognize specific targets. T cells recognize a "non-self" target, such as a pathogenic target structure, only after antigens (e.g. small fragments of a pathogen) have been processed and presented in combination with a "self" receptor called a major histocompatibility complex (MHC) molecule. In contrast, the B cell antigen-specific receptor is an antibody molecule on the B cell surface, and recognizes pathogens as such when antibodies on its surface bind to a specific foreign antigen. This antigen/antibody complex is taken up by the B cell and processed by proteolysis into peptides. The B cell then displays these antigenic peptides on its surface MHC class II molecules. This combination of MHC and antigen attracts a matching helper T cell, which releases lymphokines and activates the B cell. As the activated B cell then begins to divide, its offspring secretes millions of copies of the antibody that recognizes this antigen. These antibodies circulate in blood plasma and lymph, bind to pathogens or tumor cells expressing the antigen and mark them for destruction by complement activation or for uptake and destruction by phagocytes. As a cellular component of the adaptive immune system cytotoxic T cells (CD8$^+$) may also form a CTL-response. Cytotoxic T cells (CD8$^+$) can recognize peptides from endogenous pathogens and self-antigens bound by MHC type I molecules. CD8$^+$-T cells carry out their killing function by releasing cytotoxic proteins in the cell.

Mechanisms of the immune system may thus form targets for curative treatments of various diseases. Appropriate methods are typically based on the administration of adjuvants to elicit an innate immune response or on the administration of antigens or immunogens in order to evoke an adaptive immune response. As antigens are typically based on specific components of pathogens (e.g. surface proteins) or fragments thereof, administration of nucleic acids to the patient which is followed by the expression of desired polypeptides, proteins or antigens is envisaged as well.

As an example, vaccination studies based on known prostate related antigens have been carried out in Noguchi et al. (2003) and (2004) (see e.g. Noguchi, M., K. itoh, et al. (2004). "Phase I trial of patient-oriented vaccination in HLA-A2-positive patients with metastatic hormone-refractory prostate cancer." Cancer Sci 95(1): 77-84; and Noguchi, M., K. Kobayashi, et al. (2003). "Induction of cellular and humoral immune responses to tumor cells and peptides in HLA-A24 positive hormone-refractory prostate cancer patients by peptide vaccination." Prostate 57(1): 80-92. Noguchi et al., 2003 and Noguchi et al. 2004). Noguchi et al. (2003) and (2004) carried out two phase I studies with a multipeptide trial of vaccination in metastatic hormone-resistant prostate cancer patients showing increased cellular as well as humoral immune responses to the selected targets. The vaccination strategy was safe, well tolerated with no major toxic effects. However, stabilization or reduction of prostate specific antigen (PSA) levels was also observed and only one patient showed disappearance of a bone metastasis. The main limitation of this approach that makes it difficult for clinical applications relies on the need of a priori knowledge of the patient's HLA haplotype as well as of peptide expression by prostate cancer cells.

Some other recent approaches utilize cell based vaccination strategies, e.g. the use of different antigens in vaccination strategies or the use of dendritic cells loaded with different antigens or fragments thereof. According to one example, vaccination of prostate cancer patients has been tested in clinical trials with autologous dendritic cells pulsed with recombinant human PSA (see e.g. Barrou, B., G. Benoit, et al. (2004). "Vaccination of prostatectomized prostate cancer patients in biochemical relapse, with autologous dendritic cells pulsed with recombinant human PSA." Cancer Immunol Immunother 53(5): 453-60). During vaccination of advanced prostate cancer patients with PSCA and PSA peptide-loaded dendritic cells 5 from 10 patients showed an immune response against at least one antigen (see e.g. Thomas-Kaskel, A. K., R. Zeiser, et al. (2006). "Vaccination of advanced prostate cancer patients with PSCA and PSA peptide-loaded dendritic cells induces DTH responses that correlate with superior overall survival." Int J Cancer 119(10): 2428-34.).

In another example, Murphy et al., (1996) carried out vaccination of prostate cancer patients in a corresponding phase I trial with two HLA-A*0201 PSMA epitopes to compare vaccination with peptide alone or with pulsed DCs. The results showed that more patients responded to the vaccination, if the patients were vaccinated with pulsed DCs. This study showed that vaccination with DCs loaded with peptides or proteins leads at least partially to detectable immune responses as well as a temporary PSC declines or stabilization (see e.g. Murphy, G., B. Tjoa, et al. (1996). "Phase I clinical trial: T-cell therapy for prostate cancer using autologous dendritic cells pulsed with HLA-A0201-specific peptides from prostate-specific membrane antigen." Prostate 29(6): 371-80).

Vaccination of prostate cancer patients may also be carried out with combinations of peptides loaded on dendritic cells, e.g. with peptide cocktail-loaded dendritic cells (see e.g. Fuessel, S., A. Meye, et al. (2006). "Vaccination of hormone-refractory prostate cancer patients with peptide cocktail-loaded dendritic cells: results of a phase I clinical trial." Prostate 66(8): 811-21). The cocktail contained peptides from PSA, PSMA, Survivin, Prostein and Trp-p8 (transient receptor potential p8). Clinical trials were also carried out with an dendritic cell-based multi-epitope immunotherapy of hormone-refractory prostate carcinoma (see e.g. Waeckerle-Men, Y., E. Uetz-von Allmen, et al., (2006). "Dendritic cell-based multi-epitope immunotherapy of hormone-refractory prostate carcinoma." Cancer Immunol Immunother 55(12): 1524-33). Waeckerle-Men, Y., E. Uetz-von Allmen, et al. (2006) tested vaccination of hormone-refractory prostate carcinoma with peptides from PSCA, PAP (prostatic acid phosphatase), PSMA and PSA.

While vaccination with antigenic proteins or peptides, e.g. when loaded on dendritic cells, is a common method for eliciting an immune response, immunization or vaccination may also be based on the use of nucleic acids in order to incorporate the required genetic information into the cell. In general, various methods have been developed for introducing nucleic acids into cells, such as calcium phosphate transfection, polyprene transfection, protoplast fusion, electroporation, microinjection and lipofection, lipofection having in particular proven to be a suitable method.

According to one example vaccination treatment of prostate cancer may be based on the transfection of total mRNA derived from the autologous tumor into DCs (see Heiser et al. (2002) (see e.g. Heiser, A., D. Coleman, et al., (2002). "Autologous dendritic cells transfected with prostate-specific antigen RNA stimulate CTL responses against metastatic prostate tumors." J Clin Invest 109(3): 409-17.). This strategy has the advantage of targeting multiple HLA class I and class II patient specific tumor associated antigens (TAAs) without prior HLA typing. Moreover, even stromal antigens could be targeted by this strategy since mRNA was obtained from surgical samples and not from tumor cell lines. As an example, Heiser et al. developed a DC-based immunotherapy protocol in which DCs were transfected with mRNA encoding PSA. The vaccination was well tolerated and induced an increased T cell response to PSA. However, such DC-based anti prostate cancer vaccines appear to generate a strong T cell response, which may be accompanied by clinical response though the frequency of the latter still remains unsatisfactory DNA may also be utilized as a nucleic acid in vaccination strategies in order to incorporate the required genetic information into the cell. According to a specific example, DNA viruses may be used as a DNA vehicle. Because of their infectious properties, such viruses achieve a very high transfection rate. The viruses used are genetically modified in such a manner that no functional infectious particles are formed in the transfected cell. E.g., phase I trials were carried out in a study of Eder et al. (2000) using recombinant vaccinia viruses expressing PSA. The authors demonstrated T cell immune responses to PSA and also serum PSA stabilizations in selected patients. (see e.g. Eder, J. P., P. W. Kantoff, et al. (2000). "A phase I trial of a recombinant vaccinia virus expressing prostate-specific antigen in advanced prostate cancer." Clin Cancer Res 6(5): 1632-8.). The inflammatory response triggered by the highly immunogenic peptides from the recombinant virus may enhance the immunogenicity of the foreign protein but it was shown that the immune system reduces the replication of the recombinant virus and thereby limits the clinical outcome. Even though recombinant vaccines have shown immunogenicity and evidence for a tumor response was shown in several trials, these results, however, need to be substantiated.

According to a further approach, vaccination of hormone-refractory prostate cancer patients was carried out with DNA plasmids expressing PSA (see e.g. Pavlenko, M., A. K. Roos, et al. (2004). "A phase I trial of DNA vaccination with a plasmid expressing prostate-specific antigen in patients with hormone-refractory prostate cancer." Br J Cancer 91(4): 688-94). Garcia-Hernandez et al., (2007) showed that therapeutic and prophylactic vaccination with a plasmid or a virus-like replicon coding for STEAP (Six Transmembrane Epithelial Antigen of the Prostate) prolonged the survival in tumor-challenged mice (see e.g. Garcia-Hernandez Mde, L., A. Gray, et al. (2007). "In vivo effects of vaccination with six-transmembrane epithelial antigen of the prostate: a candidate antigen for treating prostate cancer." Cancer Res 67(3): 1344-51). Recently STEAP was identified as indicator protein for advanced human prostate cancer, which is highly overexpressed in human prostate cancer. Its function is currently unknown.

While using DNA as a carrier of genetic information, it is, however, not possible to rule out the risk of uncontrolled propagation of the introduced gene or of viral genes, for example due to potential recombination events. This also entails the risk of the DNA being inserted into an intact gene of the host cell's genome by e.g. recombination, with the consequence that this gene may be mutated and thus completely or partially inactivated or the gene may give rise to misinformation. In other words, synthesis of a gene product which is vital to the cell may be completely suppressed or alternatively a modified or incorrect gene product is expressed. One particular risk occurs if the DNA is integrated into a gene which is involved in the regulation of cell growth.

In this case, the host cell may become degenerate and lead to cancer or tumor formation. Furthermore, if the DNA introduced into the cell is to be expressed, it is necessary for the corresponding DNA vehicle to contain a strong promoter, such as the viral CMV promoter. The integration of such promoters into the genome of the treated cell may result in unwanted alterations of the regulation of gene expression in the cell. Another risk of using DNA as an agent to induce an immune response (e.g. as a vaccine) is the induction of pathogenic anti-DNA antibodies in the patient into whom the foreign DNA has been introduced, so bringing about a (possibly fatal) immune response.

Summarizing the results of the above approaches it is doubtless that some improvement is achieved for the treatment of prostate cancer (PCa), even though there is still—given the high mortality rates—a strong need for further, alternative or improved ways of treatment.

Thus overall, there is room and a need for an efficient system, which may be used to effectively stimulate the immune system to allow treatment of prostate cancer (PCa), while avoiding the problems of uncontrolled propagation of an introduced gene due to DNA based compositions.

It is thus an object of the present invention to provide a composition, which a) allows treatment of prostate cancer (PCa) by stimulating the immune system, while b) avoiding the above mentioned disadvantages.

This object is solved by the subject matter of the present invention, particularly by an active (immunostimulatory) composition comprising at least one RNA, encoding at least two, three or even four (preferably different) antigens selected from the group comprising the following antigens:
  PSA (Prostate-Specific Antigen)=KLK3 (Kallikrein-3),
  PSMA (Prostate-Specific Membrane Antigen),
  PSCA (Prostate Stem Cell Antigen),
  STEAP (Six Transmembrane Epithelial Antigen of the Prostate).

Surprisingly, it has been found that a specific combination of at least two antigens, antigenic proteins or antigenic peptides of the afore mentioned group, preferably of two, three or four of these antigens, antigenic proteins or antigenic peptides, as contained in an active (immunostimulatory) composition according to the present invention, is capable to effectively stimulate the (adaptive) immune system to allow treatment of prostate cancer (PCa), preferably of neoadjuvant and/or hormone-refractory prostate cancers, and diseases or disorders related thereto. Herein, the terms antigens, antigenic proteins or antigenic peptides may be used synomously. In the context of the present invention, an inventive active (immunostimulatory) composition shall be further understood as a composition, which is able to elicit an immune response, preferably an adaptive immune response as defined herein, due to one of the component(s) contained or encoded by the components of the active (immunostimulatory) composition, preferably by the at least one RNA, preferably (m)RNA, encoding the at least two (preferably different) antigens.

Antigens like PSA, PSMA and PSCA have been shown to be overexpressed by prostate cancer cells as compared to normal counterparts. These antigens therefore represent possible targets of immunotherapy (see e.g. Marrari, A., M. Iero, et al. (2007). "Vaccination therapy in prostate cancer." Cancer Immunol Immunother 56(4): 429-45.)

The at least one RNA of the active (immunostimulatory) composition may be PSA. In the context of this invention "PSA" is "Prostate-specific antigen" and may be synomously named KLK3 (Kallikrein-3) in the literature. Prostate-specific antigen (PSA) is a 33 kDa protein and an androgen-regulated kallikrein-like, serine protease that is produced exclusively by the epithelial cells of all types of prostatic tissue, benign and malignant. Particularly, PSA is highly expressed by normal prostatic epithelial cells and represents one of the most characterized tumor associated antigens in prostate cancer. Physiologically, it is present in the seminal fluid at high concentration and functions to cleave the high molecular weight protein responsible for the seminal coagulum into smaller polypeptides. This action results in liquefaction of the coagulum. PSA is also present in the serum and can be measured reliably by either a monoclonal immunoradiometric assay or a polyclonal radioimmunoassay. PSA is the most widely used tumor marker for screening, diagnosing, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not recognized as a disease-specific marker, as elevated levels of PSA are detectable in a large percentage of patients with BPH and prostatitis (25-86%) (Gao et al., 1997, Prostate 31: 264-281), as well as in other nonmalignant disorders and in some normal men, a factor which significantly limits the diagnostic specificity of this marker. In the context of this invention the preferred sequence of the at least one RNA, preferably of the mRNA, encoding PSA (prostate specific antigen)—if being used in the active (immunostimulatory) composition according to the invention—contains or comprises a sequence as deposited under accession number NM_001648, more preferably, it contains or comprises a sequence as shown in FIG. 1 (SEQ ID NO: 1), and—even more preferably—the at least one RNA, if encoding PSA (prostate specific antigen), contains or comprises a coding sequence as shown in any of FIG. 2 or 3 (SEQ ID NOs: 2 or 3). According to a further preferred embodiment, the at least one RNA of the active (immunostimulatory) composition may alternatively or additionally encode a PSA antigen sequence selected from a fragment, a variant or an epitope of a PSA sequence as deposited under accession number NM_001648 or as shown in any of FIG. 1, 2 or 3 (SEQ ID NOs: 1, 2 or 3).

The at least one RNA of the active (immunostimulatory) composition may be PSMA. In the context of this invention "PSMA" is "Prostate-specific membrane antigen" and may be synomously named FOLH1 (Folate hydrolase 1) or "PSM". PSMA is a 100 kDa type II transmembrane glycoprotein, wherein PSMA expression is largely restricted to prostate tissues, but detectable levels of PSMA mRNA have been observed in brain, salivary gland, small intestine, and renal cell carcinoma (Israeli et al., 1993, Cancer Res 53: 227-230). PSMA is highly expressed in most primary and metastatic prostate cancers, but is also expressed in most normal intraepithelial neoplasia specimens (Gao et al. (1997), supra). Particularly, PSMA is highly expressed in prostate cancer cells and nonprostatic solid tumor neovasculature and is a target for anticancer imaging and therapeutic agents. PSMA acts as a glutamate carboxypeptidase (GCPII) on small molecule substrates, including folate, the anticancer drug methotrexate, and the neuropeptide N-acetyl-L-aspartyl-L-glutamate. In prostate cancer, PSMA expression has been shown to correlate with disease progression, with highest levels expressed in hormone-refractory and metastatic disease. The cellular localization of PSMA is cytoplasmic and/or membranous. PSMA is considered a biomarker for prostate cancer (PCa) and is under intense investigation for use as an imaging and therapeutic target. In the context of this invention the preferred sequence of the at least one RNA, preferably of the mRNA, encoding PSMA (prostate specific membrane antigen)—if being used in the active (immunostimulatory) composition according to the invention—contains or comprises a sequence as deposited under accession number NM_004476, more preferably, it contains or comprises a sequence as shown in FIG. 4 (SEQ ID NO: 4), and—even more preferably—the at least one RNA, if encoding PSMA (prostate specific antigen), contains or comprises a coding sequence as shown in any of FIG. 5 or 6 (SEQ ID NO: 5 or 6). According to a further preferred embodiment, the at least one RNA of the active (immunostimulatory) composition may alternatively or additionally encode a PSMA antigen sequence selected from a fragment, a variant or an epitope of a PSMA sequence as deposited under accession number NM_004476 or as shown in any of FIG. 5 or 6 (SEQ NOs: 5 or 6).

The at least one RNA of the active (immunostimulatory) composition may be PSCA. In the context of this invention "PSCA" is "prostate stem cell antigen". PSCA is widely over-expressed across all stages of prostate cancer, including high grade prostatic intraepithelial neoplasia (PIN), androgen-dependent and androgen-independent prostate tumors. The PSCA gene shows 30% homology to stem cell antigen-2, a member of the Thy-1/Ly-6 family of glycosylphosphatidylinositol (GPI)-anchored cell surface antigens, and encodes a 123 amino acid protein with an amino-terminal signal sequence, a carboxy-terminal GPI-anchoring sequence, and multiple N-glycosylation sites. PSCA mRNA expression is highly upregulated in both androgen dependent and androgen independent prostate cancer xenografts. In situ mRNA analysis localizes PSCA expression to the basal cell epithelium, the putative stem cell compartment of the prostate. Flow cytometric analysis demonstrates that PSCA is expressed predominantly on the cell surface and is anchored by a GPI linkage. Fluorescent in situ hybridization analysis localizes the PSCA gene to chromosome 8q24. 2, a region of allelic gain in more than 80% of prostate cancers. PSCA may be used as a prostate cancer marker to discriminate between malignant prostate cancers, normal prostate glands and non-malignant neoplasias. For example, PSCA is expressed at very high levels in prostate cancer in relation to benign prostatic hyperplasia (BPH). In the context of this invention the preferred sequence of the at least one RNA, preferably of the mRNA, encoding PSCA (prostate stem cell antigen)—if being used in the active (immunostimulatory) composition according to the invention—contains or comprises a sequence as deposited under accession number NM_005672, more preferably, it contains or comprises a sequence as shown in FIG. 7 (SEQ ID NO: 7), and—even more preferably—the at least one RNA, if encoding PSCA (prostate stem cell antigen), contains or comprises a coding sequence as shown in any of FIG. 8 or 9 (SEQ ID NOs: 8 or 9). According to a further preferred embodiment, the at least one RNA of the active (immunostimulatory) composition may alternatively or additionally encode a PSCA antigen sequence selected from a fragment, a variant or an epitope of a PSCA sequence as deposited under accession number NM_005672 or as shown in any of FIG. 8 or 9 (SEQ ID NOs: 8 or 9).

The at least one RNA of the active (immunostimulatory) composition may be STEAP. In the context of this invention "STEAP" is six transmembrane epithelial antigen of the prostate and may be synomously named STEAP1. STEAP or STEAP-1 is a novel cell surface protein and is expressed predominantly in human prostate tissue and in other common malignancies including prostate, bladder, colon, and ovarian carcinomas, and in Ewing's sarcoma, suggesting that it could function as an almost universal tumor antigen. Particularly, STEAP is highly expressed in primary prostate cancer, with restricted expression in normal tissues. STEAP positivity in marrow samples was highly correlated with survival with new metastasis in Kaplan Meier analysis (p=0.001). In the context of this invention the preferred sequence of the at least one RNA, preferably of the mRNA, encoding STEAP (six transmembrane epithelial antigen of the prostate) (or STEAP1)—if being used in the active (immunostimulatory) composition according to the invention—contains or comprises a sequence as deposited under accession number NM_012449, more preferably, it contains or comprises a sequence as shown in FIG. 10 (SEQ ID NO: 10), and—even more preferably—the at least one RNA, if encoding STEAP (six transmembrane epithelial antigen of the prostate), contains or comprises a coding sequence as shown in any of FIG. 11 or 12 (SEQ ID NO: 11 or 12). According to a further preferred embodiment, the at least one RNA of the active (immunostimulatory) composition may alternatively or additionally encode a STEAP antigen sequence selected from a fragment, a variant or an epitope of a STEAP sequence as deposited under accession number NM_012449 or as shown in any of FIG. 11 or 12 (SEQ ID NOs: 11 or 12).

Antigens, antigenic proteins or antigenic peptides as defined above which may be encoded by the at least one RNA of the active (immunostimulatory) composition according to the present invention, may comprise fragments or variants of those sequences. Such fragments or variants may typically comprise a sequence having a sequence homology with one of the above mentioned antigens, antigenic proteins or antigenic peptides or sequences or their encoding nucleic acid sequences of at least 5%, 10%, 20%, 30%, 40%, 50%, 60%, preferably at least 70%, more preferably at least 80%, equally more preferably at least 85%, even more preferably at least 90% and most preferably at least 95% or even 97%, to the entire wild-type sequence, either on nucleic acid level or on amino acid level.

"Fragments" of antigens, antigenic proteins or antigenic peptides in the context of the present invention may comprise a sequence of an antigen, antigenic protein or antigenic peptide as defined above, which is, with regard to its amino acid sequence (or its encoded nucleic acid sequence), N-terminally, C-terminally and/or intrasequentially truncated compared to the amino acid sequence of the original (native) protein (or its encoded nucleic acid sequence). Such truncation may thus occur either on the amino acid level or correspondingly on the nucleic acid level. A sequence homology with respect to such a fragment as defined above may therefore preferably refer to the entire antigen, antigenic protein or antigenic peptide as defined above or to the entire (coding) nucleic acid sequence of such an antigen, antigenic protein or antigenic peptide.

Fragments of antigens, antigenic proteins or antigenic peptides in the context of the present invention may furthermore comprise a sequence of an antigen, antigenic protein or antigenic peptide as defined above, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form.

Fragments of antigens, antigenic proteins or antigenic peptides as defined herein may also comprise epitopes of those antigens, antigenic proteins or antigenic peptides. Epitopes (also called "antigen determinants") in the context of the present invention are typically fragments located on the outer surface of (native) antigens, antigenic proteins or antigenic peptides as defined herein, preferably having 5 to 15 amino acids, more preferably having 5 to 12 amino acids, even more preferably having 6 to 9 amino acids, which may be recognized by antibodies or B-cell receptors, i.e. in their native form. Such epitopes of antigens, antigenic proteins or antigenic peptides may furthermore be selected from any of the herein mentioned variants of such antigens, antigenic proteins or antigenic peptides. In this context antigenic determinants can be conformational or discontinous epitopes which are composed of segments of the antigens, antigenic proteins or antigenic peptides as defined herein that are discontinuous in the amino acid sequence of the antigens, antigenic proteins or antigenic peptides as defined herein but are brought together in the three-dimensional structure or continuous or linear epitopes which are composed of a single polypeptide chain.

"Variants" of antigens, antigenic proteins or antigenic peptides as defined above may be encoded by the at least one RNA of the active (immunostimulatory) composition according to the present invention, wherein nucleic acids of the at least one (m)RNA, encoding the antigen, antigenic protein or antigenic peptide as defined above, are exchanged. Thereby, an antigen, antigenic protein or antigenic peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native antigen or antigenic protein, e.g. its specific antigenic property.

The at least one RNA of the active (immunostimulatory) composition according to the present invention may also encode an antigen or an antigenic protein as defined above, wherein the encoded amino acid sequence comprises conservative amino acid substitution(s) compared to its physiological sequence. Those encoded amino acid sequences as well as their encoding nucleotide sequences in particular fall under the term variants as defined above. Substitutions in which amino acids which originate from the same class are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of antigens, antigenic proteins or antigenic peptides as defined above, which may be encoded by the at least one RNA of the active (immunostimulatory) composition according to the present invention, may also comprise those sequences, wherein nucleic acids of the at least one (m)RNA are exchanged according to the degeneration of the genetic code, without leading to an alteration of respective amino acid sequence of the antigen, antigenic protein or antigenic peptide, i.e. the amino acid sequence or at least part thereof may not differ from the original sequence in one or more mutation(s) within the above meaning.

In order to determine the percentage to which two sequences (nucleic acid sequences, e.g. RNA or mRNA sequences as defined herein, or amino acid sequences, preferably their encoded amino acid sequences, e.g. the amino acid sequences of the antigens, antigenic proteins or antigenic peptides as defined above) are identical, the sequences can be aligned in order to be subsequently compared to one another. Therefore, e.g. gaps can be inserted into the sequence of the first sequence and the component at the corresponding position of the second sequence can be compared. If a position in the first sequence is occupied by the same component as is the case at a position in the second sequence, the two sequences are identical at this position. The percentage to which two sequences are identical is a function of the number of identical positions divided by the total number of positions. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The active (immunostimulatory) composition according to the present invention comprises, as defined above, at least one RNA, encoding least two (preferably different) antigens selected from any of the antigens of the above group, since according to the invention a specific combination of at least two (preferably different) antigens of the afore mentioned group is capable to effectively stimulate the (adaptive) immune system to allow treatment of prostate cancer (PCa). However, the present invention may also provide such active (immunostimulatory) compositions, comprising at least one RNA, encoding three or four (preferably different) antigens selected from any of the antigens of the above group, wherein any combination of these antigens is possible and encompassed by the present invention.

More preferably, the present invention may also provide an active (immunostimulatory) composition, comprising at least one RNA, encoding at least three or four (preferably different) antigens selected from any of the antigens of the above group, wherein any combination of these antigens is possible.

Accordingly, due to another particularly preferred embodiment, the at least one RNA of the active (immunostimulatory) composition of the present invention, may encode at least two (preferably different) antigens selected from any of the antigens of the above mentioned group comprising (at least) any one of the following combinations of antigens:

PSA and PSMA, or
PSA and PSCA, or
PSA and STEAP, or
PSMA and PSCA, or
PSMA and STEAP, or
PSCA and STEAP,
or
PSA, PSMA and PSCA, or
PSA, PSMA and STEAP, or PSMA, PSCA and STEAP, or
PSA, PSCA and STEAP, or
or
PSA, PSMA, PSCA and STEAP.

According to a further preferred embodiment, the present invention provides an active (immunostimulatory) composition comprising at least one RNA, encoding at least two, three or four (preferably different) antigens,
a) wherein at least one antigen is selected from:
   STEAP (Six Transmembrane Epithelial Antigen of the Prostate); and
b) wherein the further antigen(s) is (are) selected from at least one antigen of any of the following specific antigens or combinations thereof:
   PSA (Prostate-Specific Antigen), or
   PSMA (Prostate-Specific Membrane Antigen), or
   PSCA (Prostate Stem Cell Antigen);
   or
   PSA and PSMA, or
   PSA and PSCA, or
   PSMA and PSCA;
   or
   PSA, PSMA and PSCA.

According to an even more preferred embodiment the present invention provides an active (immunostimulatory) composition comprising at least one RNA, encoding four (preferably different) antigens selected from PSA, PSMA, PSCA and STEAP.

The at least one RNA of the active (immunostimulatory) composition according to the present invention is typically any RNA, preferably, without being limited thereto, a coding RNA, a circular or linear RNA, a single- or a double-stranded RNA (which may also be regarded as a RNA due to non-covalent association of two single-stranded RNA) or a partially double-stranded or partially single stranded RNA, which are at least partially self complementary (both of these partially double-stranded or partially single stranded RNA molecules are typically formed by a longer and a shorter single-stranded RNA molecule or by two single stranded RNA-molecules, which are about equal in length, wherein one single-stranded RNA molecule is in part complementary to the other single-stranded RNA molecule and both thus form a double-stranded RNA in this region, i.e. a partially double-stranded or partially single stranded RNA with respect to the entire RNA sequence). More preferably, the at least one RNA of the active (immunostimulatory) composition according to the present invention is a single-stranded RNA, even more preferably a linear RNA. Most preferably, the at least RNA of the active (immunostimulatory) composition according to the present invention is a messenger RNA (mRNA). In this context, a messenger RNA (mRNA) is typically a RNA, which is composed of (at least) several structural elements, e.g. an optional 5'-UTR region, an upstream positioned ribosomal binding site followed by a coding region, an optional 3'-UTR region, which may be followed by a poly-A tail (and/or a poly-C-tail).

Due to one particularly preferred embodiment, each of the at least two (preferably different) antigens of the active (immunostimulatory) composition of the present invention, may be encoded by one (monocistronic) RNA, preferably one (monocistronic) mRNA. In other words, the active (immunostimulatory) composition of the present invention may contain at least two (monocistronic) RNAs, preferably mRNAs, wherein each of these two (monocistronic) RNAs, preferably mRNAs, may encode just one (preferably different) antigen, selected from one of the above mentioned groups or subgroups, preferably in one of the above mentioned combinations.

According to another particularly preferred embodiment, the active (immunostimulatory) composition of the present invention, may comprise (at least) one bi- or even multicistronic RNA, preferably mRNA, i.e. (at least) one RNA which carries two or even more of the coding sequences of at the least two (preferably different) antigens, selected from one of the above mentioned groups or subgroups, preferably in one of the above mentioned combinations. Such coding sequences of the at least two (preferably different) antigens of the (at least) one bi- or even multicistronic RNA may be separated by at least one IRES (internal ribosomal entry site) sequence, as defined below. Thus, the term "encoding at least two (preferably different) antigens" may mean, without being limited thereto, that the (at least) one (bi- or even multicistronic) RNA, preferably a mRNA, may encode e.g. at least two, three or four (preferably different) antigens of the above mentioned group(s) of antigens or their fragments or variants within the above definitions. More preferably, without being limited thereto, the (at least) one (bi- or even multicistronic) RNA, preferably mRNA, may encode e.g. at least two, three or four (preferably different) antigens of the above mentioned subgroup(s) of antigens or their fragments or variants within the above definitions. In this context, a so-called IRES (internal ribosomal entry site) sequence as defined above can function as a sole ribosome binding site, but it can also serve to provide a bi- or even multicistronic RNA as defined above which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a further particularly preferred embodiment, the active (immunostimulatory) composition of the present invention, may comprise a mixture of at least one monocistronic RNA, preferably mRNA, as defined above, and at least one bi- or even multicistronic RNA, preferably mRNA, as defined above. The at least one monocistronic RNA and/or the at least one bi- or even multicistronic RNA preferably encode different antigens or their fragments or variants within the above definitions, the antigens preferably being selected from one of the above mentioned groups or subgroups of antigens, more preferably in one of the above mentioned combinations. However, the at least one monocistronic RNA and the at least one bi- or even multicistronic RNA may preferably also encode (in part) identical antigens selected from one of the above mentioned groups or subgroups of antigens, preferably in one of the above mentioned combinations, provided that the active (immunostimulatory) composition of the present invention as a whole provides at least two (preferably different) antigens as defined above. Such an embodiment may be advantageous e.g. for a staggered, e.g. time dependent, administration of the active (immunostimulatory) composition of the present invention to a patient in need thereof. The components of such an active (immunostimulatory) composition of the present invention, particularly the different RNAs encoding the at least two (preferably different) antigens, may be e.g. contained in (different parts of) a kit of parts composition or may be e.g. administered separately as components of different active (immunostimulatory) compositions according to the present invention.

Preferably, the at least one RNA of the active (immunostimulatory) composition, encoding at least two (preferably different) antigens selected from the above defined group of antigens, more preferably in the above combinations, typically comprises a length of about 50 to about 20000, or 100 to about 20000 nucleotides, preferably of about 250 to about 20000 nucleotides, more preferably of about 500 to about 10000, even more preferably of about 500 to about 5000.

According to one embodiment, the at least one RNA of the active (immunostimulatory) composition, encoding at least two (preferably different) antigens selected from the above defined group(s) or subgroup(s) of antigens, more preferably in the above combinations, may be in the form of a modified RNA, wherein any modification, as defined herein, may be introduced into the at least one RNA of the active (immunostimulatory) composition. Modifications as defined herein preferably lead to a stabilized at least one RNA of the active (immunostimulatory) composition of the present invention.

According to a first embodiment, the at least one RNA of the active (immunostimulatory) composition of the present invention may thus be provided as a "stabilized RNA", preferably a stabilized mRNA, that is to say as an (m)RNA that is essentially resistant to in vivo degradation (e.g. by an exo- or endo-nuclease). Such stabilization can be effected, for example, by a modified phosphate backbone of the at least one (m)RNA of the active (immunostimulatory) composition of the present invention. A backbone modification in connection with the present invention is a modification in which phosphates of the backbone of the nucleotides contained in the RNA are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized (m)RNAs may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-O-(1-thiophosphate)).

The at least one RNA of the active (immunostimulatory) composition of the present invention may additionally or alternatively also contain sugar modifications. A sugar modification in connection with the present invention is a chemical modification of the sugar of the nucleotides of the at least one RNA and typically includes, without implying any limitation, sugar modifications selected from the group consisting of 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), or azidotriphosphate (2'-azido-2'-deoxycytidine-5'-triphosphate, 2'-azido-2'-deoxyuridine-5'-triphosphate).

The at least one RNA of the active (immunostimulatory) composition of the present invention may additionally or alternatively also contain at least one base modification, which is preferably suitable for increasing the expression of the protein coded for by the at least one RNA sequence significantly as compared with the unaltered, i.e. natural (=native), RNA sequence. Significant in this case means an increase in the expression of the protein compared with the expression of the native RNA sequence by at least 20%, preferably at least 30%, 40%, 50% or 60%, more preferably by at least 70%, 80%, 90% or even 100% and most preferably by at least 150%, 200% or even 300% or more. In connection with the present invention, a nucleotide having such a base modification is preferably selected from the group of the base-modified nucleotides consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to another embodiment, the at least one RNA of the active (immunostimulatory) composition of the present invention can likewise be modified (and preferably stabilized) by introducing further modified nucleotides containing modifications of their ribose or base moieties. Generally, the at least one (m)RNA of the active (immunostimulatory) composition of the present invention may contain any native (=naturally occurring) nucleotide, e.g. guanosine, uracil, adenosine, and/or cytosine or an analogue thereof. In this connection, nucleotide analogues are defined as non-natively occurring variants of naturally occurring nucleotides. Accordingly, analogues are chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the RNA sequence. Analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'- deoxyguanosine, 2'-Fluoro-2'-deoxyuridine, 2'-Fluorothymidine, 2-methyl-adenosine, 2-methyl-guanosine, 2-methyl-thio-N-6-isopenenyl-adenosine, 2'-O-Methyl-2'-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetylcytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymethylaminomethyl-2-thio-uracil, 5-carboxymethylamonomethyl-uracil, 5-Chloro-Ara-cytosine, 5-Fluoro-uridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methylguanosine, 8-Azaadenosine, 8-Bromo-adenosine, 8-Bromo-guanosine, 8-Mercapto-guanosine, 8-Oxoguanosine, Benz-imidazole-riboside, Beta-D-mannosyl-queosine, Dihydrouracil, Inosine, N1-Methyladenosine, N6-[(6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642. In the case of an analogue as described above, particular preference may be given according to the invention to those analogues that increase the immunogenity of the RNA of the inventive active (immunostimulatory) composition and/or do not interfere with a further modification of the RNA that has been introduced.

According to a particular embodiment, the at least one RNA of the active (immunostimulatory) composition of the present invention can contain a lipid modification. Such a lipid-modified RNA typically comprises an RNA as defined herein, encoding at least two antigens selected from the group of antigens as defined above, preferably in the above combinations. Such a lipid-modified RNA typically further comprises at least one linker covalently linked with that RNA, and at least one lipid covalently linked with the respective linker. Alternatively, the lipid-modified RNA comprises an (at least one) RNA as defined herein and at least one (bifunctional) lipid covalently linked (without a linker) with that RNA. According to a third alternative, the lipid-modified RNA comprises an RNA as defined herein, at least one linker covalently linked with that RNA, and at least one lipid covalently linked with the respective linker, and also at least one (bifunctional) lipid covalently linked (without a linker) with that RNA.

The lipid contained in the at least one RNA of the inventive active (immunostimulatory) composition (complexed or covalently bound thereto) is typically a lipid or a lipophilic residue that preferably is itself biologically active. Such lipids preferably include natural substances or compounds such as, for example, vitamins, e.g. alpha-tocopherol (vitamin E), including RRR-alpha-tocopherol (formerly D-alpha-tocopherol), L-alpha-tocopherol, the racemate D,L-alpha-tocopherol, vitamin E succinate (VES), or vitamin A and its derivatives, e.g. retinoic acid, retinol, vitamin D and its derivatives, e.g. vitamin D and also the ergosterol precursors thereof, vitamin E and its derivatives, vitamin K and its derivatives, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues within the scope of the present invention include, without implying any limitation, polyalkylene glycols (Oberhauser et al., Nucl. Acids Res., 1992, 20, 533), aliphatic groups such as, for example, $C_1$-$C_{20}$-alkanes, $C_1$-$C_2$-alkenes or $C_1$-$C_{20}$-alkanol compounds, etc., such as, for example, dodecanediol, hexadecanol or undecyl residues (Saison-Behmoaras et al, EMBO), 1991, 10, 111; Kabanov et al., FEBS Lett., 1990, 259, 327; Svinarchuk et al., Biochimie, 1993, 75, 49), phospholipids such as, for example, phosphatidylglycerol, diacylphosphatidylglycerol, phosphatidylcholine, dipalmitoylphosphatidykholine, distearoylphosphatidylcholine, phosphatidylserine, phosphatidylethanolamine, di-hexadecyl-rac-glycerol, sphingolipids, cerebrosides, gangliosides, or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), polyamines or polyalkylene glycols, such as, for example, polyethylene glycol (PEG) (Manoharan et al., Nucleosides & Nucleotides, 1995, 14, 969), hexaethylene glycol (HEG), palmitin or palmityl residues (Mishra et al., Biochim. Biophys. Ada, 1995, 1264, 229), octadecylamines or hexylamino-carbonyl-oxycholesterol residues (Crooke et al., J. Pharmacol. Exp. Ther., 1996, 277, 923), and also waxes, terpenes, alicyclic hydrocarbons, saturated and mono- or poly-unsaturated fatty acid residues, etc.

The at least one RNA of the active (immunostimulatory) composition of the present invention may likewise be stabilized in order to prevent degradation of the RNA in vivo by various approaches. It is known in the art that instability and (fast) degradation of mRNA or of RNA in vivo in general may represent a serious problem in the application of RNA based compositions. This instability of RNA is typically due to RNA-degrading enzymes, "RNases" (ribonucleases), wherein contamination with such ribonucleases may sometimes completely degrade RNA in solution. Accordingly, the natural degradation of mRNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance for a mRNA in vivo. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

The at least one RNA of the active (immunostimulatory) composition of the present invention, particularly if provided as an mRNA, can therefore be stabilized against degradation by RNases by the addition of a so-called "5' cap" structure. Particular preference is given in this connection to an m7G (5')ppp (5'(A,G(5')ppp(5')A or G(5')ppp(5')G as the "5' cap" structure. However, such a modification is introduced only if a modification, for example a lipid modification, has not already been introduced at the 5' end of the (m)RNA of the inventive immunostimulatory composition or if the modification does not interfere with the immunogenic properties of the (unmodified or chemically modified) (m)RNA.

According to a further preferred embodiment, the at least one RNA of the active (immunostimulatory) composition of the present invention may contain, especially if the RNA is in the form of an mRNA, a poly-A tail on the 3' terminus of typically about 10 to 200 adenosine nucleotides, preferably about 10 to 100 adenosine nucleotides, more preferably about 20 to 100 adenosine nucleotides or even more preferably about 40 to 80 adenosine nucleotides.

According to a further preferred embodiment, the at least one RNA of the active (immunostimulatory) composition of the present invention may contain, especially if the RNA is in the form of an mRNA, a poly-C tail on the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

According to another embodiment, the at least one RNA of the active (immunostimulatory) composition of the present invention may be modified, and thus stabilized, especially if the RNA is in the form of an mRNA, by modifying the G/C content of the RNA, preferably of the coding region of the at least one RNA.

In a particularly preferred embodiment of the present invention, the G/C content of the coding region of the at least one (m)RNA of the active (immunostimulatory) composition of the present invention is modified, particularly increased, compared to the G/C content of the coding region of its particular wild-type (m)RNA, i.e. the unmodified (m)RNA. The encoded amino acid sequence of the at least one (m)RNA is preferably not modified compared to the coded amino acid sequence of the particular wild-type (m)RNA.

This modification of the at least one (m)RNA of the active (immunostimulatory) composition of the present invention is based on the fact that the sequence of any (m)RNA region to be translated is important for efficient translation of that (m)RNA. Thus, the composition and the sequence of various nucleotides is important. In particular, sequences having an increased G (guanosine)/C (cytosine) content are more stable than sequences having an increased A (adenosine)/U (uracil) content. According to the invention, the codons of the (m)RNA are therefore varied compared to its wild-type (m)RNA, while retaining the translated amino acid sequence, such that they include an increased amount of G/C nucleotides. In respect to the fact that several codons code for one and the same amino acid (so-called degeneration of the genetic code), the most favorable codons for the stability can be determined (so-called alternative codon usage).

Depending on the amino acid to be encoded by the at least one (m)RNA, there are various possibilities for modification of the (m)RNA sequence, compared to its wild-type sequence. In the case of amino acids which are encoded by codons which contain exclusively G or C nucleotides, no modification of the codon is necessary. Thus, the codons for Pro (CCC or CCG), Arg (CGC or CCGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:
the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:
the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the at least one (m)RNA of the active (immunostimulatory) composition of the present invention compared to its particular wild-type (m)RNA (i.e. the original sequence). Thus, for example, all codons for Thr occurring in the wild-type sequence can be modified to ACC (or ACG). Preferably, however, for example, combinations of the above substitution possibilities are used:
substitution of all codons coding for Thr in the original sequence (wild-type (m)RNA) to ACC (or ACG) and
substitution of all codons originally coding for Ser to UCC (or UCG or AGC);
substitution of all codons coding for Ile in the original sequence to AUC and
substitution of all codons originally coding for Lys to AAG and
substitution of all codons originally coding for Tyr to UAC;
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Arg to CGC (or CGG);
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Gly to GGC (or GGG) and
substitution of all codons originally coding for Asn to AAC;
substitution of all codons coding for Val in the original sequence to GUC (or GUG) and
substitution of all codons originally coding for Phe to UUC and
substitution of all codons originally coding for Cys to UGC and substitution of all codons originally coding for Leu to CUG (or CUC) and
substitution of all codons originally coding for Gln to CAG and
substitution of all codons originally coding for Pro to CCC (or CCG); etc.

Preferably, the G/C content of the coding region of the at least one (m)RNA of the active (immunostimulatory) composition of the present invention is increased by at least 7%, more preferably by at least 15%, particularly preferably by at least 20%, compared to the G/C content of the coded region of the wild-type (m)RNA which codes for an antigen, antigenic protein or antigenic peptide as defined herein or its fragment or variant thereof. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for an antigen, antigenic protein or antigenic peptide as defined herein or its fragment or variant thereof or the whole sequence of the wild type (m)RNA sequence are substituted, thereby increasing the GC/content of said sequence.

In this context, it is particularly preferable to increase the G/C content of the at least one (m)RNA of the active (immunostimulatory) composition of the present invention to the maximum (i.e. 100% of the substitutable codons), in particular in the region coding for a protein, compared to the wild-type sequence.

According to the invention, a further preferred modification of the at least one (m)RNA of the active (immunostimulatory) composition of the present invention is based on the finding that the translation efficiency is also determined by a different frequency in the occurrence of tRNAs in cells. Thus, if so-called "rare codons" are present in the at least one (m)RNA of the active (immunostimulatory) composition of the present invention to an increased extent, the corresponding modified at least one (m)RNA sequence is translated to a significantly poorer degree than in the case where codons coding for relatively "frequent" tRNAs are present.

According to the invention, in the modified at least one (m)RNA of the active (immunostimulatory) composition of the present invention, the region which codes for the adjuvant protein is modified compared to the corresponding region of the wild-type (m)RNA such that at least one codon of the wild-type sequence which codes for a tRNA which is relatively rare in the cell is exchanged for a codon which codes for a tRNA which is relatively frequent in the cell and carries the same amino acid as the relatively rare tRNA. By this modification, the sequences of the at least one (m)RNA of the active (immunostimulatory) composition of the present invention is modified such that codons for which frequently occurring tRNAs are available are inserted. In other words, according to the invention, by this modification all codons of the wild-type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified at least one (m)RNA of the active (immunostimulatory) composition of the present invention, with the "frequent" codons without modifying the amino acid sequence of the protein encoded by the coding region of the (m)RNA. This preferred embodiment allows provision of a particularly efficiently translated and stabilized (modified) at least one (m)RNA of the active (immunostimulatory) composition of the present invention.

The determination of a modified at least one (m)RNA of the active (immunostimulatory) composition of the present invention as described above (increased G/C content; exchange of tRNAs) can be carried out using the computer program explained in WO 02/098443—the disclosure content of which is included in its full scope in the present invention. Using this computer program, the nucleotide sequence of any desired (m)RNA can be modified with the aid of the genetic code or the degenerative nature thereof such that a maximum G/C content results, in combination with the use of codons which code for tRNAs occurring as frequently as possible in the cell, the amino acid sequence coded by the modified at least one (m)RNA preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443.

In a further preferred embodiment of the present invention, the A/U content in the environment of the ribosome binding site of the at least one (m)RNA of the active (immunostimulatory) composition of the present invention is increased compared to the A/U content in the environment of the ribosome binding site of its particular wild-type (m)RNA. This modification (an increased A/U content around the ribosome binding site) increases the efficiency of ribosome binding to the at least one (m)RNA. An effective binding of the ribosomes to the ribosome binding site (Kozak sequence: GCCGCCAC-CAUGG (SEQ ID NO: 27), the AUG forms the start codon) in turn has the effect of an efficient translation of the at least one (m)RNA.

According to a further embodiment of the present invention the at least one (m)RNA of the active (immunostimulatory) composition of the present invention may be modified with respect to potentially destabilizing sequence elements. Particularly, the coding region and/or the 5' and/or 3' untranslated region of this at least one (m)RNA may be modified compared to the particular wild-type (m)RNA such that is contains no destabilizing sequence elements, the coded amino acid sequence of the modified at least one (m)RNA preferably not being modified compared to its particular wild-type (m)RNA. It is known that, for example, in sequences of eukaryotic RNAs destabilizing sequence elements (DSE) occur, to which signal proteins bind and regulate enzymatic degradation of RNA in vivo. For further stabilization of the modified at least one (m)RNA, optionally in the region which encodes for an antigen, antigenic protein or antigenic peptide as defined herein, one or more such modifications compared to the corresponding region of the wild-type (m)RNA can therefore be carried out, so that no or substantially no destabilizing sequence elements are contained there. According to the invention, DSE present in the untranslated regions (3'- and/or 5'-UTR) can also be eliminated from the at least one (m)RNA of the active (immunostimulatory) composition of the present invention by such modifications.

Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The at least one (m)RNA of the active (immunostimulatory) composition of the present invention is therefore preferably modified compared to the wild-type (m)RNA such that the at least one (m)RNA contains no such destabilizing sequences. This also applies to those sequence motifs which are recognized by possible endonucleases, e.g. the sequence GAACAAG, which is contained in the 3'-UTR segment of the gene which codes for the transferrin receptor (Binder et al., EMBO J. 1994, 13: 1969 to 1980). These sequence motifs are also preferably removed in the at least one (m)RNA of the active (immunostimulatory) composition of the present invention.

Also preferably according to the invention, the at least one (m)RNA of the active (immunostimulatory) composition of the present invention has, in a modified form, at least one IRES as defined above and/or at least one 5' and/or 3' stabilizing sequence, in a modified form, e.g. to enhance ribosome binding or to allow expression of different encoded antigens located on an at least one (bi- or even multicistronic) RNA of the active (immunostimulatory) composition of the present invention.

According to the invention, the at least one (m)RNA of the active (immunostimulatory) composition of the present invention furthermore preferably has at least one 5' and/or 3' stabilizing sequence. These stabilizing sequences in the 5' and/or 3' untranslated regions have the effect of increasing the half-life of the at least one (m)RNA in the cytosol. These stabilizing sequences can have 100% sequence homology to naturally occurring sequences which occur in viruses, bacteria and eukaryotes, but can also be partly or completely synthetic. The untranslated sequences (UTR) of the globin gene, e.g. from *Homo sapiens* or *Xenopus laevis* may be mentioned as an example of stabilizing sequences which can be used in the present invention for a stabilized RNA. Another example of a stabilizing sequence has the general formula (C/U)CCAN$_x$CCC(U/A)Py$_x$UC(C/U)CC (SEQ ID NO: 28), which is contained in the 3'UTR of the very stable RNA which codes for globin, (I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. The at least one (m)RNA of the active (immunostimulatory) composition of the present invention is therefore preferably present as globin UTR (untranslated regions)-stabilized RNA, in particular as globin UTR-stabilized RNA.

Nevertheless, substitutions, additions or eliminations of bases are preferably carried out with the at least one RNA of the active (immunostimulatory) composition of the present invention, using a DNA matrix for preparation of the at least one RNA of the active (immunostimulatory) composition of the present invention by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N. Y., 2001). In such a process, for preparation of the at least one (m)RNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of an at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GENBANK® accession number U26404; Lai et al., Development 1995, 121: 2349 to 2360), pGEM® series, e.g. pGEM®-1 (GENBANK® accession number X65300; from Promega) and pSP64 (GENBANK® accession number X65327); cf. also Mezei and Storts, Purification of PCR Products, in: Griffin and Griffin (ed.), PCR Technology: Current Innovation, CRC Press, Boca Raton, Fla., 2001.

The stabilization of the at least one RNA of the active (immunostimulatory) composition of the present invention can likewise by carried out by associating or complexing the at least one RNA with, or binding it to, a cationic compound, in particular a polycationic compound, for example a (poly) cationic peptide or protein. In particular the use of protamine, nucleoline, spermin or spermidine as the polycationic, nucleic-acid-binding protein to the RNA is particularly effective. Furthermore, the use of other cationic peptides or proteins, such as poly-L-lysine or histones, is likewise possible. This procedure for stabilizing RNA is described in EP-A-1083232, the disclosure of which is incorporated by reference into the present invention in its entirety. Further preferred cationic substances which can be used for stabilizing the RNA of the active (immunostimulatory) composition of the present invention include cationic polysaccharides, for example chitosan, polybrene, polyethyleneimine (PEI) or poly-L-lysine (PLL), etc. Association or complexing of the at least one RNA of the inventive active (immunostimulatory) composition with cationic compounds, e.g. cationic proteins or cationic lipids, e.g. oligofectamine as a lipid based complexation reagent) preferably increases the transfer of the at least one RNA present as a pharmaceutically active component into the cells to be treated or into the organism to be treated. It is also referred to the disclosure herein with regard to the stabilizing effect for the at least one RNA of the active (immunostimulatory) composition of the present invention by complexation, which holds for the stabilization of RNA as well.

According to another particularly preferred embodiment, the at least RNA of the active (immunostimulatory) composition may additionally or alternatively encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the antigen, antigenic protein or antigenic peptide as encoded by the at least one RNA of the active (immunostimulatory) composition into a defined cellular compartment, preferably the cell surface, the endoplasmic reticulum (ER) or the endosomal-lysosomal compartment. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulines as defined herein, signal sequences of the invariant chain of immunoglobulines or antibodies as defined herein, signal sequences of Lamp1. Tapasin, Erp57, Calretikulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention.

Any of the above modifications may be applied to the at least one RNA of the active (immunostimulatory) composition of the present invention, and further to any (m)RNA as used in the context of the present invention and may be, if suitable or necessary, be combined with each other in any combination, provided, these combinations of modifications do not interfere with each other in the respective at least one RNA. A person skilled in the art will be able to take his choice accordingly.

According to another embodiment, the active (immunostimulatory) composition according to the invention may comprise an adjuvant. In this context, an adjuvant may be understood as any compound, which is suitable to support administration and delivery of the active (immunostimulatory) composition according to the invention. Furthermore, such an adjuvant may, without being bound thereto, initiate or increase an immune response of the innate immune system, i.e. a non-specific immune response. With other words, when administered, the active (immunostimulatory) composition according to the invention typically initiates an adaptive immune response due to the at least two antigens encoded by the at least one RNA contained in the inventive active (immunostimulatory) composition. Additionally, the active (immunostimulatory) composition according to the invention may generate an (supportive) innate immune response due to addition of an adjuvant as defined herein to the active (immunostimulatory) composition according to the invention. Such an adjuvant may be selected from any adjuvant known to a skilled person and suitable for the present case, i.e. supporting the induction of an immune response in a mammal. Preferably, the adjuvant may be selected from the group consisting of, without being limited thereto, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAPTM (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methypropyl)-1H-imidazol[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interdeukin-12; ISCOMS™; ISCOPREP 7.0.3.™; liposomes; LOXORIBINE™ (7-allyl-8-oxoguanosine); LT oral adjuvant (E. coli labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH$_3$); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyhyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adjuphos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010, etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Suitable adjuvants may also be selected from cationic or polycationic compounds wherein the adjuvant is preferably prepared upon complexing the at least one RNA of the inventive active (immunostimulatory) composition) with the cationic or polycationic compound. Association or complexing the RNA of the active (immunostimulatory) composition with cationic or polycationic compounds as defined herein preferably provides adjuvant properties and confers a stabilizing effect to the at least one RNA of the active (immunostimulatory) composition. Particularly such preferred, such cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsI, FGF, Lactoferrin, Transportan, Buforin-2, Bac715-24, SynB, SynB(1), pVEC, hCT-derived peptides, SAP, protamine, spermine, spermidine, or histories. Further preferred cationic or polycationic compounds may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicyspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as O-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected of a cationic polymer as mentioned above) and of one or more hydrophilic- or hydrophobic blocks (e.g polyethyleneglycole); etc.

Additionally, preferred cationic or polycationic proteins or peptides, which can be used as an adjuvant by complexing the at least one RNA of the active (immunostimulatory) composition, may be selected from following proteins or peptides having the following total formula (I): $(Arg)_l;(Lys)_m;(His)_n;(Orn)_o(Xaa)_x$, wherein l+m+n+o+x=8-15, and 1, m, n or independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred oligoorginines in this context are e.g. $Arg_7$ (SEQ ID NO: 15), $Arg_8$ (SEQ ID NO: 16), $Arg_9$ (SEQ ID NO: 17), $Arg_7$ (SEQ ID NO: 18), $H_3R_9$ (SEQ ID NO: 19), $R_9H_3$ (SEQ ID NO: 20), $H_3R_9H_3$ (SEQ ID NO: 21), $YSSR_9SSY$ (SEQ ID NO: 22), $(RKH)_4$ (SEQ ID NO: 23), $Y(RKH)_2R$ (SEQ ID NO: 24), etc.

Suitable adjuvants may furthermore be selected from nucleic acids having the formula (II): $G_lX_mG_n$, wherein: G is guanosine, uracil or an analogue of guanosine or uracil; X is guanosine, uracil, adenosine, thymidine, cytosine or an analogue of the above-mentioned nucleotides; l is an integer from 1 to 40, wherein when l=1 G is guanosine or an analogue thereof, when l>1 at least 50% of the nucleotides are guanosine or an analogue thereof; m is an integer and is at least 3; wherein when m=3 X is uracil or an analogue thereof, when m>3 at least 3 successive uracil or analogues of uracil occur; n is an integer from 1 to 40, wherein when n=1 G is guanosine or an analogue thereof, when n>1 at least 50% of the nucleotides are guanosine or an analogue thereof.

Other suitable adjuvants may furthermore be selected from nucleic acids having the formula (III): $C_lX_mC_n$, wherein: C is cytosine, uracil or an analogue of cytosine or uracil; X is guanosine, uracil, adenosine, thymidine, cytosine or an analogue of the above-mentioned nucleotides; l is an integer from 1 to 40, wherein when l=1 C is cytosine or an analogue thereof, when l>1 at least 50% of the nucleotides are cytosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 C is cytosine or an analogue thereof, when n>1 at least 50% of the nucleotides are cytosine or an analogue thereof.

According to one preferred embodiment, the present invention may furthermore provide a vaccine containing the active (immunostimulatory) composition according to the invention. The inventive vaccine may additionally contain a pharmaceutically acceptable carrier and/or further auxiliary substances and additives and/or adjuvants. According to a particularly preferred embodiment, the antigens encoded by the at least one RNA of the active (immunostimulatory) composition, contained in the inventive vaccine, are selected from the above mentioned group.

The inventive vaccine typically comprises a safe and effective amount of the at least one RNA of the active (immunostimulatory) composition as defined above encoding at least two antigens as defined above, more preferably encoding at least two antigens selected from any of the above goupmost preferably in any of the indicated combinations. As used herein, "safe and effective amount" means an amount of the at least one RNA of the active (immunostimulatory) composition in the vaccine as defined above, that is sufficient to significantly induce a positive modification of prostate cancer (PCa), preferably of neoadjuvant and/or hormone-refractory prostate cancers, and diseases or disorders related thereto. At the same time, however, a "safe and effective amount" is small enough to avoid serious side-effects, that is to say to permit a sensible relationship between advantage and risk. The determination of these limits typically lies within the scope of sensible medical judgment. In relation to the inventive vaccine, the expression "safe and effective amount" preferably means an amount of the RNA (and thus of the encoded at least two antigens) that is suitable for stimulating the adaptive immune system in such a manner that no excessive or damaging immune reactions are achieved but, preferably, also no such immune reactions below a measurable level. Such a "safe and effective amount" of the at least one RNA of the active (immunostimulatory) composition in the vaccine as defined above may furthermore be selected in dependence of the type of RNA, e.g. monocistronic, bi- or even multicistronic RNA, since a bi- or even multicistronic RNA may lead to a significantly higher expression of the encoded antigen(s) than use of an equal amount of a monocistronic RNA. A "safe and effective amount" of the at least one RNA of the active (immunostimulatory) composition as defined above, which is contained in the inventive vaccine, will furthermore vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The vaccine according to the invention can be used according to the invention for human and also for veterinary medical purposes, as a pharmaceutical composition or as a vaccine.

The vaccine according to the invention typically contains a pharmaceutically acceptable carrier. The expression "pharmaceutically acceptable carrier" as used herein preferably includes the liquid or non-liquid basis of the inventive vaccine. If the inventive vaccine is provided in liquid form, the carrier will typically be pyrogen-free water; isotonic saline or buffered (aqueous) solutions, e.g phosphate, citrate etc. buffered solutions. Particularly for injection of the inventive vaccine, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. CaCl, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_3$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well, which are suitable for administration to a person. The term "compatible" as used herein means that the constituents of the inventive vaccine are capable of being mixed with the at least one RNA of the active (immunostimulatory) composition, encoding at least two antigens as defined above, in such a manner that no interaction occurs which would substantially reduce the pharmaceutical effectiveness of the inventive vaccine under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethykellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Compositions/vaccines are therefore preferably formulated in liquid or solid form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine can additionally contain one or more auxiliary substances in order to further increase the immunogenicity. A synergistic action of the at least one RNA of the active (immunostimulatory) composition as defined above and of an auxiliary substance, which may be optionally also contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that—additional to induction of the adaptive immune response by the encoded at least two antigens—promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13. Another class of compounds, which may be added to an inventive vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to a further preferred object of the present invention, the inventive active (immunostimulatory) composition may be used (for the preparation of a vaccine according to the present invention) for the treatment of prostate cancer (PCa), preferably of neoadjuvant and/or hormone-refractory prostate cancers, and diseases or disorders related thereto.

According to a further preferred object of the present invention, the inventive vaccine or the at least one RNA encoding at least two (preferably) different antigens as defined herein may be used for the treatment of prostate cancer (PCa), preferably of neoadjuvant and/or hormone-refractory prostate cancers, and diseases or disorders related thereto.

In this context also included in the present invention are methods of treating prostate cancer (PCa), preferably of neoadjuvant and/or hormone-refractory prostate cancers, and diseases or disorders related thereto, by administering to a patient in need thereof a pharmaceutically effective amount of an inventive vaccine, or a pharmaceutically effective amount of an inventive active (immunostimulatory) composition. Such a method typically comprises an optional first step of preparing the inventive active (immunostimulatory) composition, or the inventive vaccine, and a second step, comprising administering (a pharmaceutically effective amount of) said inventive active (immunostimulatory) composition or said inventive vaccine to a patient in need thereof. A patient in need thereof will be typically selected from any mammal. In the context of the present invention, a mammal is preferably a mammal, selected from the group comprising, without being limited thereto, e.g. goat, cattle, swine, dog cat, donkey; monkey, ape, a rodent such as a mouse, hamster, rabbit and, particularly, human, wherein the mammal typically suffers from prostate cancer (PCa), preferably of neoadjuvant and/or hormone-refractory prostate cancers, and diseases or disorders related thereto.

The invention relates also to the use of the inventive active (immunostimulatory) composition or the at least one RNA encoding at least two (preferably) different antigens as defined herein (for the preparation of an inventive vaccine), preferably for eliciting an immune response in a mammal, preferably for the treatment of prostate cancer (PCa), more preferably of neoadjuvant and/or hormone-refractory prostate cancers, and diseases or disorders related thereto.

Similarly, the invention also relates also to the use of the inventive vaccine per se or the at least one RNA encoding at least two (preferably) different antigens as defined herein for eliciting an adaptive immune response in a mammal, preferably for the treatment of prostate cancer (PCa), preferably of neoadjuvant and/or hormone-refractory prostate cancers, and diseases or disorders related thereto.

Prevention or treatment of prostate cancer (PCa), preferably of neoadjuvant and/or hormone-refractory prostate cancers, and diseases or disorders related thereto, may be carried out by administering the inventive active (immunostimulatory) composition and/or the inventive vaccine at once or in a time staggered manner, e.g. as a kit of parts, each part containing at least one preferably different antigen. For administration, preferably any of the administration routes may be used as defined above. E.g., one may treat prostate cancer (PCa), preferably of neoadjuvant and/or hormone-refractory prostate cancers, and diseases or disorders related thereto, by inducing or enhancing an adaptive immune response on the basis of at least two (specifically selected) antigens encoded by the at least one RNA of the inventive active (immunostimulatory) composition. Administering of the inventive inventive active (immunostimulatory) composition and/or the inventive vaccine may then occur prior, concurrent and/or subsequent to administering another inventive inventive active (immunostimulatory) composition and/or inventive vaccine as defined herein which may contain another combination of RNAs encoding different antigens, wherein each antigen encoded by the at least one RNA of the inventive active (immunostimulatory) composition may preferably be suitable for the therapy of prostate cancer (PCa), preferably of neoadjuvant and/or hormone-refractory prostate cancers, and diseases or disorders related thereto. In this context, a therapy as defined herein may also comprise the modulation of a disease associated to prostate cancer (PCa), preferably of neoadjuvant and/or hormone-refractory prostate cancers, and of diseases or disorders related thereto, According to one further embodiment, the present invention furthermore comprises the use of the inventive active (immunostimulatory) composition or the at least one RNA encoding at least two (preferably) different antigens as defined herein (for the preparation of an (inventive) vaccine) for modulating, preferably to induce or enhance, an immune response in a mammal as defined above, more preferably to treat and/or to support the treatment of prostate cancer (PCa), preferably of a neoadjuvant and/or hormone-refractory prostate cancer, or of diseases or disorders related thereto. In this context, support of the treatment of prostate cancer (PCa) may be any combination of a conventional prostate cancer therapy method of such as surgery, radiation therapy, hormonal therapy, occasionally chemotherapy, proton therapy, or some combination of these, and a therapy using the inventive active (immunostimulatory) composition as defined herein. Support of the treatment of prostate cancer (PCa) may be also envisaged in any of the other embodiments defined herein.

Administration of the inventive active (immunostimulatory) composition or the at least one RNA encoding at least two (preferably) different antigens as defined herein or the inventive vaccine may be carried out in a time staggered treatment. A time staggered treatment may be e.g. administration of the inventive active (immunostimulatory) composition or the at least one RNA encoding at least two (preferably) different antigens as defined herein or the inventive vaccine prior, concurrent and/or subsequent to a conventional therapy of prostate cancer (PCa), preferably of neoadjuvant and/or hormone-refractory prostate cancers, and diseases or disorders related thereto, e.g. by administration of the inventive medicament or the active inventive (immunostimulatory) composition or vaccine prior, concurrent and/or subsequent to a therapy or an administration of a therapeutic suitable for the treatment of prostate cancer (PCa), preferably of neoadjuvant and/or hormone-refractory prostate cancers, and diseases or disorders related thereto. Such time staggered treatment may be carried out using e.g. a kit, preferably a kit of parts as defined below.

Time staggered treatment may additionally or alternatively also comprise an administration of the inventive active (immunostimulatory) composition or vaccine, preferably of the at least one RNA encoding at least two (preferably different) antigens as defined above, in a form, wherein the at least one RNA encoding at least two (preferably different) antigens as defined above, preferably forming part of the inventive active (immunostimulatory) composition or vaccine, is administered parallel, prior or subsequent to another at least one RNA encoding at least two (preferably different) antigens as defined above, preferably forming part of the same inventive active (immunostimulatory) composition or vaccine. Preferably, the administration (of all at least one RNAs) occurs within an hour, more preferably within 30 minutes, even more preferably within 15, 10, 5, 4, 3, or 2 minutes or even within 1 minute. Such time staggered treatment may be carried out using e.g. a kit, preferably a kit of parts as defined below.

According to a final embodiment, the present invention also provides kits, particularly kits of parts, comprising the active inventive (immunostimulatory) composition, and/or the inventive vaccine, and optionally technical instructions with information on the administration and dosage of the inventive active (immunostimulatory) composition and/or the inventive vaccine. The technical instructions may contain information about administration and dosage of the inventive active (immunostimulatory) composition, and/or the inventive vaccine. Such kits, preferably kits of parts, may applied e.g. for any of the above mentioned applications or uses, preferably for the use of at least one inventive active (immunostimulatory) composition (for the preparation of an inventive medicament, preferably a vaccine) for the treatment of prostate cancer (PCa), preferably of neoadjuvant and/or hormone-refractory prostate cancers, and diseases or disorders related thereto. The kits may also be applied for the use of at least one inventive active (immunostimulatory) composition (for the preparation of an inventive vaccine) for the treatment of prostate cancer (PCa), preferably of neoadjuvant and/or hormone-refractory prostate cancers, and diseases or disorders related thereto, wherein the inventive active (immunostimulatory) composition) and/or the vaccine due to the encoded at least two antigens may be capable to induce or enhance an immune response in a mammal as defined above. Such kits may further be applied for the use of at least one inventive active (immunostimulatory) composition, (for the preparation of an inventive medicament, preferably a vaccine) for modulating, preferably for eliciting, e.g. to induce or enhance, an immune response in a mammal as defined above, and preferably to support treatment of prostate cancer (PCa), preferably of neoadjuvant and/or hormone-refractory prostate cancers, and diseases or disorders related thereto. Kits of parts, as a special form of kits, may contain one or more identical or different active inventive (immunostimulatory) compositions and/or one or more identical or different inventive vaccines in different parts of the kit. Kits of parts may also contain an (e.g. one) active inventive (immunostimulatory) composition, an (e.g. one) inventive vaccine and/or the at least one RNA encoding at least one antigen as defined above in different parts of the kit, e.g. each part of the kit containing at least one RNA encoding a preferably different antigen. Additionally, a combination of both types of kits of parts is possible. Kits of parts may be used, e.g. when a time staggered treatment is envisaged, e.g. when using different formulations and/or increasing concentrations of the active inventive (immunostimulatory) composition, the inventive vaccine and/or the at least one RNA encoding at least one antigens as defined above during the same treatment in vivo. Kits of parts may also be used when a separated formulation or administration of the different antigens of the inventive active (immunostimulatory) composition (i.e. in parts) is envisaged or necessary (e.g. for technical reasons), but e.g. a combined presence of the different antigens in vivo is still to be achieved. Particularly kits of parts as a special form of kits are envisaged, wherein each part of the kit contains at least one preferably different antigen as defined above, all parts of the kit of parts preferably forming the active inventive (immunostimulatory) composition or the inventive vaccine as defined herein. Such specific kits of parts may particularly be suitable, e.g. if different antigens are formulated separately as different parts of the kits, but are then administered at once together or in a time staggered manner to the mammal in need thereof. In the latter case administration of all of the different parts of such a kit typically occurs within a short time limit, such that all antigens are present in the mammal at about the same time subsequent to administration of the last part of the kit. Any of the above kits may be used in a treatment as defined above.

ADVANTAGES OF THE PRESENT INVENTION

The present invention provides an active (immunostimulatory) composition for the treatment of prostate cancer (PCa), wherein the composition comprises at least one RNA, preferably an mRNA, encoding at least two (preferably different) antigens capable of eliciting an (adaptive) immune response in a mammal wherein the antigens are selected from the group consisting of PSA (Prostate-Specific Antigen), PSMA (Prostate-Specific Membrane Antigen), PSCA (Prostate Stem Cell Antigen), and STEAP (Six Transmembrane Epithelial Antigen of the Prostate). Such an active (immunostimulatory) composition allows efficient treatment of prostate cancer (PCa) or supplementary treatment when using conventional therapies. It furthermore avoids the problem of uncontrolled propagation of the introduced DNA sequences by the use of RNA as an approach for curative methods. RNA as used in the inventive active (immunostimulatory) composition has additional considerable advantages over DNA expression systems e.g. in immune response, immunization or vaccination. These advantages include, inter alia, that RNA introduced into a cell is not integrated into the genome. This avoids the risk of mutation of this gene, which otherwise may be completely or partially inactivated or give rise to misinformation. It further avoids other risks of using DNA as an agent to induce an immune response (e.g. as a vaccine) such as the induction of pathogenic anti-DNA antibodies in the patient into whom the foreign DNA has been introduced, so bringing about a (possibly fatal) immune response. In contrast, no anti-RNA antibodies have yet been detected.

FIGURES

The following Figures are intended to illustrate the invention further. They are not intended to limit the subject matter of the invention thereto.

FIG. 1: depicts the plasmid construct RNActive CAP-KLK3(GC)-muag-A70-C30 (SEQ ID NO: 1), encoding for PSA (prostate specific antigen) (=KLK3). The construct contains following sequence elements:
  a GC-optimized sequence for stabilization and a better codon usage
  ~70× Adenosin at the 3'-terminal end (poly-A-tail),
  ~30× Cytosin at the 3'-terminal end (poly-C-tail);
  This DNA construct corresponds to the coding mRNA and served as a basis for preparation of the corresponding RNA construct by in vitro transcription experiments.

FIG. 2: depicts the wildtype-coding sequence corresponding to the RNA construct RNActive CAP-KLK3(GC)-muag-A70-C30 (SEQ ID NO: 2), encoding for PSA (prostate specific antigen) (=KLK3), i.e. the coding sequence (CDS) encoding PSA (prostate specific antigen) without GC-optimized sequence.

FIG. 3: depicts the GC-optimized coding sequence of the RNA construct RNActive CAP-KLK3(GC)-muag-A70-C30 (SEQ ID NO: 3), encoding for PSA (prostate specific antigen) (=KLK3), i.e. the coding sequence (CDS) encoding PSA (prostate specific antigen) with GC-optimized sequence.

FIG. 4: depicts the plasmid construct RNActive CAP-FOLH1(GC)-muag-A70-C30 (SEQ ID NO: 4), encoding for PSMA (prostate specific membrane antigen) (=FOLH1). The construct contains following sequence elements:
  a GC-optimized sequence for stabilization and a better codon usage
  ~70× Adenosin at the 3'-terminal end (poly-A-tail),
  30× Cytosin at the 3'-terminal end (poly-C-tail);
  This DNA construct corresponds to the coding mRNA and served as a basis for generation of the corresponding RNA construct by in vitro transcription experiments.

FIG. 5: depicts the wt-coding sequence corresponding to the RNA construct RNActive CAP-FOLH1(GC)-muag-A70-C30 (SEQ ID NO: 5), encoding for PSMA (prostate specific membrane antigen) (=FOLH1), i.e. the coding sequence (CDS) encoding PSMA (prostate specific membrane antigen) (=FOLH1) without GC-optimized sequence.

FIG. 6: depicts the GC-optimized coding sequence of the RNA construct RNActive CAP-FOLH1(GC)-muag-A70-C30 (SEQ ID NO: 6), encoding for PSMA (prostate specific membrane antigen) (=FOLH1), i.e. the coding sequence (CDS) encoding PSMA (prostate specific membrane antigen) (=FOLH1) with GC-optimized sequence.

FIG. 7: depicts the plasmid construct RNActive CAP-PSCA(GC)-muag-A70-C30 (SEQ ID NO: 7), encoding for PSCA (prostate stem cell antigen). The construct contains following sequence elements:
  a GC-optimized sequence for stabilization and a better codon usage
  ~70× Adenosin at the 3'-terminal end (poly-A-tail),
  30× Cytosin at the 3'-terminal end (poly-C-tail);
  This DNA construct corresponds to the coding mRNA and served as a basis for generation of the corresponding RNA construct by in vitro transcription experiments.

FIG. 8: depicts the wt-coding sequence corresponding to the RNA construct RNActive CAP-PSCA(GC)-muag-A70-C30 (SEQ ID NO: 8), encoding for PSCA (prostate stem cell antigen), i.e. the coding sequence (CDS) encoding PSCA (prostate stem cell antigen) without GC-optimized sequence.

FIG. 9: depicts the GC-optimized coding sequence of the RNA construct RNActive CAP-PSCA(GC)-muag-A70-C30 (SEQ ID NO: 9), encoding for PSCA (prostate stem cell antigen), i.e. the coding sequence (CDS) encoding PSCA (prostate stem cell antigen) with GC-optimized sequence.

FIG. 10: depicts the plasmid construct RNActive CAP-STEAP(GC)-muag.A70-C30 (SEQ ID NO: 10), encoding for STEAP (Six Transmembrane Epithelial Antigen of the Prostate). The construct contains following sequence elements:
  a GC-optimized sequence for stabilization and a better codon usage
  ~70× Adenosin at the 3'-terminal end (poly-A-tail),
  30× Cytosin at the 3'-terminal end (poly-C-tail);
  This DNA construct corresponds to the coding mRNA and served as a basis for generation of the corresponding RNA construct by in vitro transcription experiments.

FIG. 11: depicts the wt-coding sequence corresponding to the RNA construct RNActive CAP-STEAP(GC)-muag-A70-C30 (SEQ ID NO: 11), encoding for STEAP (Six Transmembrane Epithelial Antigen of the Prostate), i.e. the coding sequence (CDS) encoding STEAP (Six Transmembrane Epithelial Antigen of the Prostate) without GC-optimized sequence.

FIG. 12: depicts the GC-optimized coding sequence of the RNA construct RNActive CAP-STEAP(GC)-muag-A70.C30 (SEQ ID NO: 12), encoding for STEAP (Six Transmembrane Epithelial Antigen of the Prostate), i.e. the coding sequence (CDS) encoding STEAP (Six Transmembrane Epithelial Antigen of the Prostate) with GC-optimized sequence.

FIG. 13: depicts the detection of an antigen-specific immune response (B-cell immune response) by detecting antigen-specific antibodies. As can be seen in FIG. 13, administration of an RNA-Mix, i.e. of an PCa-RNA cocktail comprising mRNA coding for PSA, PSMA, PSCA or STEAP, respectively, showed a significant induction of an antigen-specific immune response (B-cell immune response) due to significant formation of IgG2a antibodies against PSA in comparison to samples containing a buffer or the control.

Figure 14:
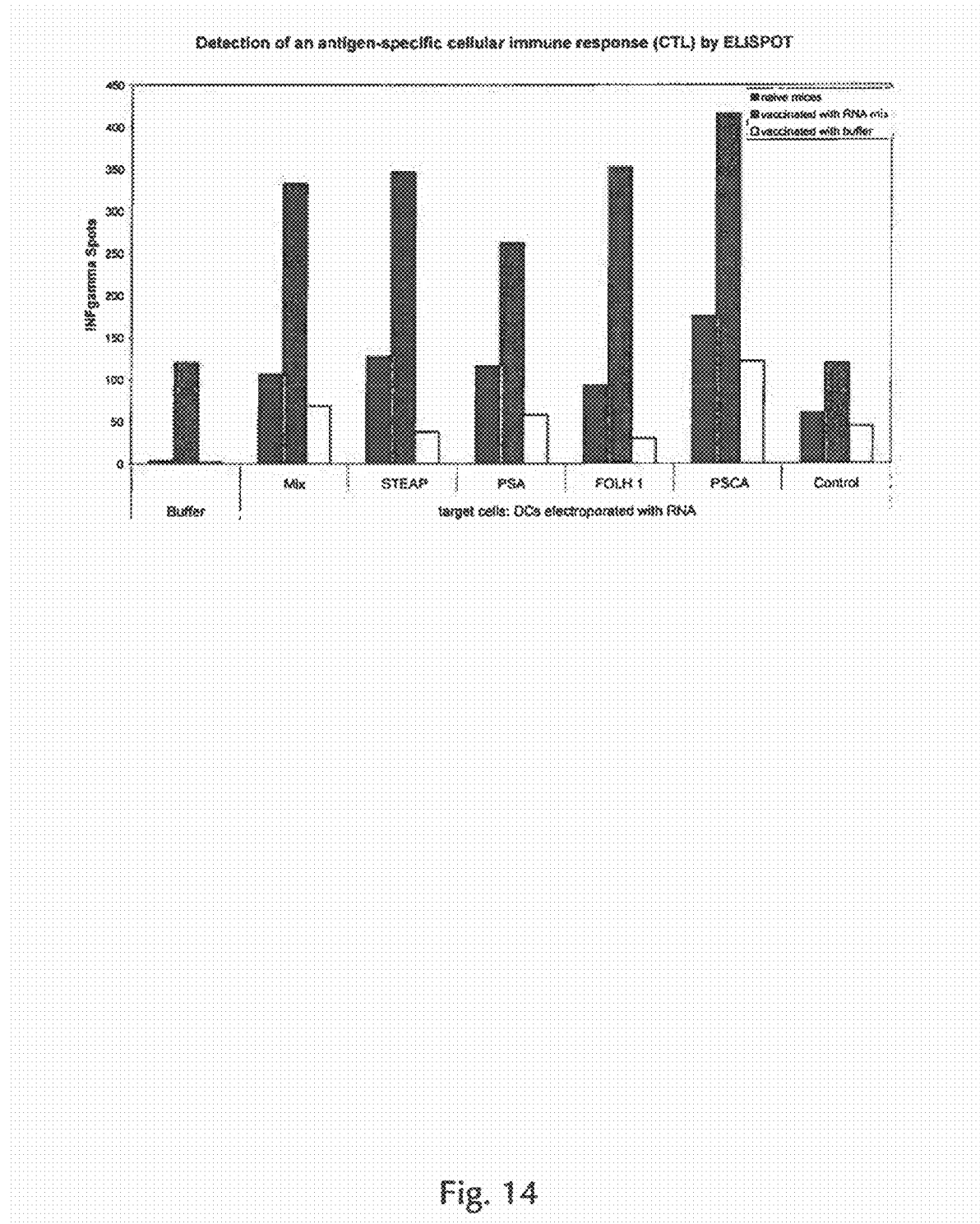
Figure 15:
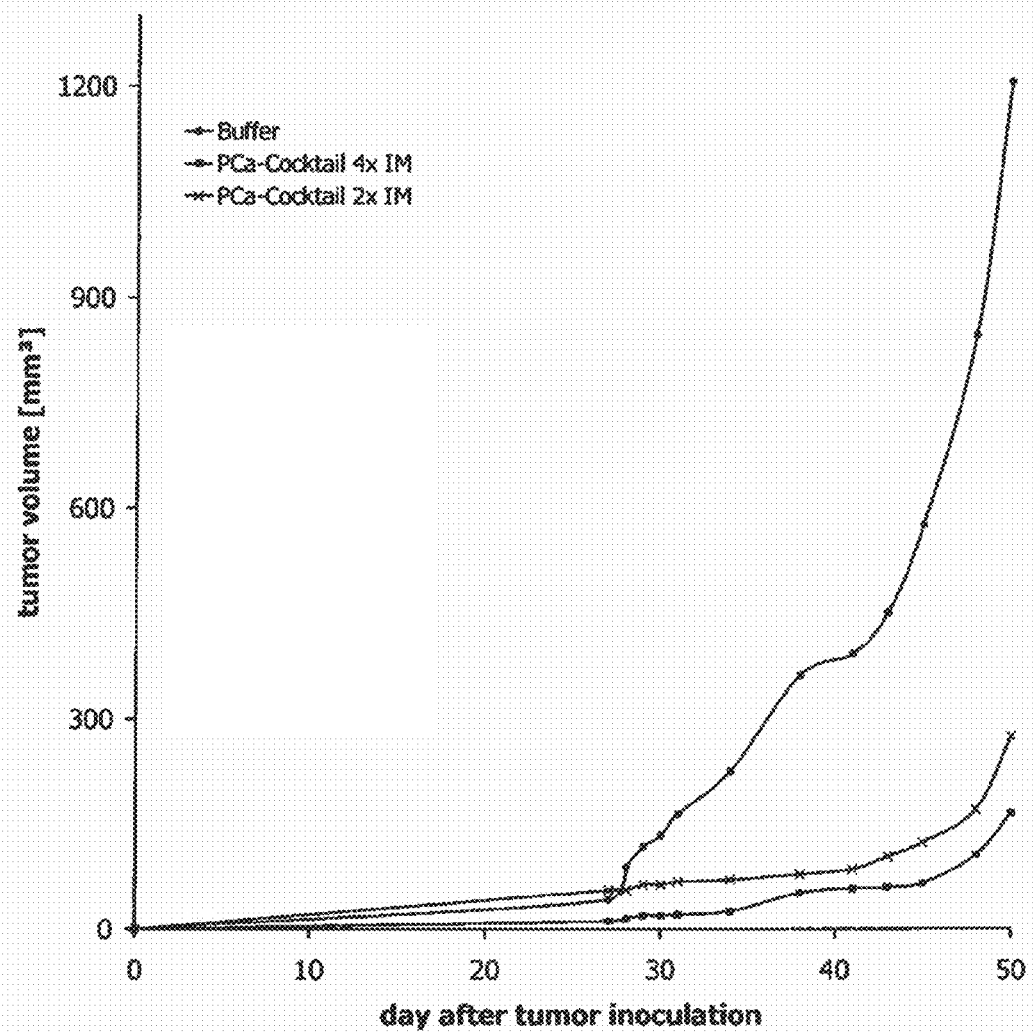

FIG. 14: shows detection of an antigen-specific cellular immune response by ELISPOT. As can be seen in FIG. 15, vaccination of mice with an RNA-Mix, i.e. with an PCa-RNA cocktail comprising mRNA coding for PSA, PSMA, PSCA or STEAP, respectively, or with mRNA coding for PSA, PSMA, PSCA or STEAP, respectively, leads to a significant induction of an antigen-specific immune response (CTL) due to significant formation of INFgamma in comparison to native mice and mice vaccinated with buffer.

FIG. 15: depicts immunization and tumor challenge by using the inventive PCa-RNA cocktail comprising 5 µg from mRNA coding for PSA, PSMA, PSCA and STEAP respectively. As could be seen in FIG. 15, the tumor volume is significantly reduced upon immunization with the PCa-RNA cocktail according to a) 2× i.m. (intramuscularly) comprising mRNA coding for PSA, PSMA, PSCA and STEAP, respectively. The tumor volume is even more reduced, when the PCa-RNA cocktail according to a) is administered 4× i.m. (intramuscularly).

Figure 16:
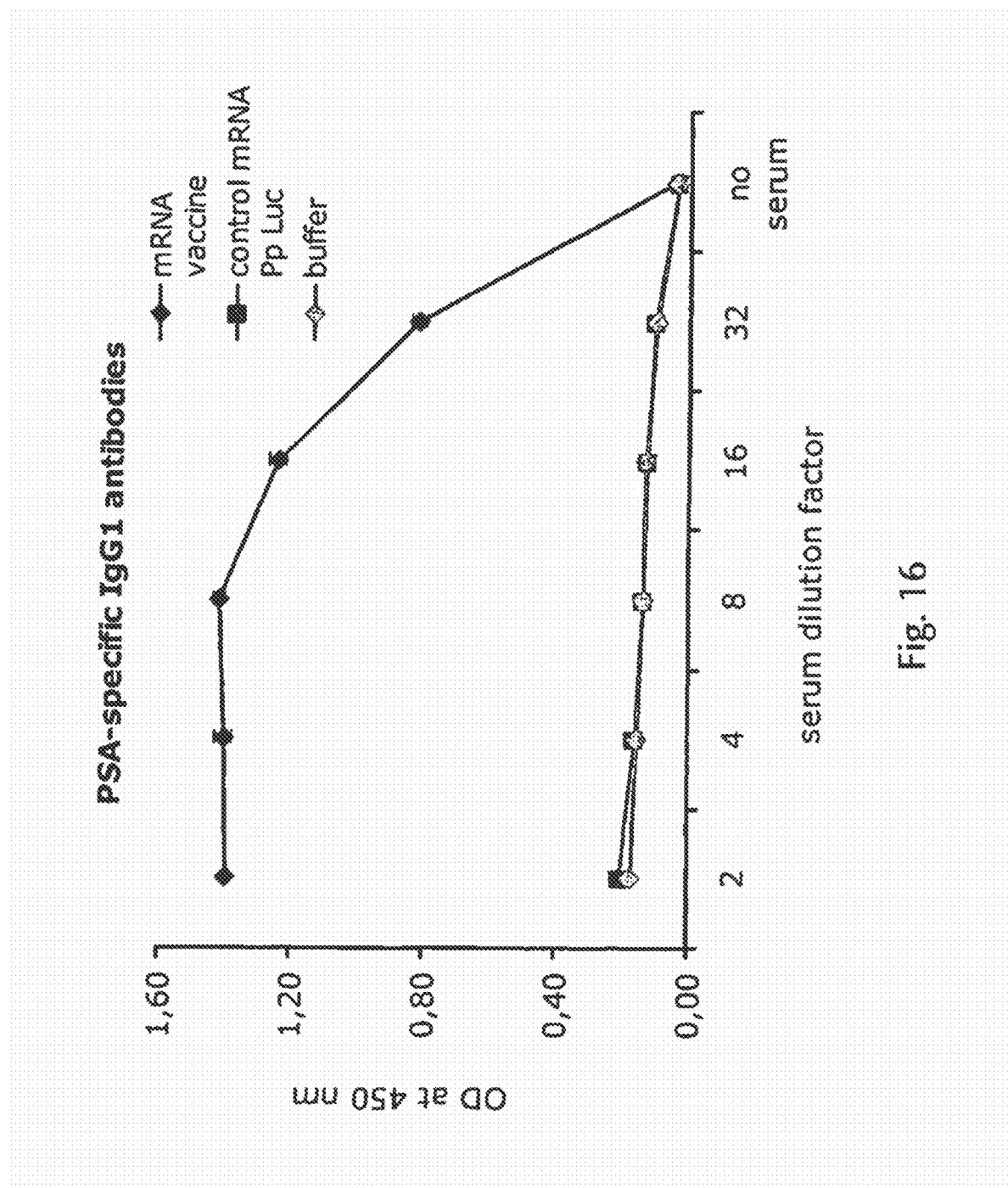

FIG. 16: depicts the induction of PSA-specific IgG1 antibodies. FIG. 16 particularly shows the presence of IgG1 antibodies specific for the tumor antigen PSA in mice which were vaccinated with the mRNA vaccine consisting of 4 components, containing GC-optimized mRNAs coding for the human prostate differentiation antigens PSMA, STEAP, PSA and PSCA. Each was formulated with the cationic peptide protamine. Control mice were treated either with buffer (Ringer-lactate) or with irrelevant RNA (Pp Luc) formulated with protamine analog to the mRNA vaccine. For the analysis sera from 5 mice in each group were pooled and titrated. Error bars represent mean deviations of two replicates from the mean.

Figure 17:
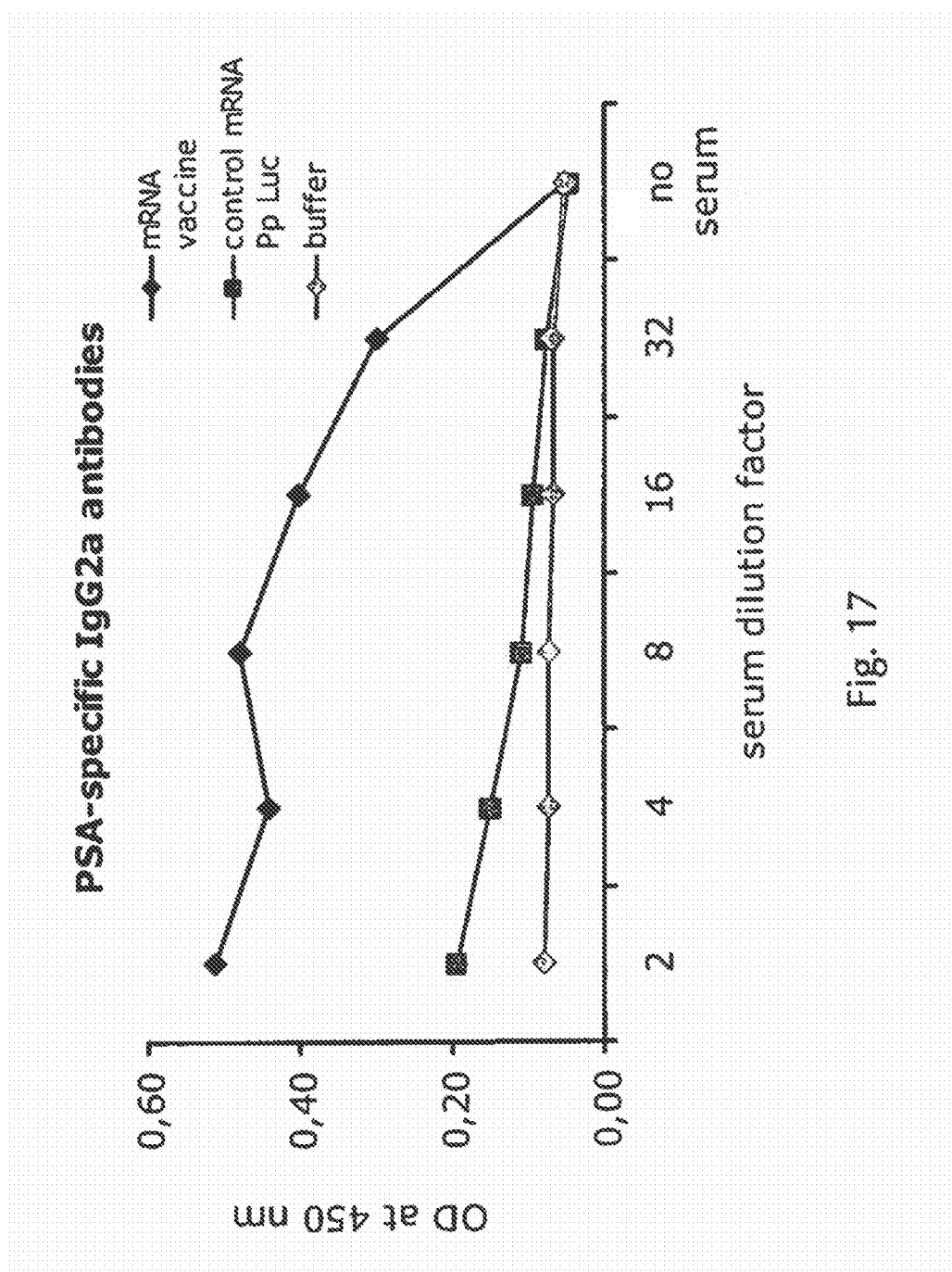

FIG. 17: shows the induction of PSA-specific IgC2a antibodies. FIG. 17 particularly shows the presence of IgG2a antibodies specific for the tumor antigen PSA in mice which were vaccinated with the mRNA vaccine consisting of 4 components, each containing GC-optimized mRNAs coding for the human prostate differentiation antigens PSMA, STEAP, PSA and PSCA. Each was formulated with the cationic peptide protamine. Control mice were treated either with buffer (Ringer-lactate) or with irrelevant RNA (Pp Luc) formulated with protamine analog to the mRNA vaccine. For the analysis sera from 5 mice in each group were pooled and titrated. Error bars represent mean deviations of two replicates from the mean.

Figure 18:
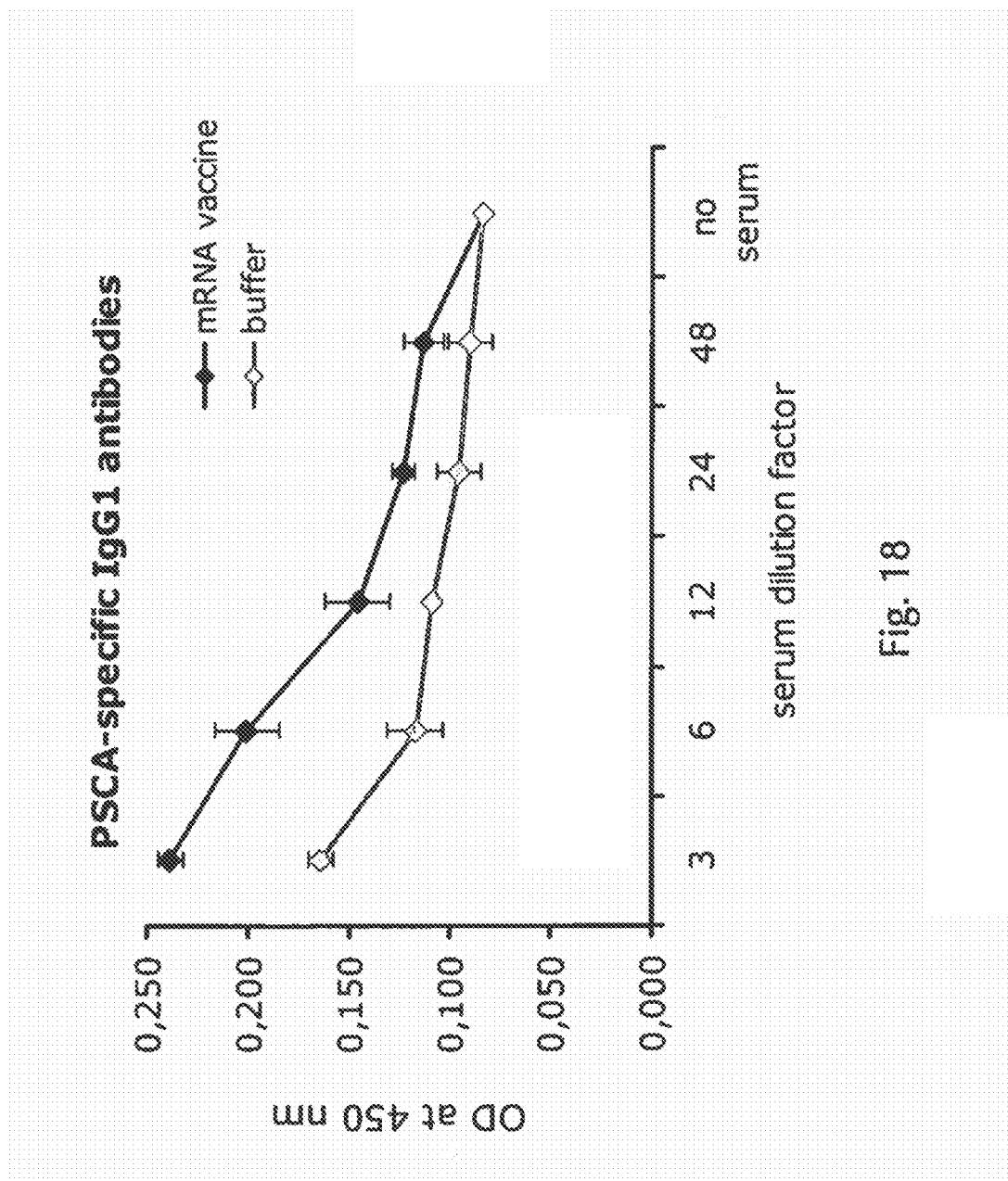

FIG. 18: describes the results of the induction of PSCA-specific IgG1 antibodies. Particularly, FIG. 18 shows the presence of IgG1 antibodies specific for the tumor antigen PSCA in mice which were vaccinated with the mRNA vaccine consisting of 4 components, each containing GC-optimized mRNAs coding for the human prostate differentiation antigens PSMA, STEAP, PSA and PSCA. Each was formulated with the cationic peptide protamine. Control mice were treated with buffer (Ringer-lactate). For the analysis sera from 5 mice in each group were pooled and titrated. Error bars represent mean deviations of two replicates from the mean.

Figure 19:
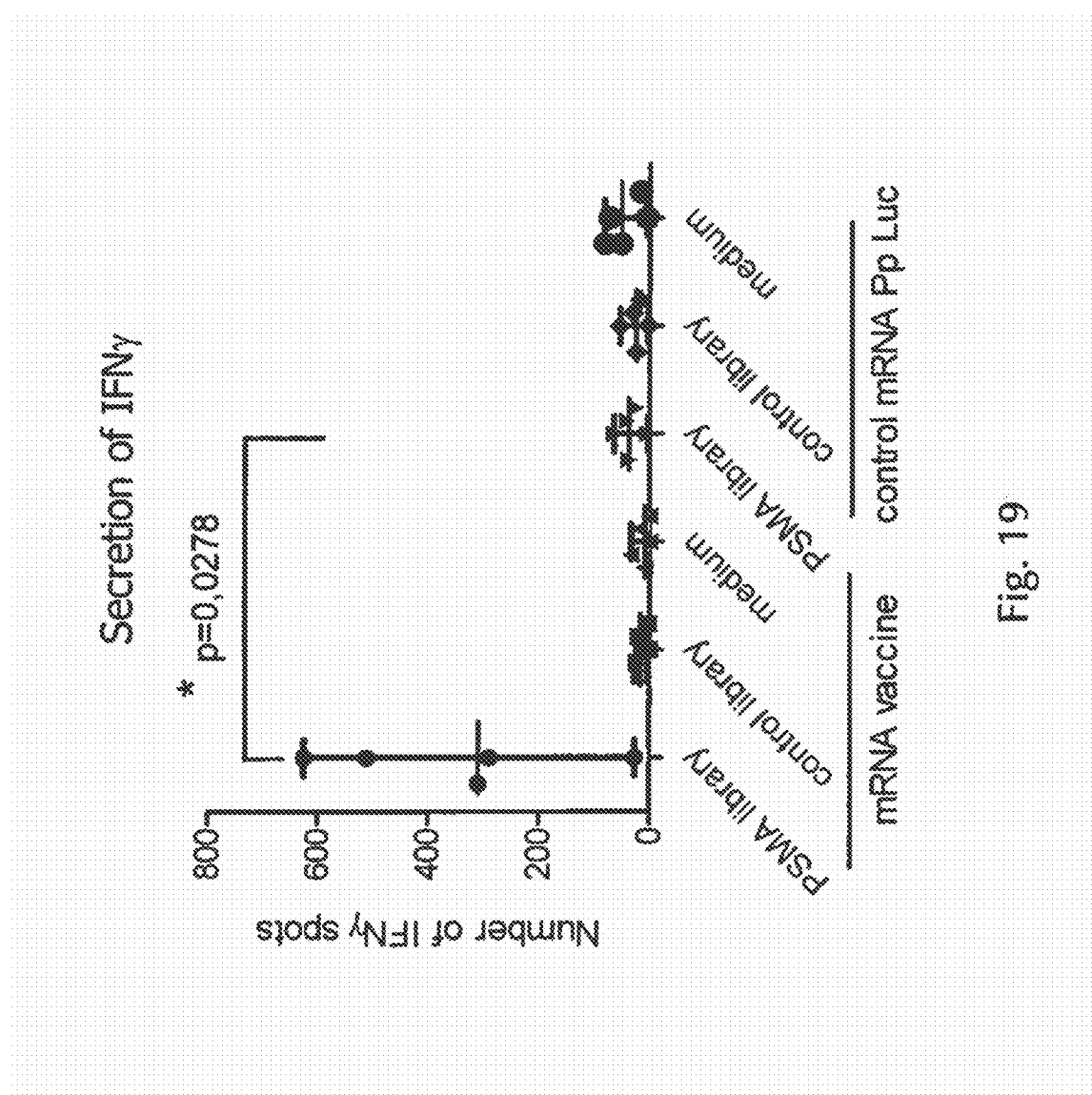
Figure 20:
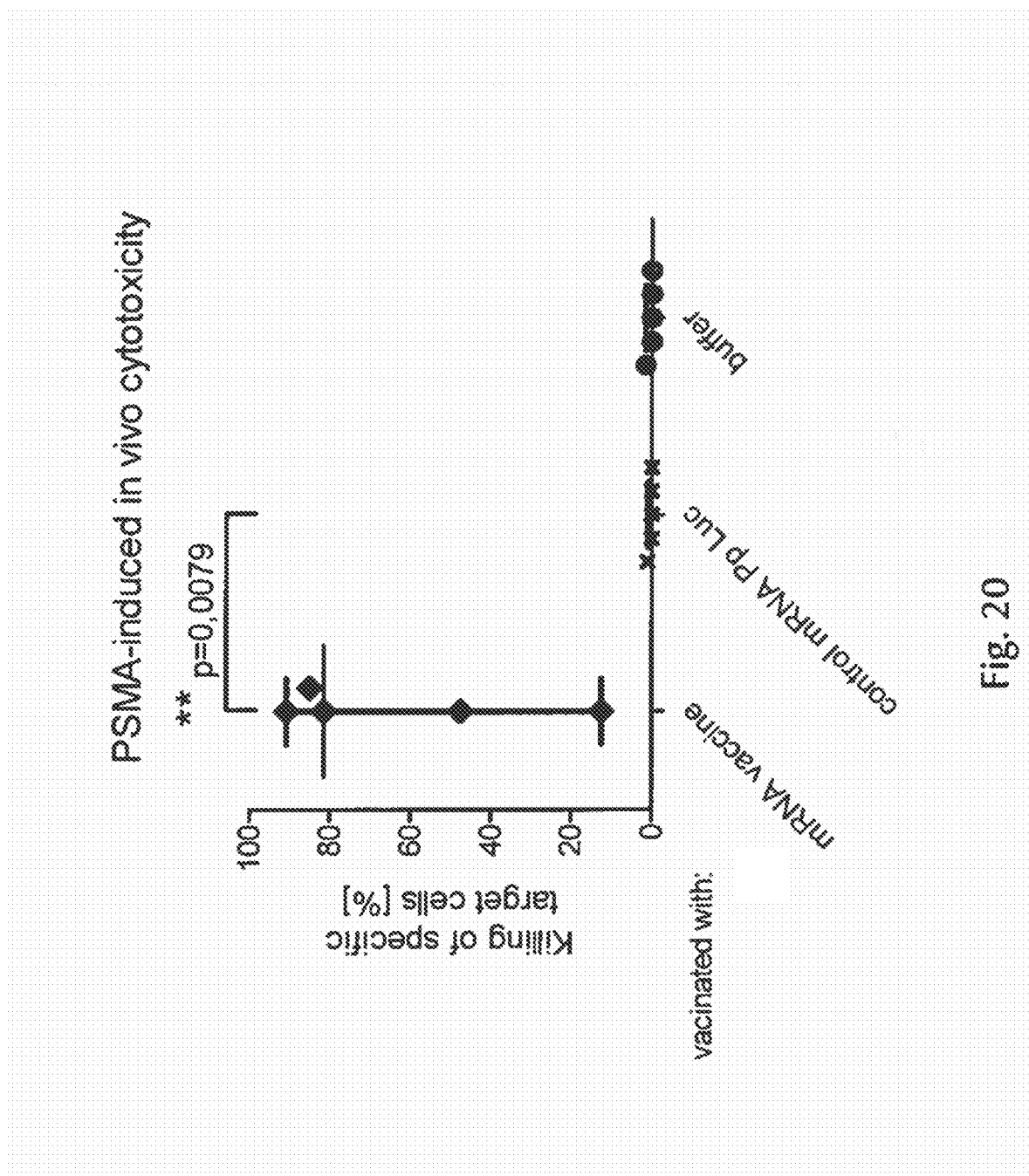

FIG. 19: shows the induction of PSMA-specific cytotoxic T cells. 5 mice per group were vaccinated either with the mRNA vaccine consisting of 4 components, each containing CC-optimized mRNAs coding for the human prostate differentiation antigens PSMA, STEAP, PSA and PSCA or with irrelevant mRNA (Pp Luc) formulated with protamine analog to the mRNA vaccine. Splenocytes from vaccinated and control mice were isolated at day 6 after last vaccination and stimulated either with PSMA-derived or with control peptide library. The secretion of IFN-γ was measured ex vivo using ELISPOT technique. Lines represent median values and range of 5 mice per group analyzed separately. Statistical analysis was performed with GraphPad Prism, p value was calculated with one-sided Mann-Whitney test FIG. 20. shows the induction of PSMA-specific cytotoxic T cells in vivo. C57BL/6 mice were vaccinated intradermally in three vaccination cycles with the mRNA vaccine consisting of 4 components, each containing GC-optimized mRNAs coding for the human prostate differentiation antigens PSMA, STEAP, PSA and PSCA. Control mice were vaccinated with control mRNA Pp Luc or treated with buffer (Ringer-lactate). At day 6, after last injection, $30 \times 10^6$ differentially labeled splenocytes (low and high population, loaded with PSMA-derived or control peptide library, mixed at the ratio of 1:1) were infused intravenously. 16 hours later splenocytes from recipient mice were isolated and analyzed by flow cytometry. The graph shows single data points for individual mice. Lines represent the median and range of values. 5 mice per group were analyzed. Statistical analysis was performed with GraphPad Prism, p value was calculated with Mann Whitney test.

Figure 21:
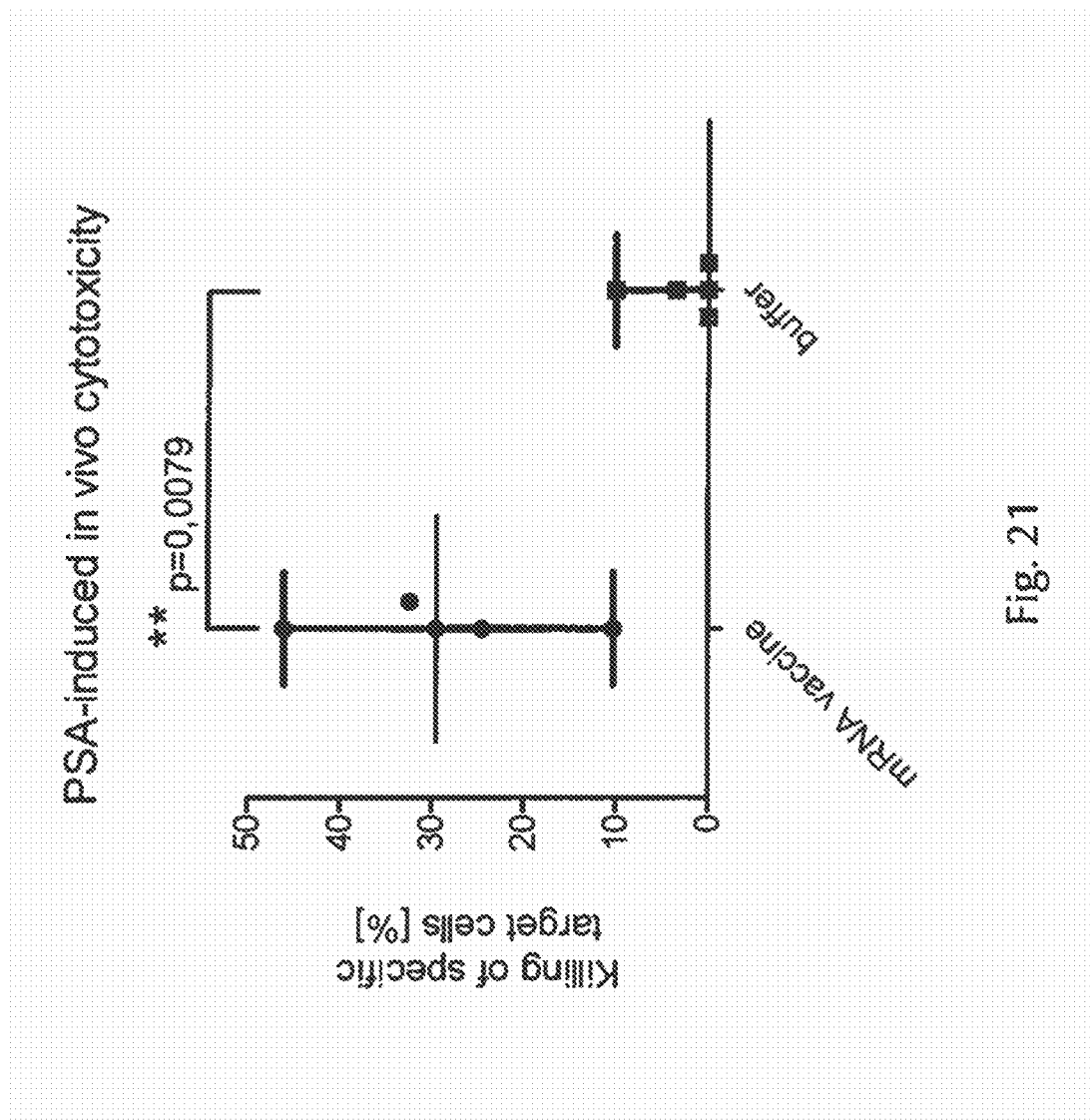

FIG. 21: shows the induction of PSA-specific memory cytotoxic T cells ten weeks after the last vaccination. C57BL/6 mice were vaccinated in two vaccination cycles with the mRNA vaccine consisting of 4 components, each containing GC-optimized mRNAs coding for the human prostate differentiation antigens PSMA, STEAP, PSA and PSCA. Control mice were treated with buffer (Ringer-lactate). 10 weeks after last injection, $30 \times 10^6$ differentially labeled splenocytes (low and high population, loaded with PSA-derived or control peptide library, mixed at the ratio of 1:1) were transplanted intravenously. 16 hours later splenocytes from recipient mice were isolated and analyzed by flow cytometry. The graph shows single data points and the lines represent median values from 6 mice per group analyzed separately. Statistical analysis was performed with GraphPad Prism, p value was calculated with Mann Whitney test.

Figure 22:
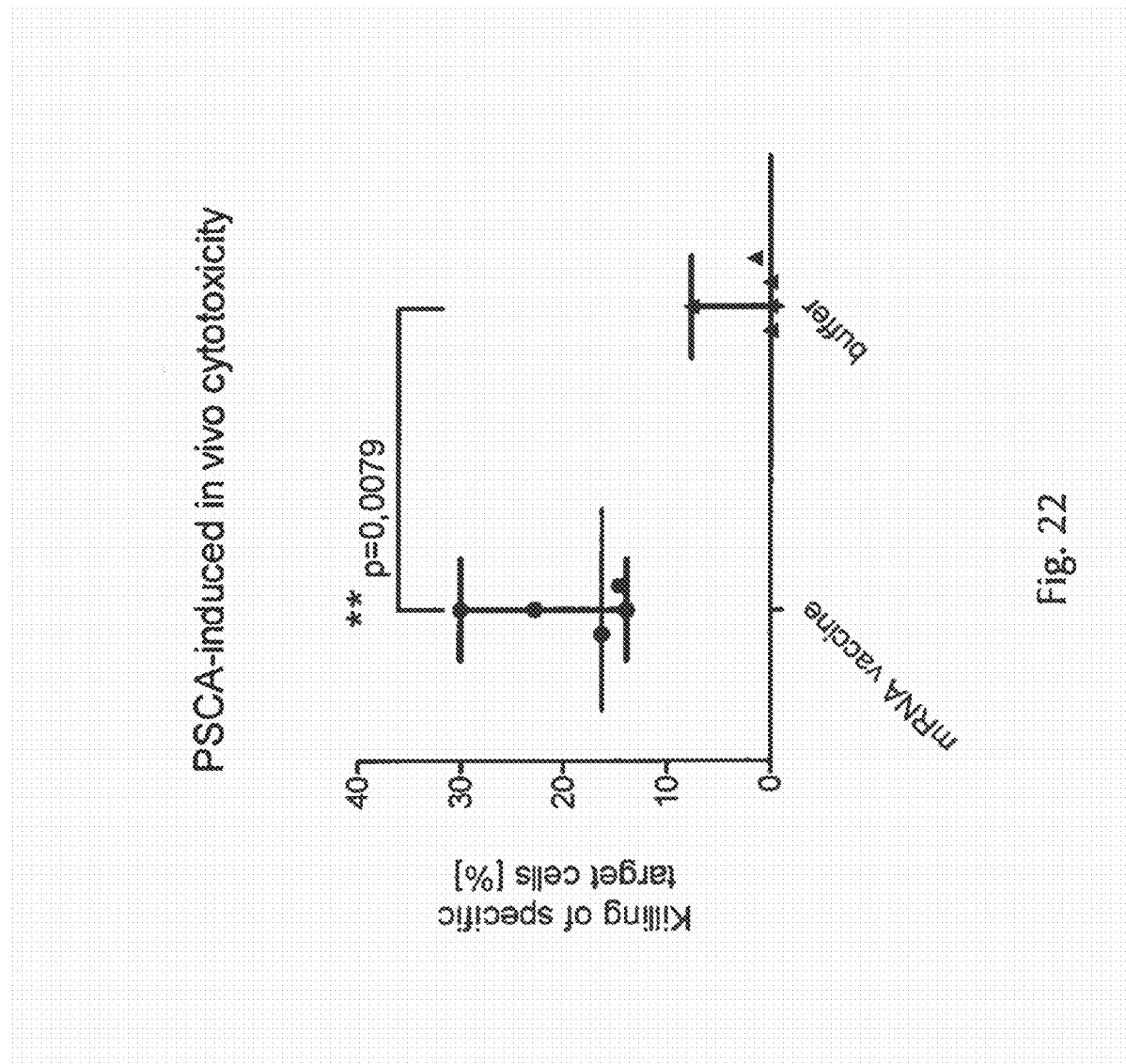

FIG. 22: shows the induction of PSCA-specific memory cytotoxic T cells ten weeks after the last vaccination. C57BL/6 mice were vaccinated in two vaccination cycles with the mRNA vaccine consisting of 4 components, each containing GC-optimized mRNAs coding for the human prostate differentiation antigens PSMA, STEAP, PSA and PSCA. Control mice were treated with buffer (Ringer-lactate). 10 weeks after last injection, $30 \times 10^6$ differentially labeled splenocytes (low and high population, loaded with PSCA-derived or control peptide library, mixed at the ratio of 1:1) were transplanted intravenously. 16 hours later splenocytes from recipient mice were isolated and analyzed by flow cytometry. The graph shows single data points and the lines represent median values from 6 mice per group analyzed separately. Statistical analysis was performed with GraphPad Prism, p value was calculated with Mann Whitney test.

FIG. 23: shows the inhibition of tumor growth in mice vaccinated with the mRNA vaccine consisting of 4 components, each containing GC-optimized mRNAs coding for the human prostate differentiation antigens PSMA, STEAP, PSA and PSCA. C57BL/6 mice were vaccinated intradermally in two vaccination cycles with the mRNA vaccine. Control mice were treated with buffer. 15 days post last vaccination mice were challenged subcutaneously with $1 \times 10^6$ syngenic TRAMP-C1 tumor cells. The tumor growth was monitored. Graph shows the logarithm of tumor volume measured at day 52 after tumor challenge. Statistical analysis was performed with GraphPad Prism, p value was calculated with Mann Whitney test.

EXAMPLES

The following examples are intended to illustrate the invention further. They are not intended to limit the subject matter of the invention thereto.

1. Preparation of Encoding Plasmids:

In the following experiment DNA sequences, corresponding to the respective mRNA sequences end encoding the antigens PSA (Prostate-Specific Antigen),
PSMA (Prostate-Specific Membrane Antigen),
PSCA (Prostate Stem Cell Antigen), and
STEAP (Six Transmembrane Epithelial Antigen of the Prostate), respectively, were prepared and used for in vitro transcription and transfection experiments. Thereby, the DNA sequence corresponding to the native antigen encoding mRNA (sequences comprising the coding sequences according to FIGS. 2, 5, 8 and 11, i.e. SEQ ID NOs: 2, 5, 8 and 11) were GC-optimized for a better codon-usage obtaining a sequence comprising the coding sequences according to FIGS. 3, 6, 9 and 12, i.e. SEQ ID NOs: 3, 6, 9 and 12. Then, the coding sequences was transferred into an GC-optimized construct (CureVac GmbH, Tübingen, Germany), which has been modified with a poly-A-tag and a poly-C-tag (A70-C30).

The final constructs were termed:
RNActive CAP-KLK3(GC)-muag-A70-C30 (SEQ ID NO: 1),
RNActive CAP-FOLH1(GC)-muag-A70-C30 (SEQ ID NO: 4),
RNActive CAP-PSCA(GC)-muag-A70-C30 (SEQ ID NO: 7), and
RNActive CAP-STEAP(GC)-muag-A70-C30 (SEQ ID NO: 10), respectively.

The final constructs comprise a sequence according to sequences as shown in FIGS. 1, 4, 7 and 10 (SEQ ID NOs: 1, 4, 7 and 10), respectively, which contain following sequence elements:
GC-optimized sequence for stabilization and a better codon usage
~70× Adenosin at the 3'-terminal end (poly-A-tail),
30× Cytosin at the 3'-terminal end (poly-C-tail);

2. In Vitro Transcription:

Based on the recombinant plasmid DNA obtained in Example 1 the RNA sequences were prepared by in vitro transcription. Therefore, the recombinant plasmid DNA was linearized and subsequently in vitro transcribed using the T7 RNA polymerase. The DNA template was then degraded by DNase I digestion, and the RNA was recovered by LiCl precipitation and further cleaned by HPLC extraction (PUREMessenger®, CureVac GmbH, Tübingen, Germany).

3. Complexation with Protamine

For transfection of the RNA into cells and organisms the RNA obtained by in vitro transcription was preferably complexed, more preferably with protamine upon mixing the RNA with protamine.

4. Immunization Experiments

For immunization the RNA obtained by the in vitro transcription experiment as shown above (see Experiment 2) was transfected into mice (Mice: C57 BL/6), preferably when complexed with protamine. Vaccination occurred in different groups, wherein one group (control group) mice was injected with buffer as control. 4 mice per group were immunized intradermally four times with 20 µg mRNA (5 µg per gene) complexed with protamine, wherein the RNA codes for PSA, PSMA, PSCA and STEAP.

5. Detection of an Antigen-Specific Immune Response (B-Cell Immune Response):

Detection of an antigen-specific immune response (B-cell immune response) was carried out by detecting antigen-specific antibodies. Therefore, blood samples were taken from the vaccinated mice one week after the last vaccination and sera were prepared. MaxiSorb plates (Nalgene Nunc International) were coated with human PSA protein (0.5 µg/well). After blocking with 1×PBS containing 0.05% Tween-20 and 1% BSA the plates were incubated with diluted mouse serum (1:30, 1.90, 1:270, 1:810). Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured.

As can be seen in FIG. 13, administration of an RNA-Mix, i.e. of an PCa-RNA cocktail comprising mRNA coding for PSA, PSMA, PSCA or STEAP, respectively, (sequences as shown in FIGS. 1, 4, 7 and 10 (SEQ ID NOs: 1, 4, 7 and 10), respectively) showed a significant induction of an antigen-specific immune response (B-cell immune response) due to significant formation of IgG2a antibodies against PSA in comparison to samples from control mice.

6. Detection of an Antigen-Specific Cellular Immune Response by ELISPOT:

2 months after the last vaccination mice were sacrificed, the spleens were removed and the splenocytes were isolated. The splenocytes were incubated for 7 days in presence of IL-4 to select dendritic cells. To determine an antigen-specific cellular immune response INFgamma secretion was measured after re-stimulation. As target cells splenocytes from a native mouse were used which were electroporated with the PCa-mRNA-cocktail (Mix) or with mRNA coding for PSA, PSMA, PSCA or STEAP (sequences as shown in FIGS. 1, 4, 7 and 10 (SEQ ID NOs: 1, 4, 7 and 10), respectively).

For detection of INFgamma a coat multiscreen plate (Millipore) was incubated overnight with coating buffer 0.1 M Carbonat-Bicarbonat Buffer pH 9.6, 10.59 g/l $Na_2CO_3$, 8.4 g/l $NaHCO_3$) comprising antibody against INFγ (BD Pharmingen, Heidelberg, Germany). Target cells and effector cells were incubated together in the plate in the ratio of 1:20 for 24 h. The plate was washed with 1×PBS and incubated with a biotin-coupled secondary antibody. After washing with 1×PBS/0.05% Tween-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually.

As can be seen in FIG. 14, vaccination of mice with the PCa-mRNA-cocktail coding for PSA, PSMA, PSCA or STEAP, (sequences as shown in FIGS. 1, 4, 7 and 10 (SEQ ID NOs: 1, 4, 7 and 10), respectively) leads to a significant induction of an antigen-specific immune response (CTL) against all four antigens due to significant formation of INF-gamma in comparison to native mice and mice vaccinated with buffer.

7. Tumor Challenge
  a) Immunization:
    20 µg mRNA (an PCa-RNA cocktail comprising 5 µg from mRNA coding for PSA, PSMA, PSCA and STEAP respectively, e.g. constructs RNActive CAP-KLK3 (GC)-muag-A70-C30, RNActive CAP-FOLH1 (GC)-muag-A70-C30, RNActive CAP-PSCA(GC)-muag-A70-C30, and RNActive CAP-STEAP(GC)-muag-A70-C30, respectively (sequences as shown in FIGS. 1, 4, 7 and 10, i.e. SEQ ID NOs: 1, 4, 7 and 10)) were injected intramuscularly in the mice. The immunization was repeated 1 or 3 times within 7 weeks. 40 days after the last immunization 1 Mio Tramp-C1 tumor cells were injected subcutaneously in the mice. Within 50 days tumor volume was determined.
  b) Results
    As could be seen in FIG. 15, the tumor volume is significantly reduced upon immunization with the PCa-RNA cocktail according to a) comprising mRNA coding for PSA, PSMA, PSCA and STEAP, respectively, 2× i.m. (intramuscularly). The tumor volume is even more reduced, when the PCa-RNA cocktail according to a) is administered 4× i.m. (intramuscularly).

8. Preparation of an mRNA Vaccine and Induction of Antigen-Specific Cytotoxic Antibodies and Antigen-Specific Cytotoxic T-Cells:

8.1 Preparation of an mRNA Vaccine:

The mRNA vaccine consists of GC-optimized mRNAs coding for the human prostate differentiation antigens PSMA, STEAP, PSA and PSCA (according to SEQ ID NOs: 3, 6, 9 and 12), each antigen formulated with the cationic peptide protamine at a mass ratio of 4:1 (RNA:protamine) dissolved in 80% (v/v) Ringer-lactate solution.

8.2 Vaccination

C57BL/6 mice were vaccinated intradermally with 64 µg (16 µg per antigen) of the mRNA vaccine as described under 8.1 above. Control mice were treated either with buffer (Ringer-lactate) or with irrelevant RNA (C-enriched mRNA coding for *Photinus pyralis* luciferase) formulated with protamine analog to the mRNA vaccine. Vaccination comprised two or three immunization cycles in week 1, 3, (and 7). Each cycle consisted of 4 injections on day 1, 2, 3 and 4 of the week.

8.3 Tumor Challenge 15 days after completion of vaccination, $1 \times 10^6$ TRAMP-C1 cells (transgenic adenocarcinoma of the mouse prostate cell line 1, expressing mouse homologues to human PSMA, PSCA and STEAP) per mouse were transplanted subcutaneously. Tumors were palpable 4 weeks after tumor cell inoculation. The tumor growth was monitored by measuring the tumor size with calipers.

8.4 Detection of Antigen-Specific Antibodies 14 days after the last vaccination, blood samples (200 µl) were taken retro-orbitally and serum was analyzed for the presence of antigen specific antibody subtypes IgG1 and IgG2a using the following ELISA protocol. 96-well ELISA plates were coated with recombinant protein PSCA or human purified PSA (both: 10 µg/ml in coating buffer) and (after blocking and washing) incubated with serum for 4 hours at 37° C. After incubation with biotin-labeled antibody against mouse IgG1 or IgG2a followed by incubation with HRP-Streptavidin, the TMB-substrate was added. The colorimetric reaction was measured at 450 nm using a Tecan ELISA reader.

8.5 ELISPOT—Detection of CTL (Cytotoxic T Cell) Responses

For the detection of CTL (cytotoxic T cell) responses the analysis of IFN-γ secretion in response to a specific stimulus can be visualized at a single cell level using the ELISPOT technique.

Splenocytes from mice vaccinated with the mRNA vaccine as described under 8.1 above and control mice were isolated 6 days after the last vaccination in the third vaccination cycle and then transferred into 96-well ELISPOT plates coated with an α-IFN-γ capture antibody. The cells were then stimulated for 24 hours at 37° C. either with a PSMA-derived peptide library or with a HIV-derived library as a control. Both libraries were used at a concentration of 1 µg/peptide/ml. After the incubation period the cells were washed out of the plate and the IFN-γ secreted by the cells was detected using a biotinylated secondary antibody against murine IFN-γ, followed by streptavidin-AKP. Spots were visualized using BCIP/NBT substrate and counted using an automated ELISPOT reader (Immunospot Analyzer, CTL Analyzers LLC).

8.6 In Vivo Cytotoxicity

To detect the activity of cytotoxic T cells in vivo lysis of specific target cells in the vaccinated and control mice was analyzed. The assay was performed one week as well as 10 weeks after last immunization to detect induction of memory cytotoxic T lymphocytes.

Splenocytes from naïve donor mice were isolated and labeled with two different concentrations of the fluorescent dye CFSE. Thereby two populations of high and low fluorescence intensity were created. Cells with low fluorescence were loaded for 3 hours at 37° C. with PSMA-, PSA- or PSCA-derived restricted peptide libraries (1 µg/ml/peptide). Control cells with high fluorescence were loaded with HIV Pol-derived peptide library (1 µg/ml/peptide) accordingly.

Both populations were mixed in cell:cell ratio of 1:1 and transplanted intravenously into naïve or vaccinated recipient mice. 16 hours later splenocytes from recipient mice were isolated and analyzed for the presence of fluorescent cells by flow cytometry. The shift of the ratio between low and high fluorescent cells in vaccinated mice represented the specific killing of target cells in vivo. An exact ratio between the number of observed specific target cells and observed control cells was estimated as a mean value in all control mice. This ratio allows a prediction of expected specific targets in vaccinated mice on the base of observed control cells. A ratio between observed and predicted number of specific target represent the percentage of remaining (non killed) specific targets.

The following rules were applied:

Ratio=specific targets (observed) in control mice/control targets (observed) in control mice Ratio×number of observed control targets in vaccinated mice=predicted number of specific targets in vaccinated mice % Killing=(1−(specific targets observed/specific targets predicted)

8.7 Statistical Analysis

Statistical analysis was performed using GraphPad Prism Software, Version 5.01. Due to the lack of normal distribution of the sample populations and the small sample size, non-parametric Mann Whitney tests were used to analyze the differences between the test groups with a significance level of 5%.

8.9 Results and Discussion

Mice were vaccinated with the mRNA vaccine consisting of GC-optimized mRNAs coding for the human prostate differentiation antigens PSMA, STEAP, PSA and PSCA each formulated separately with the cationic peptide protamine at a mass ratio of 4:1 (RNA:protamine). Control mice were treated either with buffer (Ringer-lactate) or with irrelevant RNA (Pp Luc) formulated with protamine analog to the mRNA vaccine.

a) Induction of Antigen-Specific Antibodies in Response to Vaccination with the mRNA Vaccine:

Restricted by the availability of recombinant protein required for the detection of antibodies the induction of specific antibodies for two of the four antigens was tested. For both analyzed proteins PSA and PSCA antigen specific antibodies in serum of mice vaccinated with the mRNA vaccine was detected demonstrating that both mRNAs are functional and immunogenic in vivo (see FIG. 16 to 18).

b) Induction of Antigen-Specific Cytotoxic T Cells in Response to Vaccination with the mRNA Vaccine:

Furthermore; the activation of cytotoxic T-cells in response to the administration of the mRNA vaccine was analyzed applying two independent functional assays: secretion of IFN-γ and in vivo cytotoxicity assay. IFN-γ is the main mediator of Th1 response and secreted by activated CTLs. Therefore, the presence of antigen-specific cytotoxic T-cells in splenocytes from vaccinated mice was investigated using ELISPOT technique. As an antigenic stimulus for splenocytes a restricted PSMA-derived peptide library was used. The stimulation with this library led to high IFN-γ secretion but only in splenocytes from mice vaccinated with the mRNA vaccine and not in control mice, vaccinated with mRNA coding for irrelevant protein luciferase (Pp Luc). None of the splenocytes reacted to the HIV-derived control peptide library (FIG. 19).

Antigen specific cellular immunity towards PSMA could be confirmed by an in vivo cytotoxicity assay. Specific killing of target cells loaded with a restricted PSMA-derived peptide library was observed in all five mice vaccinated with the mRNA vaccine, however the cytotoxic effect ranged between 12 and 90%. Mice vaccinated with control RNA (Pp Luc) or injection solution (Ringer-lactate buffer) were not able to eliminate infused target cells (see FIG. 20).

In another experiment it was investigated whether vaccination with the mRNA vaccine induces sustained memory effects in vivo. To address this point the presence of antigen-specific memory cytotoxic T cells was determined ten weeks after vaccination was completed by an in vivo cytotoxicity test. Specific killing of target cells was observed after vaccination for PSA as well as PSCA (FIG. 21-22). Taken together the mRNA vaccine induces sustained long lasting (at least 10 weeks) cellular immunity in mice.

Finally the ability of the mRNA vaccine to induce anti-tumor responses in mice was tested. To address this point we used the TRAMP-C1 tumor cell line. TRAMP-C1 expresses the mouse homologues to the human antigens PSMA, PSCA and STEAP included in the mRNA vaccine as antigen encoding mRNAs. Homology between mouse and man varies between 50-80% for the different antigens. Due to the fact that mice were vaccinated with mRNAs coding for human proteins, a protection against TRAMP-C1 tumor cells can only be mediated by cross-reactivity. As presented in FIG. 23 vaccination of mice with the mRNA vaccine mediated the protection against transplanted TRAMP-C1 tumor growth. This observation indicates the ability of the mRNA vaccine to induce cross-reactivity in mice.

SEQUENCE LISTING

```
<160> NUMBER OF SEQ ID NOS: 24

<210> SEQ ID NO 1
<211> LENGTH: 990
<212> TYPE: DNA
<213> ORGANISM: Artificial Sequence
<220> FEATURE:
<223> OTHER INFORMATION: Description of sequence: construct RNActiveII
      KLK3(GC) = PSA (see Figure 1)

<400> SEQUENCE: 1
gggagaaagc ttaccatgtg ggtgccggtc gtgttcctga ccctcagcgt gacgtggatc      60
ggcgccgcgc ccctgatcct gtcgcggatc gtgggggggct gggagtgcga gaagcacagc     120
cagccctggc aggtgctggt ggccagccgc ggccgggccg tgtgcggcgg cgtgctggtg     180
cacccccagt gggtgctgac cgccgcccac tgcatccgga caagagcgt catcctgctg     240 ggccggcaca gcctgttcca ccccgaggac accggccagg tgttccaggt gagccacagc     300
ttcccccacc ccctgtacga catgagcctc ctgaagaacc ggttcctgcg gcccggcgac     360
gacagcagcc acgacctgat gctgctgcgg ctgagcgagc ccgccgagct gaccgacgcc     420
gtgaaggtga tggacctgcc gacccaggag cccgccctgg gcaccacctg ctacgccagc     480
ggctggggga gcatcgagcc cgaggagttc ctcaccccca agaagctgca gtgcgtggac     540
ctgcacgtga tcagcaacga cgtgtgcgcc caggtgcacc cccagaaggt gaccaagttc     600
atgctgtgcg ccggccggtg gaccggcggc aagagcacct gcagcggcga cagcggcggc     660
cccctggtct gcaacggcgt gctgcagggc atcaccagct ggggcagcga gccctgcgcc     720
ctgcccgagc gccccagcct gtacaccaag gtggtgcact accggaagtg gatcaaggac     780
accatcgtgg ccaacccgtg accactagtt ataagactga ctagcccgat gggcctccca     840
acgggccctc ctcccctcct tgcaccgaga ttaataaaaa aaaaaaaaaa aaaaaaaaaa     900
aaaaaaaaaa aaaaaaaaaa aaaaaaaaaa aaaaaaaat attcccccccc cccccccccc     960 cccccccccc ccctctagac aattggaatt                                     990

<210> SEQ ID NO 2
<211> LENGTH: 786
<212> TYPE: DNA
<213> ORGANISM: Artificial Sequence
<220> FEATURE:
<223> OTHER INFORMATION: Description of sequence: construct CDS
      KLK3(wt) = PSA (see Figure 2)

<400> SEQUENCE: 2
```

| | |
|---|---|
| atgtgggtcc cggttgtctt cctcaccctg tccgtgacgt ggattggtgc tgcacccctc | 60 |
| atcctgtctc ggattgtggg aggctgggag tgcgagaagc attcccaacc ctggcaggtg | 120 |
| cttgtggcct ctcgtggcag ggcagtctgc ggcggtgttc tggtgcaccc ccagtgggtc | 180 |
| ctcacagctg cccactgcat caggaacaaa agcgtgatct tgctgggtcg gcacagcctg | 240 |
| tttcatcctg aagacacagg ccaggtattt caggtcagcc acagcttccc acaccgctc | 300 |
| tacgatatga gcctcctgaa gaatcgattc ctcaggccag gtgatgactc cagccacgac | 360 |
| ctcatgctgc tccgcctgtc agagcctgcc gagctcacgg atgctgtgaa ggtcatggac | 420 |
| ctgcccaccc aggagccagc actgggacc acctgctacg cctcaggctg ggcagcatt | 480 |
| gaaccagagg agttcttgac cccaaagaaa cttcagtgtg tggacctcca tgttatttcc | 540 |
| aatgacgtgt gtgcgcaagt tcaccctcag aaggtgacca agttcatgct gtgtgctgga | 600 |
| cgctggacag ggggcaaaag cacctgctcg ggtgattctg ggggcccact tgtctgtaat | 660 |
| ggtgtgcttc aaggtatcac gtcatggggc agtgaaccat gtgccctgcc cgaaaggcct | 720 |
| tccctgtaca ccaaggtggt gcattaccgg aagtggatca aggacaccat cgtggccaac | 780 |
| ccctga | 786 |

<210> SEQ ID NO 3
<211> LENGTH: 786
<212> TYPE: DNA
<213> ORGANISM: Artificial Sequence
<220> FEATURE:
<223> OTHER INFORMATION: Description of sequence: construct
      CDS KLK3(GC) = PSA (see Figure 3)

<400> SEQUENCE: 3

| | |
|---|---|
| atgtgggtgc ccgtcgtgtt cctgaccctc agcgtgacct ggatcggcgc cgccccgctg | 60 |
| atcctgtccc ggatcgtcgg gggctgggag tgcgagaagc acagccagcc ctggcaggtg | 120 |
| ctcgtggcgt cccgcgggcg ggccgtctgc ggcggggtgc tggtgcaccc ccagtgggtc | 180 |
| ctgacggccg cccactgcat ccgcaacaag agcgtgatcc tcctgggccg gcactccctg | 240 |
| ttccaccccg aggacaccgg ccaggtgttc caggtcagcc actccttccc gcacccctc | 300 |
| tacgacatga gcctgctgaa gaaccgcttc ctccggcccg ggacgactc cagccacgac | 360 |
| ctgatgctgc tccgcctgtc cgagcccgcc gagctgaccg acgcggtgaa ggtgatggac | 420 |
| ctcccgaccc aggagcccgc cctgggcacg acctgctacg ccagcgggtg gggctccatc | 480 |
| gagcccgagg agttcctgac ccccaagaag ctccagtgcg tcgacctgca cgtgatcagc | 540 |
| aacgacgtgt gcgcccaggt ccaccccgcag aaggtgacca agttcatgct gtgcgcgggg | 600 |
| cggtggacgg gcggcaagtc cacctgcagc ggggactccg gcgggcccct cgtgtgcaac | 660 |
| ggcgtcctgc agggcatcac cagctggggg tccgagccct cgccctgcc cgagcgcccg | 720 |
| agcctctaca ccaaggtggt gcactaccgg aagtggatca aggacacgat cgtcgccaac | 780 |
| ccctga | 786 |

<210> SEQ ID NO 4
<211> LENGTH: 2457
<212> TYPE: DNA
<213> ORGANISM: Artificial Sequence
<220> FEATURE:
<223> OTHER INFORMATION: Description of sequence: construct RNActiveII
      FOLH1(GC) = PSMA (see Figure 4)

<400> SEQUENCE: 4

| | |
|---|---|
| gggagaaagc ttaccatgtg gaacctgctc cacgagaccg acagcgccgt ggcgacggcc | 60 |

```
cggcgcccgc ggtggctgtg cgccggcgcc ctggtcctgg ccgggggctt cttcctgctg      120
ggcttcctgt tcggctggtt catcaagtcg agcaacgagg ccaccaacat cacccccaag      180
cacaacatga aggccttcct cgacgagctg aaggccgaga acatcaagaa gttcctgtac      240
aacttcaccc cagatcccca cctggccggg accgagcaga acttccagct ggccaagcag      300
atccagagcc agtggaagga gttcggcctg gactcggtgg agctggcgca ctacgacgtg      360
ctgctcagct accccaacaa gacccacccc aactacatca gcatcatcaa cgaggacggc      420
aacgagatct tcaacaccag cctgttcgag ccccgccc ccggctacga gaacgtgtcg       480
gacatcgtgc cccccttcag cgccttcagc ccgcagggca tgcccgaggg ggacctggtg      540
tacgtgaact acgcccggac ggaggacttc ttcaagctgg agcgcgacat gaagatcaac      600
tgcagcggca agatcgtgat cgcccggtac ggcaaggtgt ccggggcaa caaggtgaag       660 aacgcccagc tggccggggc caagggcgtg atcctgtact cggaccccgc cgactacttc      720
gcccccggcg tgaagagcta ccccgacggc tggaacctgc ccggcggggg cgtccagcgc      780
ggcaacatcc tcaacctgaa cggcgccggc gacccgctga ccccggta ccccgcgaac        840 gagtacgcct accggcgggg catcgccgag gccgtgggcc tgcccagcat ccccgtgcac      900
ccgatcggct actacgacgc ccagaagctg ctggagaaga tgggcgggag cgccccgccc      960
gactcgagct ggcggggcag cctgaaggtg ccctacaacg tgggcccgg cttcaccggg       1020 aacttctcga cccagaaggt gaagatgcac atccacagca ccaacgaggt gacccgcatc      1080
tacaacgtga tcggcaccct gcggggcgcc gtggagcccg accggtacgt gatcctcggc      1140
gggcaccgcg acagctgggt gttcggcggc atcgacccc agagcggcgc cgccgtggtc       1200
cacgagatcg tgcggtcgtt cggcacccta aagaaggagg ggtggcggcc ccgccggacg      1260
atcctgttcg ccagctggga cgcggaggag ttcggcctgc tgggcagcac cgagtgggcc      1320
gaggagaaca gccggctgct gcaggagcgg ggcgtggcct acatcaacgc cgactcgagc      1380
atcgagggca actacaccct ccgcgtggac tgcacccccgc tgatgtacag cctggtgcac      1440
aacctgacca aggagctgaa gagccccgac gagggggttcg agggcaagtc gctgtacgag      1500
agctggacca agaagagccc ctcgcccgag ttcagcggca tgccccggat cagcaagctg      1560
ggcagcggga acgacttcga ggtgttcttc cagcggctgg gcatcgcctc gggccgcgcc      1620
cggtacacca agaactggga gacgaacaag ttcagcggct accccctcta ccacagcgtg      1680
tacgagacct acgagctggt ggagaagttc tacgacccca tgttcaagta ccacctgacc      1740
gtggcccagg tgcggggcgg gatggtgttc gagctggcca cagcatcgt gctgcccttc       1800 gactgccgcg actacgccgt cgtgctgcgg aagtacgccg acaagatcta ctcgatcagc      1860
atgaagcacc ccaggagat gaagacctac agcgtgagct cgactcgct gttcagcgcg        1920 gtgaagaact tcaccgagat cgccagcaag ttctcggagc ggctccagga cttcgacaag      1980
agcaacccga tcgtgctgcg catgatgaac gaccagctga tgttcctgga gcgggccttc      2040 atcgacccc tgggcctgcc cgaccggccc ttctaccggc acgtgatcta cgcccccagc       2100
agccacaaca agtacgccgg cgagtcgttc ccggggatct acgacgccct gttcgacatc      2160
gagagcaagg tggaccccag caaggcctgg ggcgaggtga gcgccagat ctacgtggcc       2220 gccttcaccg tgcaggccgc ggccgagacc ctgagcgagg tggcctgacc actagttata      2280
agactgacta gcccgatggg cctcccaacg ggccctcctc ccctccttgc accgagatta      2340
ataaaaaaaa aaaaaaaaaa aaaaaaaaaa aaaaaaaaaa aaaaaaaaaa aaaaaaaaaa      2400
```

```
aaaaaatatt cccccccccc cccccccccc cccccccccc tctagacaat tggaatt        2457
```

<210> SEQ ID NO 5
<211> LENGTH: 2253
<212> TYPE: DNA
<213> ORGANISM: Artificial Sequence
<220> FEATURE:
<223> OTHER INFORMATION: Description of sequence: construct CDS
      FOLH1(wt) = PSMA (see Figure 5)

<400> SEQUENCE: 5

```
atgtggaatc tccttcacga aaccgactcg gctgtggcca ccgcgcgccg cccgcgctgg          60
ctgtgcgctg gggcgctggt gctggcgggt ggcttctttc cctcggctt cctcttcggg         120
tggtttataa atcctccaa tgaagctact aacattactc aaagcataa tatgaaagca          180
tttttggatg aattgaaagc tgagaacatc aagaagttct tatataattt tacacagata        240
ccacatttag caggaacaga acaaaacttt cagcttgcaa agcaaattca atcccagtgg        300
aaagaatttg gcctggattc tgttgagcta gcacattatg atgtcctgtt gtcctaccca        360
aataagactc atcccaacta catctcaata attaatgaag atggaaatga ttttcaac         420
acatcattat ttgaaccacc tcctccagga tatgaaaatg ttcggatat tgtaccacct         480
ttcagtgctt tctctcctca aggaatgcca gagggcgatc tagtgtatgt taactatgca        540
cgaactgaag acttctttaa attggaacgg gacatgaaaa tcaattgctc tgggaaaatt        600
gtaattgcca gatatgggaa agtttttcaga ggaaataagg ttaaaaatgc ccagctggca       660
ggggccaaag gagtcattct ctactccgac cctgctgact actttgctcc tgggggtgaag      720
tcctatccag atggttggaa tcttcctgga ggtggtgtcc agcgtggaaa tatcctaaat       780
ctgaatggtg caggagaccc tctcacacca ggttacccag caaatgaata tgcttatagg        840
cgtggaattg cagaggctgt tggtcttcca agtattcctg ttcatccaat tggatactat       900
gatgcacaga agctcctaga aaaaatgggt ggctcagcac accagatag cagctggaga        960
ggaagtctca aagtgcccta caatgttgga cctggcttta ctggaaactt ttctacacaa      1020
aaagtcaaga tgcacatcca ctctaccaat gaagtgacaa gaatttacaa tgtgataggt      1080
actctcagag gagcagtgga accagacaga tatgtcattc tgggaggtca ccgggactca      1140
tgggtgtttg gtggtattga ccctcagagt ggagcagctg ttgttcatga aattgtgagg      1200
agctttggaa cactgaaaaa ggaagggtgg agacctagaa gaacaatttt gtttgcaagc      1260
tgggatgcag aagaatttgg tcttcttggt tctactgagt gggcagagga gaattcaaga      1320
ctccttcaag agcgtggcgt ggcttatatt aatgctgact catctataga aggaaactac      1380
actctgagag ttgattgtac accgctgatg tacagcttgg tacacaacct aacaaaagag      1440
ctgaaaagcc ctgatgaagg ctttgaaggc aaatctcttt atgaaagttg gactaaaaaa      1500
agtccttccc cagagttcag tggcatgccc aggataagca aattgggatc tggaaatgat     1560
tttgaggtgt tcttccaacg acttggaatt gcttcaggca gagcacggta tactaaaaat     1620
tgggaaacaa acaaattcag cggctatcca ctgtatcaca gtgtctatga acatatgag      1680
ttggtggaaa agtttatga tccaatgttt aaatatcacc tcactgtggc ccaggttcga      1740
ggagggatgg tgtttgagct agccaattcc atagtgctcc ttttgattg tcgagattat      1800
gctgtagttt taagaaagta tgctgacaaa atctacagta tttctatgaa acatccacag      1860
gaaatgaaga catacagtgt atcatttgat tcacttttt ctgcagtaaa gaattttaca      1920
gaaattgctt ccaagttcag tgagagactc caggactttg acaaaagcaa cccaatagta      1980
```

| | |
|---|---:|
| ttaagaatga tgaatgatca actcatgttt ctggaaagag catttattga tccattaggg | 2040 |
| ttaccagaca ggccttttta taggcatgtc atctatgctc caagcagcca caacaagtat | 2100 |
| gcagggagt cattcccagg aatttatgat gctctgtttg atattgaaag caaagtggac | 2160 |
| ccttccaagg cctggggaga agtgaagaga cagatttatg ttgcagcctt cacagtgcag | 2220 |
| gcagctgcag agactttgag tgaagtagcc taa | 2253 |

<210> SEQ ID NO 6
<211> LENGTH: 2253
<212> TYPE: DNA
<213> ORGANISM: Artificial Sequence
<220> FEATURE:
<223> OTHER INFORMATION: Description of sequence: construct
      CDS FOLH1(GC) = PSMA (see Figure 6)

<400> SEQUENCE: 6

| | |
|---|---:|
| atgtggaacc tgctccacga gaccgacagc gccgtggcca ccgcgcggcg ccccggtgg | 60 |
| ctgtgcgccg cgccctggt cctcgccggg ggcttcttcc tgctgggtt cctcttcggc | 120 |
| tggttcatca gtccagcaa cgaggccacg aacatcaccc cgaagcacaa catgaaggcg | 180 |
| ttcctggacg agctgaaggc cgagaacatc aagaagttcc tctacaactt cacccagatc | 240 |
| ccccacctgg ccgggaccga gcagaacttc cagctggcca agcagatcca gtcccagtgg | 300 |
| aaggagttcg gcctcgacag cgtggagctg gcgcactacg acgtgctgct ctcctacccc | 360 |
| aacaagacgc accccaacta catcagcatc atcaacgagg acggcaacga gatcttcaac | 420 |
| acctccctgt tcgagccgcc cccccccggg tacgagaacg tcagcgacat cgtgccgccc | 480 |
| ttctccgcct tcagccccca gggcatgccc gagggggacc tggtgtacgt caactacgcc | 540 |
| cgcaccgagg acttcttcaa gctcgagcgg gacatgaaga tcaactgctc cggcaagatc | 600 |
| gtgatcgccc gctacgggaa ggtgttccgg ggcaacaagg tcaagaacgc ccagctggcg | 660 |
| ggcgccaagg gggtgatcct gtacagcgac ccggccgact acttcgcccc cggcgtgaag | 720 |
| tcctaccccg acggtggaa cctccccggc ggcgggtcc agcgcggcaa catcctgaac | 780 |
| ctgaacgggg ccggcgaccc gctcacccc gggtacccg cgaacgagta cgcctaccgg | 840 |
| cgcggcatcg ccgaggccgt gggcctgccc agcatcccgg tgcaccccat cgggtactac | 900 |
| gacgcccaga gctgctcga gaagatgggc gggtccgcgc ccccgacag ctcctggcgg | 960 |
| ggcagcctga aggtcccgta caacgtgggg ccggcttca gggcaacttc tccacccag | 1020 |
| aaggtgaaga tgcacatcca cagcaccaac gaggtcaccc gcatctacaa cgtgatcggg | 1080 |
| acgctgcggg gcgccgtgga gcccgaccgc tacgtcatcc tcggggggcca ccgggacagc | 1140 |
| tgggtgttcg ggggcatcga ccccagtcc ggcgccgccg tggtccacga atcgtgcgc | 1200 |
| agcttcggga ccctgaagaa ggaggctgg cggccgcgcc ggaccatcct gttcgcctcc | 1260 |
| tgggacgcgg aggagttcgg gctcctgggc agcaccgagt gggccgagga aactcccgc | 1320 |
| ctgctccagg agcggggcgt cgcctacatc aacgccgaca gctccatcga ggggaactac | 1380 |
| acgctgcgcg tggactgcac cccgctgatg tacagcctcg tgcacaacct gaccaaggag | 1440 |
| ctgaagtccc ccgacgaggg cttcgagggg aagagcctct acgagtcctg gaccaagaag | 1500 |
| agcccgtccc ccgagttcag cggcatgccc cggatctcca agctgggag cggcaacgac | 1560 |
| ttcgaggtct tcttccagcg gctgggcatc gcgtccggc gcgccggta cacgaagaac | 1620 |
| tgggagacca caagttcag cggctacccc tctctaccact ccgtgtacga gacctacgag | 1680 |
| ctggtggaga gttctacga cccgatgttc aagtaccacc tgaccgtcgc ccaggtgcgc | 1740 |

```
ggggcatgg tgttcgagct ggccaacagc atcgtcctcc ccttcgactg ccgggactac    1800
gccgtggtgc tgcgcaagta cgcggacaag atctacagca tctccatgaa gcaccccag    1860 gagatgaaga cgtacagcgt ctccttcgac agcctgttct ccgccgtgaa gaacttcacc    1920
gagatcgcca gcaagttctc cgagcggctc caggacttcg acaagagcaa ccccatcgtg    1980
ctgcgcatga tgaacgacca gctgatgttc ctcgagcggg ccttcatcga cccgctgggg    2040
ctgcccgacc gccccttcta ccggcacgtc atctacgccc cctccagcca acaagtac     2100 gcgggcgagt ccttcccggg gatctacgac gccctcttcg acatcgagag caaggtggac    2160
ccctccaagg cctggggcga ggtgaagcgc cagatctacg tcgccgcctt caccgtgcag    2220
gcggccgccg agaccctgag cgaggtggcc tga                               2253

<210> SEQ ID NO 7
<211> LENGTH: 576
<212> TYPE: DNA
<213> ORGANISM: Artificial Sequence
<220> FEATURE:
<223> OTHER INFORMATION: Description of sequence: construct RNActiveII
      PSCA(GC) (see Figure 7)

<400> SEQUENCE: 7
gggagaaagc ttaccatgaa ggccgtgctg ctcgcgctgc tgatggccgg cctggccctg    60
cagccgggga ccgccctgct gtgctacagc tgcaaggccc aggtctcgaa cgaggactgc    120
ctgcaggtgg agaactgcac gcagctgggc gagcagtgct ggaccgcccg gatccgcgcc    180
gtgggcctgc tcaccgtgat cagcaagggc tgcagcctga actgcgtgga cgacagccag    240
gactactacg tgggcaagaa gaacatcacc tgctgcgaca ccgacctgtg caacgccagc    300
ggcgcccacg ccctgcagcc gcggccgccg atcctggccc tgctgcccgc ctgggcctg    360 ctgctctggg gccccggcca gctgtgacca ctagttataa gactgactag cccgatgggc    420
ctcccaacgg gccctcctcc cctccttgca ccgagattaa taaaaaaaaa aaaaaaaaaa    480
aaaaaaaaaa aaaaaaaaaa aaaaaaaaa aaaaaaaaa aaaatattc cccccccccc    540 cccccccccc cccccccct ctagacaatt ggaatt                             576

<210> SEQ ID NO 8
<211> LENGTH: 372
<212> TYPE: DNA
<213> ORGANISM: Artificial Sequence
<220> FEATURE:
<223> OTHER INFORMATION: Description of sequence: construct CDS PSCA(wt)
      (see Figure 8)

<400> SEQUENCE: 8
atgaaggctg tgctgcttgc cctgttgatg gcaggcttgg ccctgcagcc aggcactgcc    60
ctgctgtgct actcctgcaa agcccaggtg agcaacgagg actgcctgca ggtggagaac    120
tgcacccagc tgggggagca gtgctggacc gcgcgcatcc gcgcagttgg cctcctgacc    180
gtcatcagca aaggctgcag cttgaactgc gtggatgact cacaggacta ctacgtgggc    240
aagaagaaca tcacgtgctg tgacaccgac ttgtgcaacg ccagcggggc ccatgccctg    300
cagccggctg ctgccatcct tgcgctgctc cctgcactcg gcctgctgct ctggggaccc    360
ggccagctct ag                                                       372

<210> SEQ ID NO 9
<211> LENGTH: 372
<212> TYPE: DNA
<213> ORGANISM: Artificial Sequence
```

```
<220> FEATURE:
<223> OTHER INFORMATION: Description of sequence: construct CDS PSCA(GC)
      (see Figure 9)

<400> SEQUENCE: 9
atgaaggccg tgctgctcgc cctgctgatg gcgggcctcg ccctgcagcc cgggaccgcc      60
ctgctctgct acagctgcaa ggcccaggtc tccaacgagg actgcctgca ggtggagaac     120
tgcacccagc tgggcgagca gtgctggacg gcccggatcc gcgcgtgggg gctcctgacc     180
gtcatcagca agggctgctc cctgaactgc gtggacgaca gccaggacta ctacgtgggg     240
aagaagaaca tcacctgctg cgacaccgac ctctgcaacg cctccggcgc ccacgccctg     300
cagccggcgg ccgccatcct ggccctcctg cccgccctgg gcctcctgct gtggggcgcc     360
ggccagctct ga                                                          372

<210> SEQ ID NO 10
<211> LENGTH: 1224
<212> TYPE: DNA
<213> ORGANISM: Artificial Sequence
<220> FEATURE:
<223> OTHER INFORMATION: Description of sequence: construct RNActive II
      STEAP (GC) = STEAP1 (see Figure 10)

<400> SEQUENCE: 10
gggagaaagc ttaccatgga gagccggaag gacatcacca accaggagga gctgtggaag      60
atgaagccgc gccggaacct cgaggaggac gactacctgc acaaggacac gggcgagacc     120
tcgatgctga agcggcccgt gctcctgcac ctgcaccaga ccgcccacgc ggacgagttc     180
gactgcccga gcgagctcca gcacacgcag gagctgttcc cgcagtggca cctgcccatc     240
aagatcgccg ccatcatcgc gagcctcacc ttcctgtaca ccctgctccg cgaggtcatc     300
cacccgctgg ccacgtcgca ccagcagtac ttctacaaga tcccgatcct ggtgatcaac     360
aaggtgctcc ccatggtcag catcaccctg ctggccctcg tgtacctgcc ggggtgatc     420 gcggccatcg tccagctgca caacggcacc aagtacaaga agttcccgca ctggctcgac     480
aagtggatgc tgacgcggaa gcagttcggc ctgctcagct tcttcttcgc cgtgctgcac     540
gcgatctact cgctgagcta ccccatgcgg cgcagctacc ggtacaagct cctgaactgg     600
gcctaccagc aggtgcagca gaacaaggag gacgcctgga tcgagcacga cgtctggcgg     660
atggagatct acgtgtcgct ggggatcgtg ggcctcgcga tcctggccct gctcgccgtc     720
accagcatcc cgagcgtgtc ggacagcctg acctggcgcg agttccacta catccagagc     780
aagctgggca tcgtgtcgct cctgctgggg acgatccacg cgctcatctt cgcctggaac     840
aagtggatcg acatcaagca gttcgtctgg tacaccccgc ccaccttcat gatcgccgtg     900
ttcctgccga tcgtggtcct gatcttcaag agcatcctct tcctgccgtg cctgcggaag     960
aagatcctca agatccggca cggctgggag gacgtgacga agatcaacaa gaccgagatc    1020
tgcagccagc tgtgaccact agttataaga ctgactagcc cgatgggcct cccaacgggc    1080
cctcctcccc tccttgcacc gagattaata aaaaaaaaa aaaaaaaaa aaaaaaaaa       1140 aaaaaaaaa aaaaaaaaa aaaaaaaaa aaatattccc cccccccccc cccccccccc       1200
ccccccctct agacaattgg aatt                                            1224

<210> SEQ ID NO 11
<211> LENGTH: 1020
<212> TYPE: DNA
<213> ORGANISM: Artificial Sequence
<220> FEATURE:
```

<223> OTHER INFORMATION: Description of sequence: construct CDS
      STEAP(wt) = STEAP1 (see Figure 11)

<400> SEQUENCE: 11

| | |
|---|---|
| atggaaagca gaaaagacat cacaaaccaa gaagaacttt ggaaaatgaa gcctaggaga | 60 |
| aatttagaag aagacgatta tttgcataag gacacgggag agaccagcat gctaaaaga | 120 |
| cctgtgcttt tgcatttgca ccaaacagcc catgctgatg aatttgactg cccttcagaa | 180 |
| cttcagcaca cacaggaact ctttccacag tggcacttgc caattaaaat agctgctatt | 240 |
| atagcatctc tgactttct ttacactctt ctgagggaag taattcaccc tttagcaact | 300 |
| tcccatcaac aatattttta taaaattcca atcctggtca tcaacaaagt cttgccaatg | 360 |
| gtttccatca ctctcttggc attggtttac ctgccaggtg tgatagcagc aattgtccaa | 420 |
| cttcataatg gaaccaagta taagaagttt ccacattggt tggataagtg gatgttaaca | 480 |
| agaaagcagt ttgggcttct cagtttcttt tttgctgtac tgcatgcaat ttatagtctg | 540 |
| tcttacccaa tgaggcgatc ctacagatac aagttgctaa actgggcata tcaacaggtc | 600 |
| caacaaaata agaagatgc ctggattgag catgatgttt ggagaatgga gatttatgtg | 660 |
| tctctgggaa ttgtgggatt ggcaatactg gctctgttgg ctgtgacatc tattccatct | 720 |
| gtgagtgact ctttgacatg gagagaattt cactatattc agagcaagct aggaattgtt | 780 |
| tcccttctac tggcacaat acacgcattg attttgcct ggaataagtg gatagatata | 840 |
| aaacaatttg tatggtatac acctccaact tttatgatag ctgttttcct tccaattgtt | 900 |
| gtcctgatat ttaaaagcat actattcctg ccatgcttga ggaagaagat actgaagatt | 960 |
| agacatggtt gggaagacgt caccaaaatt aacaaaactg agatatgttc ccagttgtag | 1020 |

<210> SEQ ID NO 12
<211> LENGTH: 1020
<212> TYPE: DNA
<213> ORGANISM: Artificial Sequence
<220> FEATURE:
<223> OTHER INFORMATION: Description of sequence: construct CDS
      STEAP(GC) = STEAP1 (see Figure 12)

<400> SEQUENCE: 12

| | |
|---|---|
| atggagagcc ggaaggacat caccaaccag gaggagctgt ggaagatgaa gccccgccgg | 60 |
| aacctcgagg aggacgacta cctgcacaag gacaccggcg agacgtccat gctgaagcgc | 120 |
| ccggtgctcc tgcacctgca ccagaccgcc cacgccgacg agttcgactg ccccagcgag | 180 |
| ctccagcaca cccaggagct gttcccccag tggcacctgc ccatcaagat cgcggccatc | 240 |
| atcgcctccc tcaccttcct gtacacgctg ctccgggagg tcatccaccc gctggccacc | 300 |
| agccaccagc agtacttcta caagatcccc atcctggtga tcaacaaggt gctccccatg | 360 |
| gtctccatca ccctgctggc cctcgtgtac ctgcccgggg tgatcgcggc catcgtccag | 420 |
| ctgcacaacg gcaccaagta caagaagttc ccgcactggc tcgacaagtg gatgctgacg | 480 |
| cgcaagcagt tcgggctgct cagcttcttc ttcgccgtgc tgcacgccat ctactccctg | 540 |
| agctacccca tgcggcgctc ctaccggtac aagctcctga actgggcgta ccagcaggtg | 600 |
| cagcagaaca aggaggacgc ctggatcgag cacgacgtct ggcgcatgga gatctacgtg | 660 |
| agcctgggca tcgtggggct cgccatcctg gccctgctcg ccgtcacctc catccccagc | 720 |
| gtgtccgaca gcctgacctg gcgggagttc cactacatcc agtccaagct gggcatcgtg | 780 |
| agcctcctgc tggcaccat ccacgcgctc atcttcgcct ggaacaagtg gatcgacatc | 840 |
| aagcagttcg tctggtacac gcccccgacc ttcatgatcg ccgtgttcct gcccatcgtg | 900 |

```
gtcctgatct tcaagtccat cctcttcctg ccctgcctgc gcaagaagat cctcaagatc    960
cggcacgggt gggaggacgt gaccaagatc aacaagaccg agatctgcag ccagctgtga   1020
```

<210> SEQ ID NO 13
<211> LENGTH: 13
<212> TYPE: RNA
<213> ORGANISM: Artificial Sequence
<220> FEATURE:
<223> OTHER INFORMATION: description of sequence: Kozak sequence (see
      description p. 28)

<400> SEQUENCE: 13

```
gccgccacca ugg                                                         13
```

<210> SEQ ID NO 14
<211> LENGTH: 13
<212> TYPE: RNA
<213> ORGANISM: Artificial Sequence
<220> FEATURE:
<223> OTHER INFORMATION: description of sequence: generic stabilizing
      sequence contained in the 3 prime UTR of the very stable RNA which
      codes for alpha-globin, alpha(I)-collagen, 15-lipoxygenase or for
      tyrosine hydroxylase (see description p. 34)
<220> FEATURE:
<221> NAME/KEY: misc_feature
<222> LOCATION: (1)..(1)
<223> OTHER INFORMATION: n is c or u
<220> FEATURE:
<221> NAME/KEY: misc_feature
<222> LOCATION: (4)..()
<223> OTHER INFORMATION: any number of any ribonucleic acid can be
      inserted between positions 4 and 5
<220> FEATURE:
<221> NAME/KEY: misc_feature
<222> LOCATION: (8)..()
<223> OTHER INFORMATION: any number of pyrimidines can be inserted
      between positions 8 and 9
<220> FEATURE:
<221> NAME/KEY: misc_feature
<222> LOCATION: (8)..()
<223> OTHER INFORMATION: any number of pyrimidines can be inserted
      between positions 8 and 9
<220> FEATURE:
<221> NAME/KEY: misc_feature
<222> LOCATION: (8)..(8)
<223> OTHER INFORMATION: n is u or a
<220> FEATURE:
<221> NAME/KEY: variation
<222> LOCATION: (11)..(11)
<223> OTHER INFORMATION: n is c or u
<220> FEATURE:
<221> NAME/KEY: misc_feature
<222> LOCATION: (11)..(11)
<223> OTHER INFORMATION: n is a, c, g, or u

<400> SEQUENCE: 14

```
nccacccnuc ncc                                                         13
```

<210> SEQ ID NO 15
<211> LENGTH: 7
<212> TYPE: PRT
<213> ORGANISM: Artificial Sequence
<220> FEATURE:
<223> OTHER INFORMATION: oligoarginine

<400> SEQUENCE: 15

```
Arg Arg Arg Arg Arg Arg Arg
1               5
```

<210> SEQ ID NO 16

```
<211> LENGTH: 8
<212> TYPE: PRT
<213> ORGANISM: Artificial Sequence
<220> FEATURE:
<223> OTHER INFORMATION: oligoarginine

<400> SEQUENCE: 16

Arg Arg Arg Arg Arg Arg Arg Arg
1               5

<210> SEQ ID NO 17
<211> LENGTH: 9
<212> TYPE: PRT
<213> ORGANISM: Artificial Sequence
<220> FEATURE:
<223> OTHER INFORMATION: oligoarginine

<400> SEQUENCE: 17

Arg Arg Arg Arg Arg Arg Arg Arg Arg
1               5

<210> SEQ ID NO 18
<211> LENGTH: 7
<212> TYPE: PRT
<213> ORGANISM: Artificial Sequence
<220> FEATURE:
<223> OTHER INFORMATION: oligoarginine

<400> SEQUENCE: 18

Arg Arg Arg Arg Arg Arg Arg
1               5

<210> SEQ ID NO 19
<211> LENGTH: 12
<212> TYPE: PRT
<213> ORGANISM: Artificial Sequence
<220> FEATURE:
<223> OTHER INFORMATION: oligoarginine

<400> SEQUENCE: 19

His His His Arg Arg Arg Arg Arg Arg Arg Arg Arg
1               5                   10

<210> SEQ ID NO 20
<211> LENGTH: 12
<212> TYPE: PRT
<213> ORGANISM: Artificial Sequence
<220> FEATURE:
<223> OTHER INFORMATION: oligoarginine

<400> SEQUENCE: 20

Arg Arg Arg Arg Arg Arg Arg Arg Arg His His His
1               5                   10

<210> SEQ ID NO 21
<211> LENGTH: 15
<212> TYPE: PRT
<213> ORGANISM: Artificial Sequence
<220> FEATURE:
<223> OTHER INFORMATION: oligoarginine

<400> SEQUENCE: 21

His His His Arg Arg Arg Arg Arg Arg Arg Arg Arg His His His
1               5                   10                  15

<210> SEQ ID NO 22
<211> LENGTH: 15
```

```
<212> TYPE: PRT
<213> ORGANISM: Artificial Sequence
<220> FEATURE:
<223> OTHER INFORMATION: oligoarginine

<400> SEQUENCE: 22

Tyr Ser Ser Arg Arg Arg Arg Arg Arg Arg Arg Ser Ser Tyr
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: oligoarginine

<400> SEQUENCE: 23

Arg Lys His Arg Lys His Arg Lys His Arg Lys His
1               5                   10

<210> SEQ ID NO 24
<211> LENGTH: 8
<212> TYPE: PRT
<213> ORGANISM: Artificial Sequence
<220> FEATURE:
<223> OTHER INFORMATION: oligoarginine

<400> SEQUENCE: 24

Tyr Arg Lys His Arg Lys His Arg
1               5
```

The invention claimed is:

1. A kit comprising at least four different immunostimulatory compositions, wherein the at least four different immunostimulatory compositions are:
   (a) an immunostimulatory composition comprising an isolated STEAP (Six Transmembrane Epithelial Antigen of the Prostate) antigen coding RNA complexed with protamine;
   (b) an immunostimulatory composition comprising an isolated PSA (Prostate-Specific Antigen) antigen coding RNA complexed with protamine;
   (c) an immunostimulatory composition comprising an isolated PSMA (Prostate-Specific Membrane Antigen) antigen coding RNA complexed with protamine; and
   (d) an immunostimulatory composition comprising an isolated PSCA (Prostate Stem Cell Antigen) antigen coding RNA complexed with protamine.

2. The kit according to claim 1, further comprising an immunostimulatory composition comprising an isolated PAP (Prostatic Acid Phosphatase) antigen coding RNA complexed with protamine.

3. The kit according to claim 1, wherein the antigen coding RNA of said at least four different immunostimulatory compositions comprises a length of 250 to 20000 nucleotides.

4. The kit according to claim 1, wherein at least one of the at least four different immunostimulatory compositions comprises RNA that is mRNA.

5. The kit according to claim 1, wherein at least one of the at least four different immunostimulatory compositions comprises RNA that is monocistronic RNA.

6. The kit according to claim 5, wherein the antigen coding RNA of said at least four different immunostimulatory compositions is monocistronic RNA.

7. The kit according to claim 4, wherein the mRNA comprises a G/C content of the antigen coding region that is increased compared to the G/C content of a wild-type RNA encoding the antigen.

8. The kit according to claim 4, wherein the mRNA comprises an A/U content in the environment of the ribosome binding site that is increased compared with the A/U content of a wild-type RNA encoding the antigen.

9. The kit according to claim 4, wherein the mRNA comprises a 5' cap structure; a poly(A) tail; a poly(C) tail and/or a globin 3' untranslated region (3' UTR).

10. The kit according to claim 1, wherein at least one of said at least four different immunostimulatory compositions comprises at least one adjuvant.

11. The kit according to claim 1, wherein at least one of said at least four different immunostimulatory compositions comprises a pharmaceutically acceptable carrier.

12. The kit according to claim 4, wherein at least one of said at least four different immunostimulatory compositions comprises mRNA that does not comprise the sequence GAA-CAAG.

13. The kit according to claim 4, wherein the mRNA comprises a 3'UTR that does not comprise an AU-rich sequence.

14. The kit according to claim 1, wherein at least one of said at least four different immunostimulatory compositions comprises RNA that comprises a globin 3' UTR.

15. The kit according to claim 1,
   wherein each of said at least four different immunostimulatory compositions comprises isolated mRNA complexed with protamine and wherein each of said at least four different immunostimulatory compositions comprises mRNA comprising a 5' cap structure, a poly(A) tail, a globin 3' UTR, and a G/C content of the coding region, which is increased compared to the G/C content of wild-type RNA encoding the antigen.

16. The kit according to claim 2,
wherein each of said different immunostimulatory compositions comprises isolated mRNA complexed with protamine and wherein each of said different immunostimulatory compositions comprises mRNA comprising a 5' cap structure, a poly(A) tail, a globin 3' UTR, and a G/C content of the antigen coding region, which is increased compared to the G/C content of wild-type RNA encoding the antigen.

17. The kit according to claim 11, wherein the pharmaceutically acceptable carrier comprises Ringer-Lactate.

18. A method of treating a subject having prostate cancer (PCa) comprising administering an effective amount of the at least four different immunostimulatory compositions of a kit according to claim 1 to the subject.

19. The method according to claim 18, wherein the PCa is selected from a neoadjuvant prostate cancer and a hormone-refractory prostate cancer.

20. A method of treating a subject having PCa comprising administering an effective amount of said different immunostimulatory compositions of a kit according to claim 2 to the subject.

21. A kit comprising at least four different immunostimulatory compositions, wherein the at least four different immunostimulatory compositions are:
(a) an immunostimulatory composition comprising an isolated STEAP antigen coding RNA comprising a globin 3' UTR;
(b) an immunostimulatory composition comprising an isolated PSA antigen coding RNA comprising a globin 3' UTR;
(c) an immunostimulatory composition comprising an isolated PSMA antigen coding RNA comprising a globin 3' UTR; and
(d) an immunostimulatory composition comprising an isolated PSCA antigen coding RNA comprising a globin 3' UTR.

22. The kit according to claim 21, further comprising an immunostimulatory composition comprising an isolated PAP antigen coding RNA comprising a globin 3' UTR.

23. The kit according to claim 21, wherein at least one of said at least four different immunostimulatory compositions comprises RNA that is mRNA.

24. The kit according to claim 21, wherein at least one of said at least four different immunostimulatory compositions comprises RNA that is monocistronic RNA.

25. The kit according to claim 21, wherein the antigen coding RNA of said at least four different immunostimulatory compositions is monocistronic RNA.

26. The kit according to claim 23, wherein the mRNA comprises a G/C content of the antigen coding region that is increased compared to the G/C content of a wild-type RNA encoding the antigen.

27. The kit according to claim 23, wherein the mRNA comprises an A/U content in the environment of the ribosome binding site that is increased compared with the A/U content of a wild-type RNA encoding the antigen.

28. The kit according to claim 23, wherein the mRNA comprises a 5' cap structure; a poly(A) tail; and/or a poly(C) tail.

29. The kit according to claim 21, wherein at least one of said at least four different immunostimulatory compositions comprises RNA that is complexed with one or more polycationic molecules.

30. The kit according to claim 29, wherein the one or more polycationic molecules comprise protamine.

31. The kit according to claim 21, wherein at least one of said at least four different immunostimulatory compositions comprises at least one adjuvant.

32. The kit according to claim 21, wherein at least one of said at least four different immunostimulatory compositions comprises a pharmaceutically acceptable carrier.

33. A method of treating a subject having PCa comprising administering an effective amount of said at least four different immunostimulatory compositions of a kit according to claim 21 to the subject.

34. A method of treating a subject having PCa comprising administering an effective amount of said different immunostimulatory compositions of a kit according to claim 22 to the subject.

35. A kit comprising at least four different immunostimulatory compositions, wherein the at least four different immunostimulatory compositions are:
(a) an immunostimulatory composition comprising an isolated STEAP antigen coding RNA;
(b) an immunostimulatory composition comprising an isolated PSA antigen coding RNA;
(c) an immunostimulatory composition comprising an isolated PSMA antigen coding RNA; and
(d) an immunostimulatory composition comprising an isolated PSCA antigen coding RNA,
wherein at least one of said immunostimulatory compositions comprises an isolated RNA comprising a G/C content of the antigen coding region that is increased by at least 7% points compared to the G/C content of a wild-type RNA encoding the antigen.

36. The kit according to claim 35, further comprising an immunostimulatory composition comprising an isolated PAP antigen coding RNA comprising a G/C content of the antigen coding region that is increased compared to the G/C content of a wild-type RNA encoding the antigen.

37. The kit according to claim 35, wherein at least one of said at least four different immunostimulatory compositions comprises RNA that is mRNA.

38. The kit according to claim 35, wherein at least one of said at least four different immunostimulatory compositions comprises RNA that is monocistronic RNA.

39. The kit according to claim 35, wherein the antigen coding RNA of said at least four different immunostimulatory compositions is monocistronic RNA.

40. The kit according to claim 37, wherein the mRNA comprises an A/U content in the environment of the ribosome binding site that is increased compared with the A/U content of a wild-type RNA encoding the antigen.

41. The kit according to claim 37, wherein the mRNA comprises a 5' cap structure; a poly(A) tail; a poly(C) tail; and/or a globin 3'UTR.

42. The kit according to claim 35, wherein at least one of said at least four different immunostimulatory compositions comprises RNA that is complexed with one or more polycationic molecules.

43. The kit of claim 42, wherein the one or more polycationic molecules comprise protamine.

44. The kit according to claim 35, wherein at least one of said at least four different immunostimulatory compositions comprises at least one adjuvant.

45. The kit according to claim 35, wherein at least one of said at least four different immunostimulatory compositions comprises a pharmaceutically acceptable carrier.

46. The kit of claim 35, wherein at least one of said at least four different immunostimulatory compositions comprises RNA that comprises a globin 3' UTR.

47. A method of treating prostate cancer in a subject comprising administering an effective amount of said at least four different immunostimulatory compositions of a kit according to claim 35 to the subject.

48. A method of treating prostate cancer in a subject comprising administering an effective amount of said different immunostimulatory compositions of a kit according to claim 36 to the subject.

* * * * *